US012692533B2

(12) United States Patent
Kwong et al.

(10) Patent No.: US 12,692,533 B2
(45) Date of Patent: Jul. 28, 2026

(54) METHODS AND COMPOSITIONS FOR NONINVASIVE DETECTION OF ORGAN TRANSPLANT REJECTION

(71) Applicants: Georgia Tech Research Corporation, Atlanta, GA (US); Emory University, Atlanta, GA (US)

(72) Inventors: Gabriel A. Kwong, Atlanta, GA (US); Andrew B. Adams, Atlanta, GA (US); Quoc Mac, Atlanta, GA (US); David V. Mathews, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 0 days.

(21) Appl. No.: 17/574,947

(22) Filed: Jan. 13, 2022

(65) Prior Publication Data

US 2022/0186285 A1     Jun. 16, 2022

Related U.S. Application Data

(63) Continuation of application No. 16/337,886, filed as application No. PCT/US2017/054105 on Sep. 28, 2017, now abandoned.

(60) Provisional application No. 62/400,656, filed on Sep. 28, 2016.

(51) Int. Cl.
| | |
|---|---|
| *C12Q 1/37* | (2006.01) |
| *C07K 5/00* | (2006.01) |
| *C07K 7/00* | (2006.01) |
| *C07K 14/00* | (2006.01) |

(52) U.S. Cl.
CPC .................. *C12Q 1/37* (2013.01); *C07K 5/00* (2013.01); *C07K 7/00* (2013.01); *C07K 14/00* (2013.01); *G01N 2800/245* (2013.01)

(58) Field of Classification Search
CPC ... C12Q 1/37; C12Q 1/25; C12Q 1/48; C07K 5/00; C07K 7/00; C07K 14/00; G01N 2800/245; G01N 33/68; G01N 33/53; G01N 33/573
See application file for complete search history.

(56) References Cited

U.S. PATENT DOCUMENTS

| | | | |
|---|---|---|---|
| 5,013,556 A | 5/1991 | Woodle et al. | |
| 6,592,847 B1 | 7/2003 | Weissleder et al. | |
| 7,179,655 B2 | 2/2007 | Patricelli | |
| 7,329,506 B2 | 2/2008 | Ward et al. | |
| 7,833,728 B2 | 11/2010 | Pastorek et al. | |
| 8,209,130 B1 | 6/2012 | Kennedy et al. | |
| 8,519,115 B2 | 8/2013 | Webster et al. | |
| 8,551,727 B2 | 10/2013 | Kwon et al. | |
| 8,673,267 B2 | 3/2014 | Bhatia et al. | |
| 8,858,987 B2 | 10/2014 | Cullen et al. | |
| 9,999,687 B2 | 6/2018 | Rajopadhye et al. | |
| 10,006,916 B2 | 6/2018 | Kwong et al. | |
| 2004/0091943 A1 | 5/2004 | Schneider | |
| 2005/0191680 A1 | 9/2005 | Bruno et al. | |
| 2009/0304719 A1 | 12/2009 | Daugherty et al. | |
| 2010/0015607 A1 | 1/2010 | Geiss et al. | |
| 2010/0047924 A1 | 2/2010 | Webster et al. | |
| 2010/0124757 A1 | 5/2010 | Kwon et al. | |
| 2010/0131432 A1 | 5/2010 | Kennedy et al. | |
| 2010/0240050 A1 | 9/2010 | Bhatia et al. | |
| 2011/0189680 A1 | 8/2011 | Keown et al. | |
| 2011/0229888 A1 | 9/2011 | Hengen et al. | |
| 2011/0244483 A1 | 10/2011 | Leeming et al. | |
| 2011/0256567 A1 | 10/2011 | Berthelot et al. | |
| 2013/0017223 A1 | 1/2013 | Hope et al. | |
| 2013/0017971 A1 | 1/2013 | Geiss et al. | |
| 2013/0116405 A1 | 5/2013 | Yu et al. | |
| 2014/0242612 A1 | 8/2014 | Wang et al. | |
| 2014/0363833 A1* | 12/2014 | Bhatia .............. G01N 33/54306 |
| | | | 435/7.92 |
| 2015/0018517 A1 | 1/2015 | Rajopadhye et al. | |
| 2015/0065420 A1 | 3/2015 | Soliman et al. | |
| 2015/0132230 A1 | 5/2015 | Bossmann et al. | |
| 2015/0132785 A1 | 5/2015 | Bossmann et al. | |
| 2015/0133752 A1 | 5/2015 | Iverson et al. | |
| 2015/0247149 A1 | 9/2015 | Feldstein et al. | |
| 2016/0206726 A1 | 7/2016 | Cobbold et al. | |
| 2017/0049904 A1 | 2/2017 | Lin et al. | |
| 2017/0176458 A1 | 6/2017 | Veidal et al. | |
| 2017/0369843 A1 | 12/2017 | Kahvejian et al. | |
| 2018/0023114 A1 | 1/2018 | Morin et al. | |
| 2018/0085466 A1 | 3/2018 | Bradley et al. | |
| 2018/0335429 A1 | 11/2018 | Bhatia et al. | |
| 2019/0256833 A1 | 8/2019 | Chung et al. | |
| 2019/0345534 A1 | 11/2019 | Kwong et al. | |

(Continued)

FOREIGN PATENT DOCUMENTS

| | | | | |
|---|---|---|---|---|
| CN | 1281346 A | * | 1/2001 | ......... C07K 5/06026 |
| JP | 2009518446 A | | 5/2009 | |
| JP | 2010536370 A | | 12/2010 | |

(Continued)

OTHER PUBLICATIONS

Lin et al., ACSNano, 7:10, 9001-9009, 2013 (Year: 2013).*
Venner et al., American Journal of Transplantation 2015; 15: 1336-1348 (Year: 2015).*
Chowdhury and Lieberman, Annu Rev Immunol. 2008 ; 26: 389-420 (Year: 2008).*
Chen et al., Adv Drug Deliv Rev. Oct. 15, 2013; 65(10): 1357-1369 (Year: 2013).*
Adessi and Soto, Current Medicinal Chemistry, 2002, 9, 963-978 (Year: 2002).*
Trapani and Sutton, Current Opinion in Immunology 2003, 15:533-543 (Year: 2003).*
Rao et al., RSC Adv., 2014, 4, 45625-45634 (Year: 2014).*
Davalos et al., Ann Neurol 2014;75:303-308 (Year: 2014).*

(Continued)

*Primary Examiner* — Joseph Fischer
(74) *Attorney, Agent, or Firm* — Meunier Carlin & Curfman LLC

(57) ABSTRACT

An activity-based nanosensor composition for detecting protease activity comprising a cleavable detectable substrate and methods of use are disclosed.

7 Claims, 19 Drawing Sheets

Specification includes a Sequence Listing.

(56) References Cited

U.S. PATENT DOCUMENTS

| | | | |
|---|---|---|---|
| 2019/0375796 A1 | 12/2019 | Touti et al. | |
| 2022/0249369 A1 | 8/2022 | Holt et al. | |

FOREIGN PATENT DOCUMENTS

| | | | |
|---|---|---|---|
| JP | 2012514982 A | 7/2012 | |
| JP | 2016505138 A | 2/2016 | |
| JP | 2017509594 A | 4/2017 | |
| KR | 20150129908 A | 11/2015 | |
| WO | 2002014867 A2 | 2/2002 | |
| WO | 2004005348 A1 | 1/2004 | |
| WO | 2007011660 A2 | 1/2007 | |
| WO | 2007076129 A2 | 7/2007 | |
| WO | 2008018933 A2 | 2/2008 | |
| WO | 2008127019 A1 | 10/2008 | |
| WO | 2009025846 A2 | 2/2009 | |
| WO | WO-2009111470 A2 | 9/2009 | |
| WO | 2010019826 A1 | 2/2010 | |
| WO | 2010101628 A2 | 9/2010 | |
| WO | 2011116088 A2 | 9/2011 | |
| WO | 2012125808 A1 | 9/2012 | |
| WO | 2012178046 A2 | 12/2012 | |
| WO | 2014028861 A1 | 2/2014 | |
| WO | 2014079802 A2 | 5/2014 | |
| WO | 2014197816 A1 | 12/2014 | |
| WO | 2014197840 A1 | 12/2014 | |
| WO | 2015154006 A1 | 10/2015 | |
| WO | WO-2015148622 A1 | 10/2015 | |
| WO | 2017177115 A1 | 10/2017 | |
| WO | 2017180587 A2 | 10/2017 | |
| WO | 2017193070 A1 | 11/2017 | |
| WO | 2018068135 A1 | 4/2018 | |
| WO | WO-2018064383 A1 | 4/2018 | |
| WO | 2019236989 A1 | 12/2019 | |
| WO | 2019236991 A1 | 12/2019 | |
| WO | 2019236992 A1 | 12/2019 | |
| WO | 2019237066 A1 | 12/2019 | |
| WO | 2020160227 A1 | 8/2020 | |
| WO | 2020160232 A1 | 8/2020 | |

OTHER PUBLICATIONS

Casciola-Rosen et al., J. Exp. Med., vol. 190, No. 6, Sep. 20, 1999 815-825 (Year: 1999).*

Gallwitz et al., PLoS One, Feb. 2012 | vol. 7, Issue 2, e31756 (Year: 2012).*

Ludwicka-Bradley et al, Semin Arthritis Rheum 41:212-222 (2011) (Year: 2011).*

Boivin et al., Laboratory Investigation (2009) 89, 1195-1220 (Year: 2009).*

Ling et al., Acc. Chem. Res. 2015, 48, 1276-1285 (Year: 2015).*

Dudani et al., ACSNano, vol. 9, No. 12, pp. 11708-11717, 2015 (Year: 2015).*

Konishi et al., Circ Res. 2015;117:502-512 (Year: 2015).*

"Barchetta, et al. "Circulating dipeptidyl peptidase-4 is independently associated with the presence and severtiy of NAFLD/NASH in individuals with and without obesity and metabolic disease" Journal of Endocrinological Investigation (2021) 44: 979-988".

"International Search Report and Written Opinion for PCT Application No. PCT/US2017/054105, dated Jan. 18, 2018".

"Kalubowilage, et al., "Early detection of pancreatic cancewrs in liquid biopsies by ultrasensitive fluorescence nanobiosensors" Nanomedicine: Nanotechnology, Biology, and Medicine 14 (2018) 1823-1832".

"Matheeussen, et al., "Method comparison of dipeptidyl peptidase IV activity assays and their applications in biological samples containing reversible inhibitors" Clinica Chimica Acta 413 (212) 456-462".

"Udukala, et al. "Early detection of non-small cell lung cancer in liquid biopsies by ultrasensitive protease activity analysis" J Cancer Metastasis Treat (2020); 6;25".

Li, "Functionalization of gold nanoparticles for biomedical and catalyic applications", The University of Bordeaux, Hal Open Science, pp. 1-140 (2014).

Abudayyeh O.O., "Nanoparticle-Chaperoned Urinary 'Synthetic Biomarkers' for Profiling Proteases in Cancer," MIT Thesis, 2012, 63 Pages.

Allard B., et al., "The Ectonucleotidases CD 39 and CD 73: Novel Checkpoint Inhibitor Targets," Immunological reviews, Mar. 2017, vol. 276, No. 1, 47 pages.

Arias M., et al., "The Untold Story of Granzymes in Oncoimmunology: Novel Opportunities with Old Acquaintances," Trends in Cancer, Jun. 2017, vol. 3, No. 6, pp. 407-422.

Aungier S., et al., "The Extracellular Matrix: A New Dimension in Disease Diagnosis and Treatment," Biochemist, Aug. 2016, vol. 38, No. 4, pp. 10-15.

Bonnans C., et al., "Remodelling the Extracellular Matrix in Development and Disease," Nature Reviews Molecular Cell Biology, Dec. 2014, vol. 15, No. 12, pp. 786-801.

Breiman L., "Random Forests," Machine Learning, Oct. 2001, vol. 45, No. 1, pp. 5-32.

Buss C.G., et al., "Protease Activity Sensors Noninvasively Classify Bacterial Infections and Antibiotic Responses," EBiomedicine, 2018, vol. 38, pp. 248-256, Retrieved from URL: https://doi.Org/10.1016/j.ebiom.2018.11.031.

Chikuma S., et al., "Suppressors of Cytokine Signaling: Potential Immune Checkpoint Molecules for Cancer Immunotherapy," Cancer Science, Apr. 2017, vol. 108, No. 4, pp. 574-580.

Cohen J. D., et al., "Detection and Localization of Surgically Resectable Cancers with a Multi-analyte Blood Test," Science, Jan. 18, 2018, vol. 359, No. 6378, pp. 926-930.

Cyll K., et al., "Tumour Heterogeneity Poses a Significant Challenge to Cancer Biomarker Research," British Journal of Cancer, 2017, vol. 117, No. 3, pp. 367-375.

Deshpande P. P., et al., "Current Trends in the Use of Liposomes for Tumor Targeting," Nanomedicine (London, England), Sep. 2013, vol. 8, No. 9, pp. 1509-1528 (32 Pages).

Dudani J.S., et al., "Classification of Prostate Cancer using a Protease Activity Nanosensor Library," PNAS, Sep. 4, 2018, vol. 115, No. 36, pp. 8954-8959.

Dudani J.S., et al., "Harnessing Protease Activity to Improve Cancer Care," Annual Review of Cancer Biology, 2018, vol. 2, pp. 353-376 (26 Pages).

Dudani J.S., "Sustained-Release Synthetic Biomarkers for Monitoring Thrombosis and Inflammation using Point-of-Care Compatible Readouts," Advanced Functional Materials, May 3, 2016, vol. 26, No. 17, pp. 2919-2928 (20 Pages).

Egeblad M., et al., "New Functions for the Matrix Metalloproteinases in Cancer Progression," Nature Reviews Cancer, Mar. 2002, vol. 2, No. 3, pp. 161-174 (15 Pages).

Elion J., et al., "Proteolytic Derivatives of Thrombin," Annals of the New York Academy of Sciences, 1986, pp. 16-26.

Evers T.H., et al., "Quantitative Understanding of the Energy Transfer Between Fluorescent Proteins Connected via Flexible Peptide Linkers," Biochemistry, 2006, vol. 45, No. 44, pp. 13183-13192.

Extended European Search Report for European Application No. 17857448.9, dated May 7, 2020, 10 Pages.

Extended European Search Report for European Application No. 19860757.4, dated May 17, 2022, 8 Pages.

Extended European Search Report for European Application No. 20772887.4, dated Mar. 28, 2023, 10 Pages.

Friedman A.D., et al., "The Smart Targeting of Nanoparticles," Current Pharmaceutical Design, 2013, vol. 19, No. 35, pp. 6315-6329 (28 Pages).

Galati R., et al., "Increased Resistance of Peptides to Serum Proteases by Modification of their Amino Groups," Zeitschrift fur Naturforschung, 2003, vol. 58c, pp. 558-561.

Gang D., et al., "Cyclic Peptides: Promising Scaffolds for Biopharmaceuticals," Genes, 2018, vol. 9(11), No. 557, 15 Pages.

Gentleman R C., et al., "Bioconductor: open software development for computational biology and bioinformatics," Genome Biology, 2024, vol. 5, No. 10 R80, 16 pages.

(56)　　　　　References Cited

OTHER PUBLICATIONS

Gootenberg U.S., et al., "Multiplexed and Portable Nucleic Acid Detection Platform with Cas13, Cas12a, and Csm6," Science, 2018, vol. 360, No. 6387, pp. 439-444 (10 Pages).

Gootenberg U.S., et al., "Nucleic Acid Detection with CRISPRCasl3a/C2c2," Science, Apr. 28, 2017, vol. 356, No. 6336, pp. 438-442(12 Pages).

Gural N., et al., "Engineered Livers for Infection Diseases," Cellular and Molecular Gastroenterology and Hepatology, 2018, vol. 5, No. 2, pp. 131-144.

Hailfinger S., et al., "Adapter and Enzymatic Functions of Proteases in T-Cell Activation," ImmuNological Reviews, 2009, vol. 232, pp. 334-347.

Haines J., et al., "A Quantitative Volumetric Micro-Computed Tomography Method to Analyze Lung Tumors in Genetically Engineered Mouse Models," Neoplasia, 2009, vol. 11, No. 1, pp. 39-47.

Hann J., et al., "Usefulness of Highly Sensitive AFP-L3 and DCP in Surveillance for Hepatocellular Carcinoma in Patients with a Normal Alpha-Fetoprotein," Jefferson Digital Commons, 2014, 8 pages.

Harris T.J., et al., "Protease-Triggered Unveiling of Bioactive Nanoparticles," Small, 2008, vol. 4, No. 9, pp. 1307-1312.

Holt B.A., et al., "Nanosensors to Detect Protease Activity in Vivo for Noninvasive Diagnostics," Journal of Visualized Experiments, Jul. 16, 2018, vol. 137 No. e57937, pp. 1-6.

Holt B.A., et al., "Protease Circuits for Processing Biological Information," Nature Communications, Oct. 6, 2020, vol. 11, No. 1, DOI: 10.1038/s41467-020-18840-8, XP093032562, Retrieved from URL: https://www.ncbi.nlm.nih.gov/pmc/articles/PMC7538567/pdf/41467_2020_Article_18840.pdf.

Holt B.A., et al., "Proteases as Biological Bits for Programmable Medicine," bioRxiv, Apr. 12, 2019, pp. 1-43 (42 Pages), [Retrieved on 2022-06-03] Retrieved from URL: https://www.biorxiv.org/content/10.1101/607895v1.full.pdf.

Hori S.S., et al., "Mathematical Model Identifies Blood Biomarker-Based Early Cancer Detection Strategies and Limitations," Science Translational Medicine, Nov. 16, 2011, vol. 3, No. 109, 109ra116, 19 Pages.

Hoshyar N., et al., "The Effect of Nanoparticle Size on in Vivo Pharmacokinetics and Cellular Interaction," Nanomedicine (Lond.), 2016, vol. 11, No. 6, pp. 673-692.

Huber W., et al., "Orchestrating high-throughput genomic analysis with Bioconductor," Nature Methods, 2015, vol. 12, pp. 115-121.

Hughes C.J.R., et al., "Dissecting the Role of the Extracellular Matrix in Heart Disease: Lessons from the Drosophila Genetic Model," Veterinary Sciences, 2017, vol. 4, No. 24, pp. 1-28.

International Search Report and Written Opinion for International Application No. PCT/US2019/036036, dated Sep. 12, 2019, 9 Pages.

International Search Report and Written Opinion for International Application No. PCT/US2019/036039, dated Oct. 24, 2019, 11 Pages.

International Search Report and Written Opinion for International Application No. PCT/US2019/036041, dated Sep. 19, 2019, 8 Pages.

International Search Report and Written Opinion for International Application No. PCT/US2019/036155, dated Sep. 4, 2019, 8 Pages.

International Search Report and Written Opinion for International Application No. PCT/US2019/050530, dated Dec. 19, 2019, 9 Pages.

International Search Report and Written Opinion for International Application No. PCT/US2020/015823, dated Apr. 28, 2020, 10 Pages.

International Search Report and Written Opinion for International Application No. PCT/US2020/015828, dated Jun. 18, 2020, 8 Pages.

International Search Report and Written Opinion for International Application No. PCT/US2020/30132, dated Oct. 22, 2020, 37 Pages.

Jia L., et al., "An Attempt to Understand Kidney's Protein Handling Function by Comparing Plasma and Urine Proteomes," PLoS One, Apr. 2009, vol. 4, Issue. 4, e5146, 9 Pages.

Josephson L., et al., "Near-Infrared Fluorescent NaNoparticles as Combined MR/Optical Imaging Probes," Bioconjugate Chemistry, American Chemical Society, US, May 1, 2002, vol. 13, No. 3, pp. 554-560, DOI: 10.1021/BC015555D, ISSN 1043-1802, XP002267675.

Kappelhoff R., et al., "Overview of Transcriptomic Analysis of All Human Proteases, Non-Proteolytic Homologs and Inhibitors: Organ, Tissue and Ovarian Cancer Cell Line Expression Profiling of the Human Protease Degradome by the Clip-Chip™ DNA Microarray," Biochimica et Biophysica Acta—Molecular Cell Research, 2017, vol. 1864, pp. 2210-2219.

Khair D.O., et al., "Combining Immune Checkpoint Inhibitors: Established and Emerging Targets and Strategies to Improve Outcomes in Melanoma," Frontiers in Immunology, Mar. 19, 2019, vol. 10, Article. 453, 20 Pages.

Kircher M.F., et al., "A Dual Fluorochrome Probe for Imaging Proteases," Bioconjugate Chemistry, 2004, vol. 15, No. 2, pp. 242-248.

Klingler D., et al., "Profiling Protease Activities with Dynamic Proteomics Workflows," Proteomics, Feb. 2012, vol. 12, No. 4-5, pp. 587-596 (17 Pages).

Kristensen M., et al., "Cell-Penetrating Peptides as Tools to Enhance Non-Injectable Delivery of Biopharmaceuticals," Tissue Barriers, 2016, vol. 4, No. 2, e1178369, 15 Pages.

Kulkarni A., et al., "Reporter Nanoparticle that Monitors its Anticancer Efficacy in Real Time," PNAS Early Edition, 2016, 10 Pages.

Kutlu O., et al., "Molecular Pathogenesis of Nonalcoholic Steatohepatitis-(NASH-) Related Hepatocellular Carcinoma," Canadian Journal of Gastroenterology and Hepatology, vol. 2018, Article ID. 8543763, 10 p. 2018.

Kwon E.J., et al., "Ultrasensitive Tumor-Penetrating Nanosensors of Protease Activity," Nature Biomedical Engineering, Apr. 10, 2017, vol. 1, Article No. 0054, 10 Pages.

Kwong G.A., et al., "Mass-Encoded Synthetic Biomarkers for Multiplexed Urinary Monitoring of Disease," Nature Biotechnology, Jan. 2013, vol. 31, No. 1, pp. 63-70 (29 Pages), DOI: 10.1038/nbt.2464, ISSN: 1087-0156, XP055070926.

Kwong G.A., et al., "Mathematical Framework for Activity-Based Cancer Biomarkers," PNAS, Oct. 13, 2015, vol. 112, No. 41, p. 12627-12632 (12 Pages).

Larimer B.M., et al., "Granzyme B Pet Imaging as a Predictive Biomarker of Immunotherapy Response," Cancer Research, May 1, 2017, vol. 77, No. 9, pp. 2318-2327 (20 Pages).

Lau J.L., et al., "Therapeutic Peptides: Historical Perspectives, Current Development Trends, and Future Directions," Bioorganic & Medicinal Chemistry, 2018, vol. 26, pp. 2700-2707.

Lee J., et al., "Implementation of a Multiplex and Quantitative Proteomics Platform for Assessing Protein Lysates using DNA-Barcoded Antibodies," Molecular & Cellular Proteomics, 2018, vol. 17, No. 6, pp. 1245-1258.

Lin C-C., et al., "PEG Hydrogels for the Controlled Release of Biomolecules in Regenerative Medicine," Pharmaceutical Research, Mar. 2009, vol. 26, No. 3, pp. 631-643.

Lin C-C., et al., "The Biodegradation of Biodegradable Polymeric Biomaterials," Chapter II.4.3 in Biomaterials Science 3d Edition, Ratner et al., Eds Academic Press, 2013, pp. 716-728.

Lo J.H., et al., "iRGD-Guided Tumor-Penetrating Nanocomplexes for Therapeutic siRNA Delivery to Pancreatic Cancer," Molecular Cancer Therapeutics, Nov. 2018, vol. 17, No. 11, pp. 2377-2388 (13 Pages).

Luther J., et al., "Hepatic Connexin 32 Associates with Nonalcoholic Fatty Liver Disease Severity," Hepatology Communications, Jul. 2018, vol. 2, No. 7, pp. 786-797.

Mallinckrodt C.H., et al., "Assessing and Interpreting Treatment Effects in Longitudinal Clinical Trials with Missing Data," Biological Psychiatry, 2003, vol. 53, pp. 754-760.

Mason S.D., et al., "Proteolytic Networks in Cancer," Trends in Cell Biology, Apr. 2011, vol. 21, No. 4, pp. 228-237 (18 Pages).

Mauiyyedip S., et al., "Chronic Humoral Rejection: Identification of Antibody-Mediated Chronic Renal Allograft Rejection by C4d

(56) References Cited

OTHER PUBLICATIONS

Deposits in Peritubular Capillaries," Journal of the American Society of Nephrology (JASN), 2001, vol. 12, pp. 574-582.

Metz C.E., "Basic Principles of ROC Analysis," Seminars in Nuclear Medicine, Oct. 1978, vol. 8, No. 4, pp. 283-298.

Milletti F., "Cell-Penetrating Peptides: Classes, Origin, and Current Landscape," Drug Discovery Today, Aug. 1, 2012, vol. 17, No. 15/16, pp. 850-860.

Nagrath S., et al., "Isolation of Rare Circulating Tumour Cells in Cancer Patients by Microchip Technology," Nature, Dec. 20, 2007, vol. 450, No. 7173, pp. 1235-1239 (11 Pages).

Nam C. et al., "CT and MRI Improve Detection of Hepatocellular Carcinoma, Compared With Ultrasound Alone, in Patients With Cirrhosis," Clinical Gastroenterology and Hepatology, 2011, vol. 9, pp. 161-167.

Ncbi Genbank: "Fe-S Oxidoreductase [Serpentinimonas Maccroryi]," NCBI Reference Sequence No. BAO83571.1, Nov. 27, 2018, 2 Pages, 2014, Downloaded via the Worldwide Web/Internet from www.ncbi.com During a BLAST Sequence Search on Apr. 6, 22.

Nguyen A. T., et al., "The Prototype HIV-1 Maturation Inhibitor, Bevirimat, Binds to the CA-SP1 Cleavage Site in Immature Gag Particles," Retrovirology, 2011, vol. 8, No. 101, 13 Pages.

Zegarska J., et al., "Extracellular Matrix Proteins, Proteolytic Enzymes, and TGF-Beta1 in the Renal Arterial Wall of Chronically Rejected Renal Allografts," Transplant Proceedings, 2003, vol. 35, pp. 2193-2195, DOI: 10.1016/ S0041-1345(03)00789-9, XP005160877.

Raagel H., et al., "Peptide-Mediated Protein Delivery-Which Pathways are Penetrable?," Biochimica et Biophysica Acta, 2010, vol. 1798, No. 12, pp. 2240-2248.

Robinson C.R., et al., "Optimizing the Stability of Single-chain Proteins by Linker Length and Composition Mutagenesis," Proceedings of the National Academy of Sciences, May 1998, vol. 95, No. 11, pp. 5929-5934.

Sanchez-Martin D., et al., "Selection Strategies for Anti-Cancer Antibody Discovery: Searching off the Beaten Path," Trends in Biotechnology, May 2015, vol. 33, No. 5, pp. 292-301 (20 Pages), 2017.

Schuerle S., et al., "Magnetically Actuated Protease Sensors for in Vivo Tumor Profiling," Nano Letters, 2016, vol. 16, No. 10, pp. 6303-6310 (22 Pages).

Simard B., et al., "Site-Specific Conjugation of the Quencher on Peptide's N-Terminal for the Synthesis of a Targeted Non-Spreading Activatable Optical Probe," Journal of Peptide Science, 2016, vol. 22, No. 6, pp. 415-420.

Singal A., et al., "Meta-analysis: surveillance with ultrasound for early-stage hepatocellular carcinoma in patients with cirrhosis," Alimentary Pharmacology & Therapeutics, 2009, vol. 30, pp. 37-47.

Sjoblom T., et al., "The Consensus Coding Sequences of Human Breast and Colorectal Cancers," Science, Oct. 13, 2006, vol. 314, No. 5797, pp. 268-274.

Song J., et al., "Prosper: An Integrated Feature-Based Tool for Predicting Protease Substrate Cleavage Sites," PLoS One, Nov. 2012, vol. 7, Issue. 11, e50300, 23 Pages.

Sorenson., "Selection of antibodies against a single rare cell present in a heterogeneous population using phage display", Nature Protocols, 2011, vol. 6,No. 4, pp. 509-522.

Stegall M.D., et al., "The Role of Complement in Antibody-Mediated Rejection in Kidney Transplantation," Nature Reviews Nephrology, 2012, vol. 8, pp. 670-678, DOI:10.1038/nrneph.2012. 212, XP055293015.

Tascilar M., et al., "Role of Tumor Markers and Mutations in Cells and Pancreatic Juice in the Diagnosis of Pancreatic Cancer," Annals of Oncology, 1999, vol. 10, Supplement. 4, pp. s107-s110.

Tockman M.S., et al., "Considerations in Bringing a Cancer Biomarker to Clinical Application," Cancer Research, May 1, 1992, vol. 52, pp. 2711s-2718s.

Van Lehn R.C., et al., "Penetration of Lipid Bilayers by Nanoparticles with Environmentally-Responsive Surfaces," Soft Matter, 2011, vol. 7, pp. 11392-11404.

Voskoboink I., et al., "Perforin and Granzymes: Function, Dysfunction and Human Pathology," Nature Reviews Immunology, Jun. 2015, vol. 15, No. 6, pp. 388-400.

Wang M., et al., "Changes in the Glycosylation of Kininogen and the Development of a Kininogen-Based Algorithm for the Early Detection of HCC," Cancer Epidemiology, Biomarkers & Prevention, 2017, vol. 26, No. 5, 9 pages.

Wang P., et al., "Mass Spectrometry-Based Protein Identification by Integrating De Novo Sequencing with Database Searching," BMC Bioinformatics, 2013, vol. 14, Supplement. 2, No. S24, 9 Pages.

Wang Z., et al., "RNA-Seq: a revolutionary tool for transcriptomics," Nature Reviews Genetics, 2009, vol. 10, No. 1, 16 pages.

Warren A.D., et al., "Disease Detection by Ultrasensitive Quantification of Microdosed Synthetic Urinary Biomarkers," JACS, 2014, vol. 136, p. 13709-13714 (14 Pages).

Warren A.D., et al., "Point-of-Care Diagnostics for Noncommunicable Diseases using Synthetic Urinary Biomarkers and Paper Microfluidics," PNAS, Mar. 11, 2014, vol. 111, No. 10, pp. 3671-3676 (12 Pages).

Wong W., et al., "Chronic Humoral Rejection of Human Kidney Allografts is Associated with MMP-2 Accumulation in Podocytes and Its Release in the Urine," American Journal of Transplantation, 2010, vol. 10, pp. 2463-2471.

* cited by examiner

Figure 3A
Figure 3B
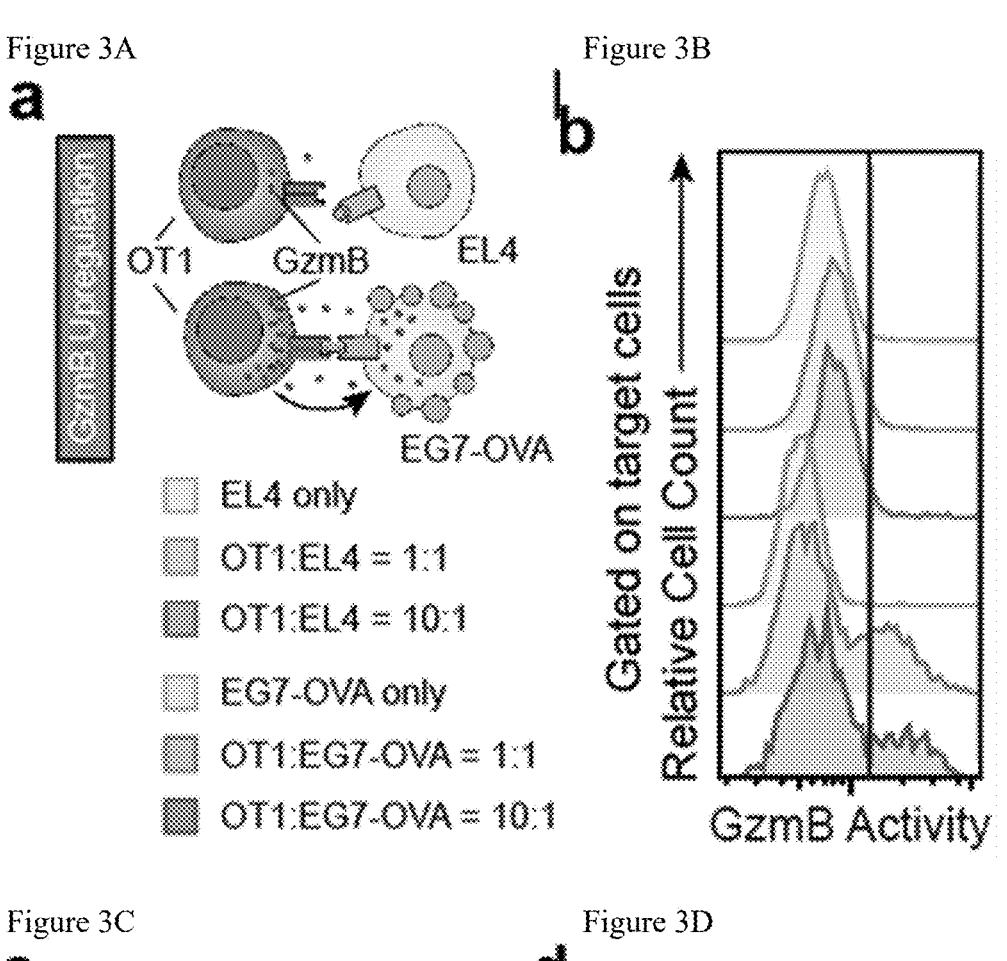
Figure 3C
Figure 3D
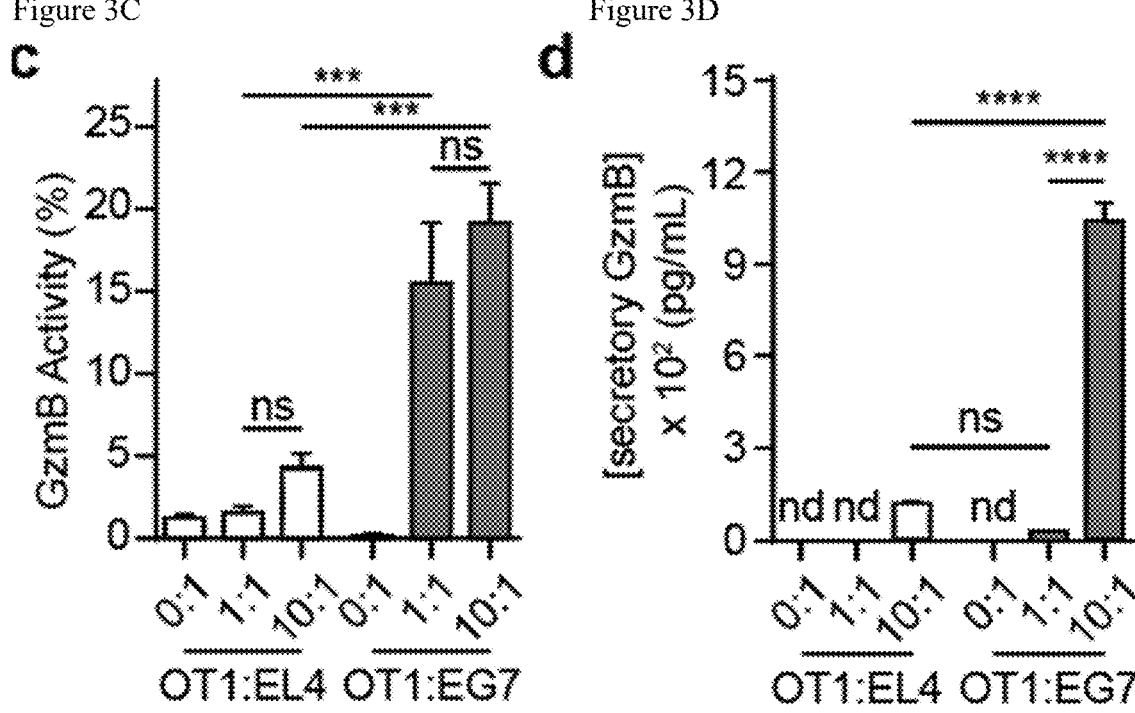

Figure 3I
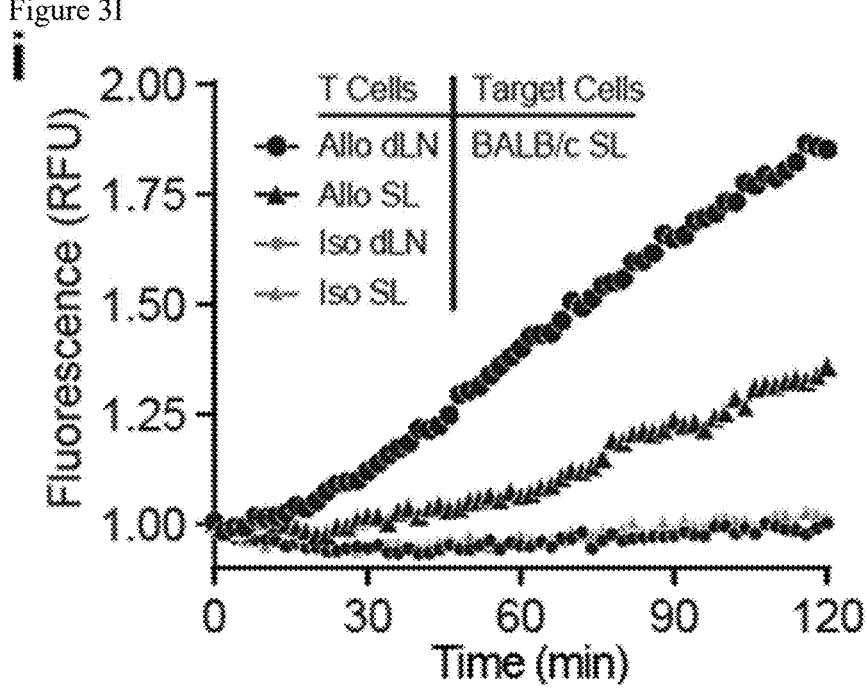
Figure 4A
Figure 4B
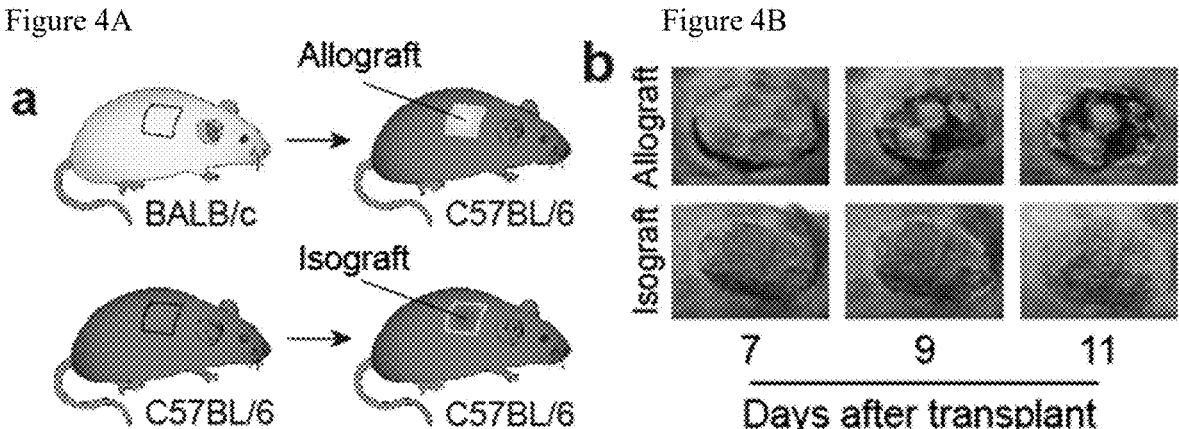

Figure 4G
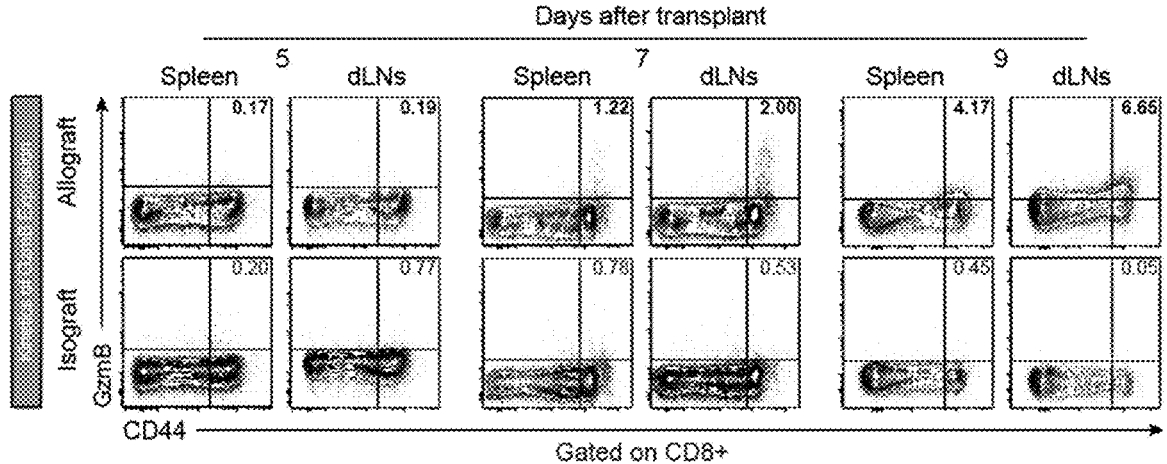
Figure 5A
Figure 5B
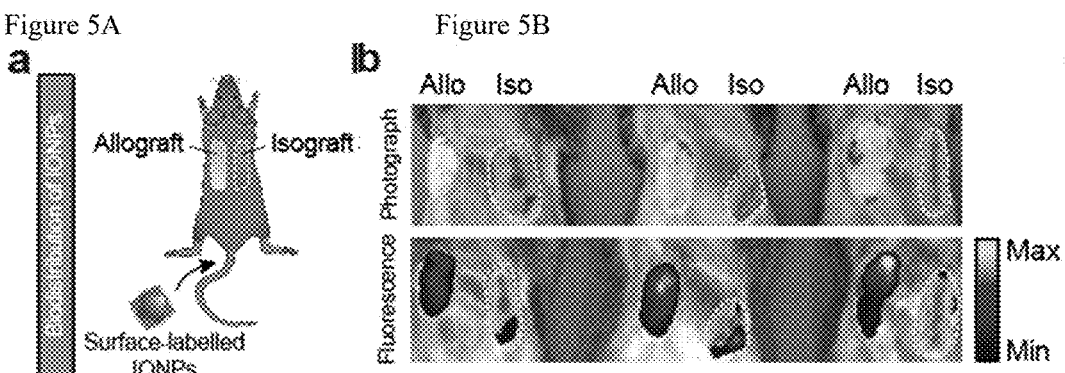
Figure 5C
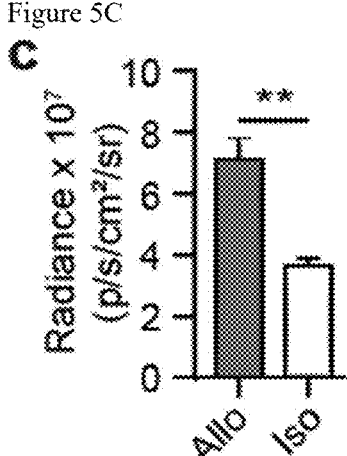

Figure 5D
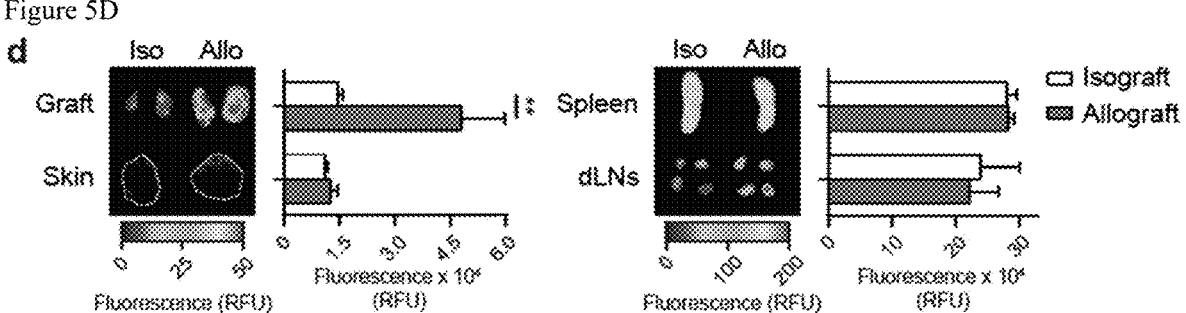
Figure 5E
Figure 5F
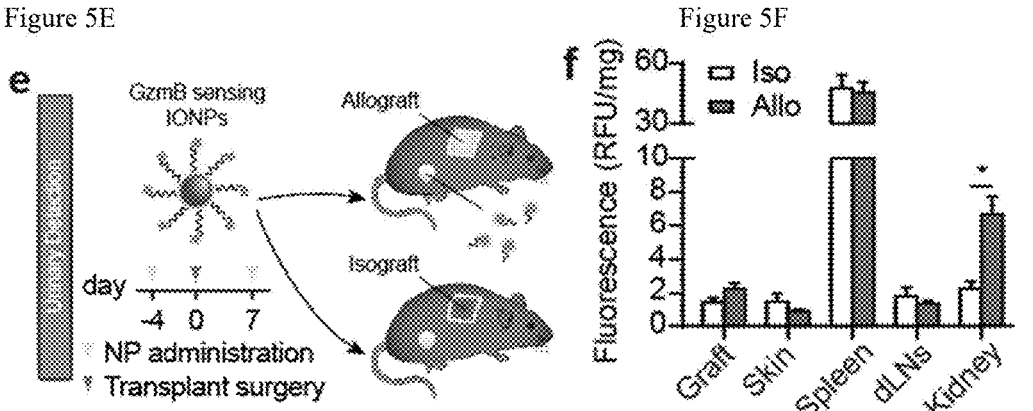
Figure 5G
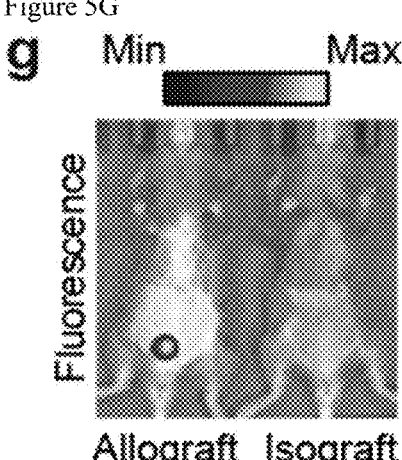

Figure 12
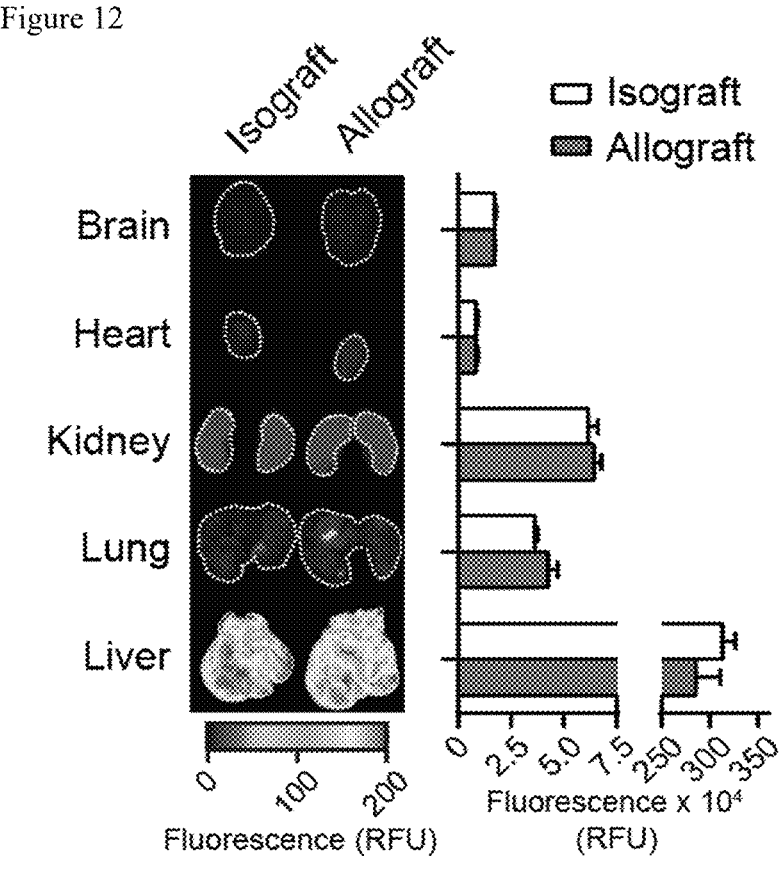
Figure 13A
Figure 13B
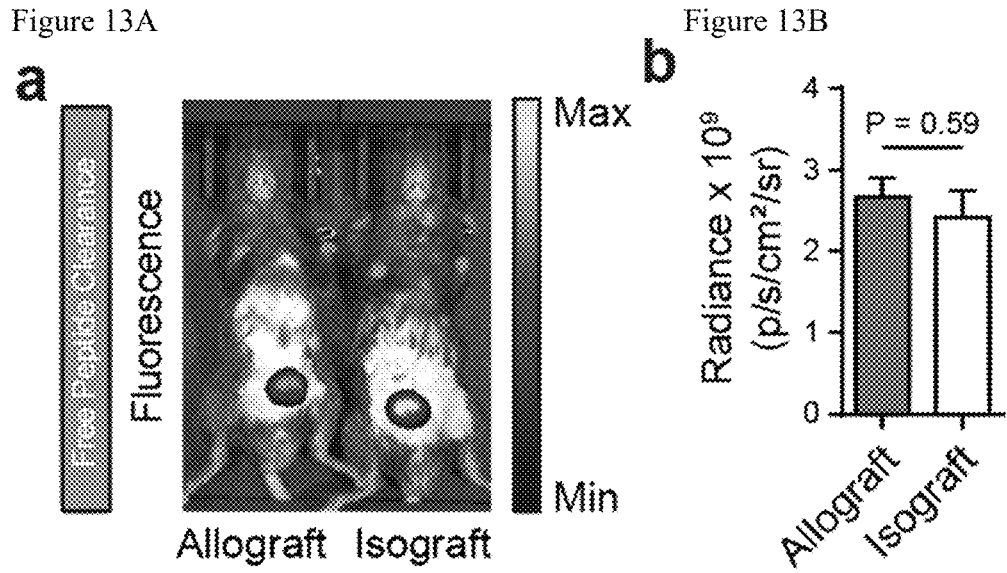

Figure 13C
Figure 13D
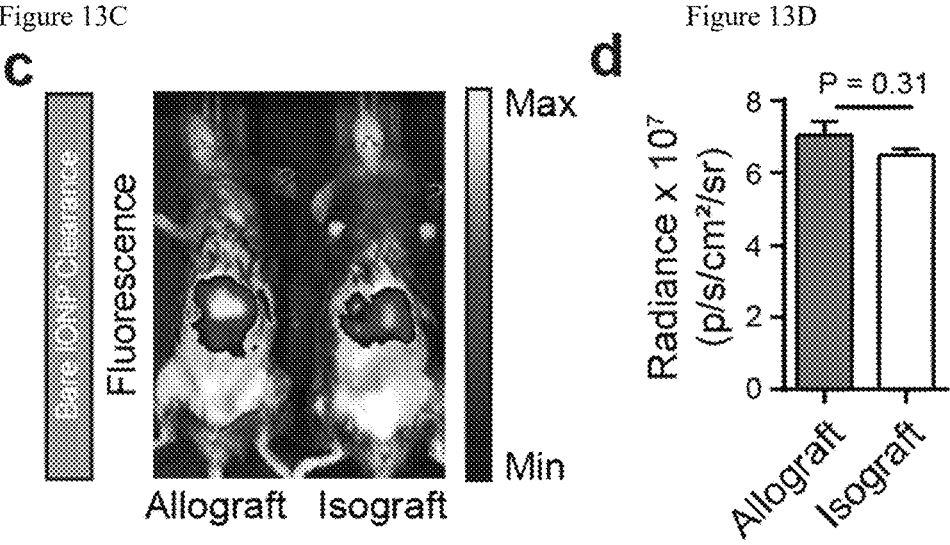
Figure 14A
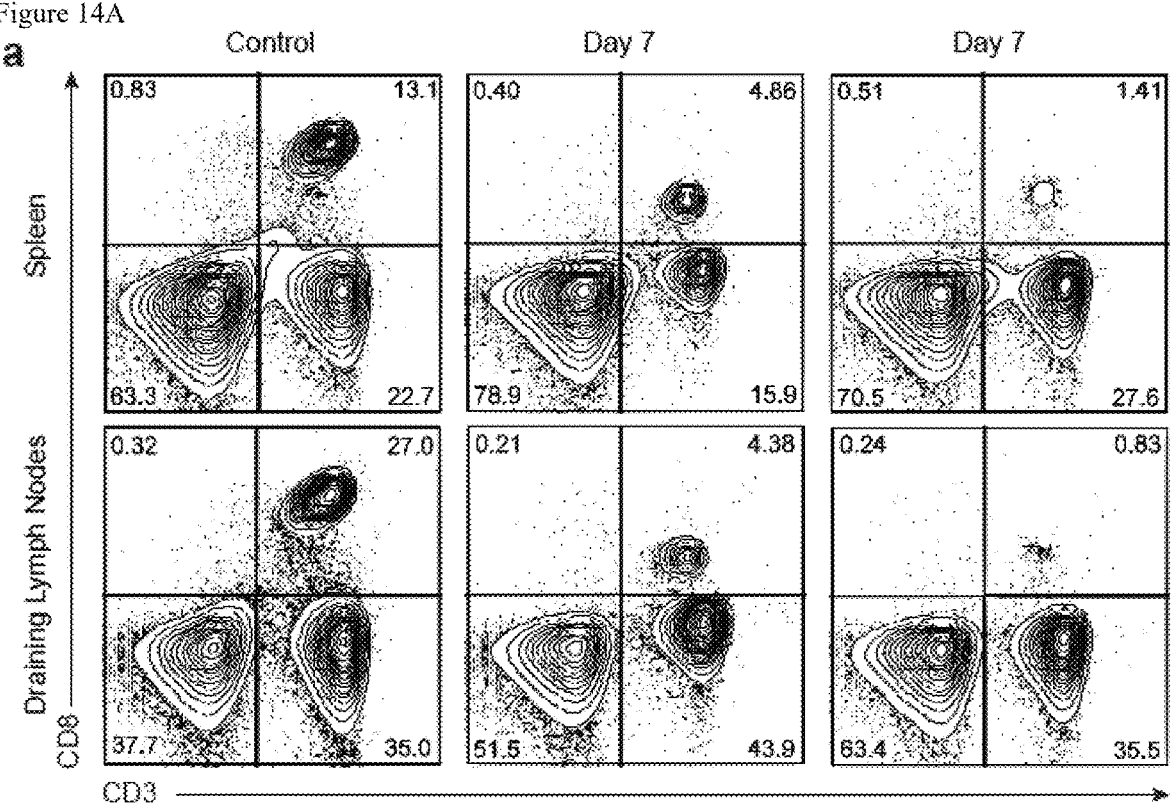

SEQUENCE LISTING

```
<160> NUMBER OF SEQ ID NOS: 148

<210> SEQ ID NO 1
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Ile Gly Gly His Glu Val Lys Pro His Ser Arg Pro Tyr Met Ala
1               5                   10                  15

Leu Leu Ser Ile Lys Asp Gln Gln Pro Glu Ala Ile Cys Gly Phe Leu
            20                  25                  30

Ile Arg Glu Asp Phe Val Leu Thr Ala Ala His Cys Glu Gly Ser Ile
        35                  40                  45

Ile Asn Val Thr Leu Gly Ala His Asn Ile Lys Glu Gln Glu Lys Thr
    50                  55                  60

Gln Gln Val Ile Pro Met Val Lys Cys Ile Pro His Pro Asp Tyr Asn
65                  70                  75                  80

Pro Lys Thr Phe Ser Asn Asp Ile Met Leu Leu Lys Leu Lys Ser Lys
                85                  90                  95

Ala Lys Arg Thr Arg Ala Val Arg Pro Leu Asn Leu Pro Arg Arg Asn
            100                 105                 110

Val Asn Val Lys Pro Gly Asp Val Cys Tyr Val Ala Gly Trp Gly Arg
            115                 120                 125

Met Ala Pro Met Gly Lys Tyr Ser Asn Thr Leu Gln Glu Val Glu Leu
    130                 135                 140

Thr Val Gln Lys Asp Arg Glu Cys Glu Ser Tyr Phe Lys Asn Arg Tyr
145                 150                 155                 160

Asn Lys Thr Asn Gln Ile Cys Ala Gly Asp Pro Lys Thr Lys Arg Ala
                165                 170                 175

Ser Phe Arg Gly Asp Ser Gly Gly Pro Leu Val Cys Lys Lys Val Ala
            180                 185                 190

Ala Gly Ile Val Ser Tyr Gly Tyr Lys Asp Gly Ser Pro Pro Arg Ala
            195                 200                 205

Phe Thr Lys Val Ser Ser Phe Leu Ser Trp Ile Lys Lys Thr Met Lys
    210                 215                 220

Ser Ser
225

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Ala Ile Glu Pro Asp Gly Ser Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Gly Ile Glu Pro Asp Ser Gly Gly Ser Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Ser Lys Ile Glu Phe Asp Phe Gly Val Lys Lys Cys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ile Glu Pro Asp Ser Gly Cys
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ile Glu Pro Asp Gly Ser Ser Lys Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ile Glu Pro Asp Ser Gly Ser Lys Cys
1               5                   10

<210> SEQ ID NO 8
<211> LENGTH: 12
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 8

Ala Lys Ser Ile Glu Pro Asp Gly Ser Ser Lys Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Lys Ser Ile Glu Pro Asp Ser Gly Ser Lys Cys
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ile Glu Phe Asp Gly Ser Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Glu Phe Asp Ser Gly Cys
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ile Glu Phe Asp Ser Gly Ser Lys Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Lys Ser Ile Glu Phe Asp Ser Gly Ser Lys Cys
1               5                   10

-continued

```
<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ile Glu Phe Asp Ser Gly Val Ser Lys Cys
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 15

Ala Ile Glu Pro Asp Gly Ser Cys
1               5

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (11)..(12)
<223> OTHER INFORMATION: D-amino acid

<400> SEQUENCE: 16

Ala Ser Gly Ile Glu Pro Asp Ser Gly Gly Ser Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-amino acid
<220> FEATURE:
<221> NAME/KEY: MOD_RES
<222> LOCATION: (13)..(14)
<223> OTHER INFORMATION: D-amino acid

<400> SEQUENCE: 17

Ala Lys Ser Lys Ile Glu Phe Asp Phe Gly Val Lys Lys Cys
1               5                   10

<210> SEQ ID NO 18
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 18

Ala Ile Glu Pro Asp Ser Gly Cys
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(10)
<223> OTHER INFORMATION: D-amino acid

<400> SEQUENCE: 19

Ala Ile Glu Pro Asp Gly Ser Ser Lys Cys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(10)
<223> OTHER INFORMATION: D-amino acid

<400> SEQUENCE: 20

Ala Ile Glu Pro Asp Ser Gly Ser Lys Cys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 21

Ala Lys Ser Ile Glu Pro Asp Gly Ser Ser Lys Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
           peptide
<220> FEATURE:
<221> NAME/KEY: MOD_RES
<222> LOCATION: (2)..(3)
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 22

Ala Lys Ser Ile Glu Pro Asp Ser Gly Ser Lys Cys
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
           peptide
<220> FEATURE:
<221> NAME/KEY: MOD_RES
<222> LOCATION: (8)..(8)
<223> OTHER INFORMATION: D-amino acid

<400> SEQUENCE: 23

Ala Ile Glu Phe Asp Gly Ser Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
           peptide
<220> FEATURE:
<221> NAME/KEY: MOD_RES
<222> LOCATION: (8)..(8)
<223> OTHER INFORMATION: D-amino acid

<400> SEQUENCE: 24

Ala Ile Glu Phe Asp Ser Gly Cys
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
           peptide
<220> FEATURE:
<221> NAME/KEY: MOD_RES
<222> LOCATION: (8)..(10)
<223> OTHER INFORMATION: D-amino acid

<400> SEQUENCE: 25

Ala Ile Glu Phe Asp Ser Gly Ser Lys Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
           peptide
<220> FEATURE:
<221> NAME/KEY: MOD_RES
```

```
<222> LOCATION: (2)..(3)
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 26

Ala Lys Ser Ile Glu Phe Asp Ser Gly Ser Lys Cys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(11)
<223> OTHER INFORMATION: D-amino acid

<400> SEQUENCE: 27

Ala Ile Glu Phe Asp Ser Gly Val Ser Lys Cys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Val Asn Asp Asn Glu Glu Gly Phe Phe Ser Ala Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid

<400> SEQUENCE: 29

Glu Gly Val Asn Asp Asn Glu Glu Gly Phe Phe Ser Ala Arg
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Ala Ile Glu Pro Asp Gly Ser Cys
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ser Gly Ile Glu Pro Asp Ser Gly Gly Ser Cys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Lys Ser Lys Ile Glu Phe Asp Phe Gly Val Lys Lys Cys
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ile Glu Pro Asp Ser Gly Cys
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ile Glu Pro Asp Gly Ser Ser Lys Cys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ile Glu Pro Asp Ser Gly Ser Lys Cys
1               5                   10

<210> SEQ ID NO 36
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 36

Ala Lys Ser Ile Glu Pro Asp Gly Ser Ser Lys Cys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Lys Ser Ile Glu Pro Asp Ser Gly Ser Lys Cys
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ile Glu Phe Asp Gly Ser Cys
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ile Glu Phe Asp Ser Gly Cys
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Glu Phe Asp Ser Gly Ser Lys Cys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Lys Ser Ile Glu Phe Asp Ser Gly Ser Lys Cys
1               5                   10
```

-continued

```
<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ile Glu Phe Asp Ser Gly Val Ser Lys Cys
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 43

Ala Ile Glu Pro Asp Gly Ser Cys
1               5

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid
<220> FEATURE:
<221> NAME/KEY: MOD_RES
<222> LOCATION: (11)..(12)
<223> OTHER INFORMATION: D-amino acid

<400> SEQUENCE: 44

Ala Ser Gly Ile Glu Pro Asp Ser Gly Gly Ser Cys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: D-amino acid
<220> FEATURE:
<221> NAME/KEY: MOD_RES
<222> LOCATION: (13)..(14)
<223> OTHER INFORMATION: D-amino acid

<400> SEQUENCE: 45

Ala Lys Ser Lys Ile Glu Phe Asp Phe Gly Val Lys Lys Cys
```

-continued

```
1               5                  10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 46

Ala Ile Glu Pro Asp Ser Gly Cys
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(10)
<223> OTHER INFORMATION: D-amino acid

<400> SEQUENCE: 47

Ala Ile Glu Pro Asp Gly Ser Ser Lys Cys
1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(10)
<223> OTHER INFORMATION: D-amino acid

<400> SEQUENCE: 48

Ala Ile Glu Pro Asp Ser Gly Ser Lys Cys
1               5                  10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
```

-continued

```
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 49

Ala Lys Ser Ile Glu Pro Asp Gly Ser Ser Lys Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 50

Ala Lys Ser Ile Glu Pro Asp Ser Gly Ser Lys Cys
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 51

Ala Ile Glu Phe Asp Gly Ser Cys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 52

Ala Ile Glu Phe Asp Ser Gly Cys
1               5

<210> SEQ ID NO 53
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (8)..(10)
<223> OTHER INFORMATION: D-amino acid

<400> SEQUENCE: 53

Ala Ile Glu Phe Asp Ser Gly Ser Lys Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: D-amino acid
<220> FEATURE:
<221> NAME/KEY: MOD_RES
<222> LOCATION: (10)..(12)
<223> OTHER INFORMATION: D-amino acid

<400> SEQUENCE: 54

Ala Lys Ser Ile Glu Phe Asp Ser Gly Ser Lys Cys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (9)..(11)
<223> OTHER INFORMATION: D-amino acid

<400> SEQUENCE: 55

Ala Ile Glu Phe Asp Ser Gly Val Ser Lys Cys
1               5                   10

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Gly Val Asn Asp Asn Glu Glu Gly Phe Phe Ser Ala Arg Lys Ala
1               5                   10                  15

Ile Glu Pro Asp Gly Ser Cys
```

```
        20

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Gly Val Asn Asp Asn Glu Glu Gly Phe Phe Ser Ala Arg Lys Ala
1               5                   10                  15

Ser Gly Ile Glu Pro Asp Ser Gly Gly Ser Cys
            20                  25

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Gly Val Asn Asp Asn Glu Glu Gly Phe Phe Ser Ala Arg Lys Ala
1               5                   10                  15

Lys Ser Lys Ile Glu Phe Asp Phe Gly Val Lys Lys Cys
            20                  25

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Gly Val Asn Asp Asn Glu Glu Gly Phe Phe Ser Ala Arg Lys Ala
1               5                   10                  15

Ile Glu Pro Asp Ser Gly Cys
            20

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Gly Val Asn Asp Asn Glu Glu Gly Phe Phe Ser Ala Arg Lys Ala
1               5                   10                  15

Ile Glu Pro Asp Gly Ser Ser Lys Cys
            20                  25

<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Glu Gly Val Asn Asp Asn Glu Glu Gly Phe Phe Ser Ala Arg Lys Ala
1               5                   10                  15

Ile Glu Pro Asp Ser Gly Ser Lys Cys
            20                  25

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Gly Val Asn Asp Asn Glu Glu Gly Phe Phe Ser Ala Arg Lys Ala
1               5                   10                  15

Lys Ser Ile Glu Pro Asp Gly Ser Ser Lys Cys
            20                  25

<210> SEQ ID NO 63
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Gly Val Asn Asp Asn Glu Glu Gly Phe Phe Ser Ala Arg Lys Ala
1               5                   10                  15

Lys Ser Ile Glu Pro Asp Ser Gly Ser Lys Cys
            20                  25

<210> SEQ ID NO 64
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Gly Val Asn Asp Asn Glu Glu Gly Phe Phe Ser Ala Arg Lys Ala
1               5                   10                  15

Ile Glu Phe Asp Gly Ser Cys
            20

<210> SEQ ID NO 65
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Gly Val Asn Asp Asn Glu Glu Gly Phe Phe Ser Ala Arg Lys Ala
1               5                   10                  15

Ile Glu Phe Asp Ser Gly Cys
            20

<210> SEQ ID NO 66
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Gly Val Asn Asp Asn Glu Glu Gly Phe Phe Ser Ala Arg Lys Ala
1               5                   10                  15

Ile Glu Phe Asp Ser Gly Ser Lys Cys
            20                  25

<210> SEQ ID NO 67
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Gly Val Asn Asp Asn Glu Glu Gly Phe Phe Ser Ala Arg Lys Ala
1               5                   10                  15

Lys Ser Ile Glu Phe Asp Ser Gly Ser Lys Cys
            20                  25

<210> SEQ ID NO 68
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Gly Val Asn Asp Asn Glu Glu Gly Phe Phe Ser Ala Arg Lys Ala
1               5                   10                  15

Ile Glu Phe Asp Ser Gly Val Ser Lys Cys
            20                  25

<210> SEQ ID NO 69
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(23)
<223> OTHER INFORMATION: D-amino acid

<400> SEQUENCE: 69
```

```
Glu Gly Val Asn Asp Asn Glu Glu Gly Phe Phe Ser Ala Arg Lys Ala
1               5                   10                  15

Ile Glu Pro Asp Gly Ser Cys
            20

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(17)
<223> OTHER INFORMATION: D-amino acid
<220> FEATURE:
<221> NAME/KEY: MOD_RES
<222> LOCATION: (26)..(27)
<223> OTHER INFORMATION: D-amino acid

<400> SEQUENCE: 70

Glu Gly Val Asn Asp Asn Glu Glu Gly Phe Phe Ser Ala Arg Lys Ala
1               5                   10                  15

Ser Gly Ile Glu Pro Asp Ser Gly Gly Ser Cys
            20                  25

<210> SEQ ID NO 71
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(18)
<223> OTHER INFORMATION: D-amino acid
<220> FEATURE:
<221> NAME/KEY: MOD_RES
<222> LOCATION: (28)..(29)
<223> OTHER INFORMATION: D-amino acid

<400> SEQUENCE: 71

Glu Gly Val Asn Asp Asn Glu Glu Gly Phe Phe Ser Ala Arg Lys Ala
1               5                   10                  15

Lys Ser Lys Ile Glu Phe Asp Phe Gly Val Lys Lys Cys
            20                  25
```

<210> SEQ ID NO 72
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(23)
<223> OTHER INFORMATION: D-amino acid

<400> SEQUENCE: 72

Glu Gly Val Asn Asp Asn Glu Glu Gly Phe Phe Ser Ala Arg Lys Ala
1               5                   10                  15

Ile Glu Pro Asp Ser Gly Cys
            20

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(25)
<223> OTHER INFORMATION: D-amino acid

<400> SEQUENCE: 73

Glu Gly Val Asn Asp Asn Glu Glu Gly Phe Phe Ser Ala Arg Lys Ala
1               5                   10                  15

Ile Glu Pro Asp Gly Ser Ser Lys Cys
            20                  25

<210> SEQ ID NO 74
<211> LENGTH: 25
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(25)
<223> OTHER INFORMATION: D-amino acid

<400> SEQUENCE: 74

Glu Gly Val Asn Asp Asn Glu Glu Gly Phe Phe Ser Ala Arg Lys Ala
1               5                   10                  15

Ile Glu Pro Asp Ser Gly Ser Lys Cys
            20                  25

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(18)
<223> OTHER INFORMATION: D-amino acid
<220> FEATURE:
<221> NAME/KEY: MOD_RES
<222> LOCATION: (25)..(27)
<223> OTHER INFORMATION: D-amino acid

<400> SEQUENCE: 75

Glu Gly Val Asn Asp Asn Glu Glu Gly Phe Phe Ser Ala Arg Lys Ala
1               5                   10                  15

Lys Ser Ile Glu Pro Asp Gly Ser Ser Lys Cys
            20                  25

<210> SEQ ID NO 76
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(18)
<223> OTHER INFORMATION: D-amino acid
<220> FEATURE:
<221> NAME/KEY: MOD_RES
<222> LOCATION: (25)..(27)
<223> OTHER INFORMATION: D-amino acid

<400> SEQUENCE: 76

Glu Gly Val Asn Asp Asn Glu Glu Gly Phe Phe Ser Ala Arg Lys Ala
1               5                   10                  15

Lys Ser Ile Glu Pro Asp Ser Gly Ser Lys Cys
            20                  25

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(23)
<223> OTHER INFORMATION: D-amino acid

<400> SEQUENCE: 77

Glu Gly Val Asn Asp Asn Glu Glu Gly Phe Phe Ser Ala Arg Lys Ala
1               5                   10                  15

Ile Glu Phe Asp Gly Ser Cys
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
```

```
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(23)
<223> OTHER INFORMATION: D-amino acid

<400> SEQUENCE: 78

Glu Gly Val Asn Asp Asn Glu Glu Gly Phe Phe Ser Ala Arg Lys Ala
1               5                   10                  15

Ile Glu Phe Asp Ser Gly Cys
            20

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (23)..(25)
<223> OTHER INFORMATION: D-amino acid

<400> SEQUENCE: 79

Glu Gly Val Asn Asp Asn Glu Glu Gly Phe Phe Ser Ala Arg Lys Ala
1               5                   10                  15

Ile Glu Phe Asp Ser Gly Ser Lys Cys
            20                  25

<210> SEQ ID NO 80
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
```

```
<223> OTHER INFORMATION: D-amino acid
<220> FEATURE:
<221> NAME/KEY: MOD_RES
<222> LOCATION: (16)..(18)
<223> OTHER INFORMATION: D-amino acid
<220> FEATURE:
<221> NAME/KEY: MOD_RES
<222> LOCATION: (25)..(27)
<223> OTHER INFORMATION: D-amino acid

<400> SEQUENCE: 80

Glu Gly Val Asn Asp Asn Glu Glu Gly Phe Phe Ser Ala Arg Lys Ala
1               5                   10                  15

Lys Ser Ile Glu Phe Asp Ser Gly Ser Lys Cys
            20                  25

<210> SEQ ID NO 81
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(8)
<223> OTHER INFORMATION: D-amino acid
<220> FEATURE:
<221> NAME/KEY: MOD_RES
<222> LOCATION: (10)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (24)..(26)
<223> OTHER INFORMATION: D-amino acid

<400> SEQUENCE: 81

Glu Gly Val Asn Asp Asn Glu Glu Gly Phe Phe Ser Ala Arg Lys Ala
1               5                   10                  15

Ile Glu Phe Asp Ser Gly Val Ser Lys Cys
            20                  25

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ala Pro Val Arg Ser Leu
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Ala Leu Asp Pro Arg Ser Phe
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Thr Gln Asn Lys Ala Ser
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Cys Tyr Leu Asp
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ile Glu Thr Asp Gly Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Leu Glu Val Asp Cys Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Glu Pro Leu Phe Ala Glu Arg Lys
1               5

<210> SEQ ID NO 89
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 89

Ala Met Asn Pro Lys Phe Ala
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Leu Gln Arg Ile Tyr Lys Cys
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Lys Ser Val Ala Arg Thr Leu Leu Val Lys Cys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Glu Glu Lys Gln Arg Ile Ile Gly Cys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Gln Arg Gln Arg Ile Ile Gly Gly Cys
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Leu Gly Arg Gly Gly Ser Cys
1               5
```

```
<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Lys Tyr Leu Gly Arg Ser Tyr Lys Val Cys
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Arg Ala Leu Glu Arg Gly Leu Gln Asp Cys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Ser Leu Gly Arg Lys Ile Gln Ile Cys
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Gly Leu Gln Arg Ala Leu Glu Ile Cys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Lys Val Phe Met Gly Arg Val Tyr Asp Pro Cys
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 100

Ala Ser Ser Thr Gly Arg Asn Gly Phe Lys Cys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Lys Thr Thr Gly Gly Arg Ile Tyr Gly Gly Cys
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Asp Pro Arg Gly Gly Ser Cys
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Val Pro Arg Gly Gly Ser Cys
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Leu Pro Ser Arg Ser Ser Lys Ile Cys
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala His Arg Gly Arg Thr Leu Glu Ile Cys
1               5                   10

<210> SEQ ID NO 106
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 106

Ala Ser Thr Gly Arg Asn Gly Phe Lys Cys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Gln Gln Lys Arg Lys Ile Val Leu Cys
1               5                   10

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Gln Ala Arg Lys Ile Val Leu Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Gln Ala Arg Gly Gly Ser Cys
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ile Pro Glu Asn Phe Phe
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Lys Glu Glu Glu Gly Leu
1               5

```
<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Asn Leu Val Tyr Met Val
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Arg Leu Ala Ala Ile Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Ser Leu Ser Arg Leu Thr
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Pro Leu Gly Val Arg Gly Lys
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Asp Glu Val Asp Asn Lys
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 117

Ala Asp Glu Val Asp Gly Val
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Asp Glu Val Asp Arg Asp
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Asp Glu Val Asp Gly Val
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Leu Glu Val Asp Cys Tyr
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-amino acid

<400> SEQUENCE: 121

Ala Ala Ala Pro Val Cys
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-amino acid
```

```
<400> SEQUENCE: 122

Ala Ala Ala Pro Ala Cys
1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-amino acid

<400> SEQUENCE: 123

Ala Ala Ala Pro Leu Cys
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-amino acid

<400> SEQUENCE: 124

Ala Ala Ala Pro Met Cys
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-amino acid

<400> SEQUENCE: 125

Ala Ala Ala Pro Phe Cys
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-amino acid

<400> SEQUENCE: 126

Gly Gly Phe Pro Arg Ser Gly Gly Gly Cys
1               5                   10

<210> SEQ ID NO 127
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-amino acid

<400> SEQUENCE: 127

Ala Gly Phe Pro Arg Ser Gly Gly Gly Cys
1               5               10

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 128

Ala Ile Lys Phe Phe Ser Ala Cys
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 129

Ala Leu Arg Gln Arg Glu Ser Cys
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 130

Ala Ala Glu Phe Arg His Asp Cys
1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (6)..(6)
<223> OTHER INFORMATION: D-amino acid

<400> SEQUENCE: 131

Ala Ala Ala Pro Phe Cys
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 132

Ala Gln Phe Val Leu Thr Glu Cys
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 133

Ala Arg Glu Thr Tyr Gly Glu Cys
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 134

Ala Ala Thr Val Tyr Val Asp Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 135

Ala Pro Leu Asp Lys Lys Arg Cys
```

-continued 1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-amino acid

<400> SEQUENCE: 136

Ala Asp Lys Val Lys Ala Gln Cys
1               5

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Gly Ser
1

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Ser Gly Gly Gly Ser
1               5

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Gly Ser Gly Gly Gly Ser Gly Gly Gly Ser
1               5                   10

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Gly Gly Gly Gly Gly
1               5

<210> SEQ ID NO 141
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Gly Gly Gly Gly Gly Gly Gly
1               5

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Ala Ala Lys Glu Ala Ala Lys Glu Ala Ala Lys
1               5                   10

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Ala Pro Ala Pro
1               5

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Glu Ala Ala Ala Lys Glu Ala Ala Ala Lys Glu Ala Ala Ala Lys
1               5                   10                  15

<210> SEQ ID NO 145
<211> LENGTH: 8
<212> TYPE: PRT
<213> ORGANISM: Gallus sp.

<400> SEQUENCE: 145

Ser Ile Ile Asn Phe Glu Lys Leu
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Glu Phe Asp Ser Gly
1               5
```

-continued

```
<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Ala Ile Glu Pro Asp Ser Gly Ser Lys Cys
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Lys Ala Ile Glu Phe Asp Ser Gly Val Ser Lys Cys
1               5                   10
```

METHODS AND COMPOSITIONS FOR NONINVASIVE DETECTION OF ORGAN TRANSPLANT REJECTION

CROSS-REFERENCE TO RELATED APPLICATIONS

This application is a continuation of U.S. patent application Ser. No. 16/337,886, filed on Mar. 28, 2019, which is a 371 of International Application No. PCT/US2017/054105, filed on Sep. 28, 2017, which claims priority to U.S. Provisional Application No. 62/400,656, filed on 28 Sep. 2016, each of which is entirely incorporated herein by reference for all purposes.

GOVERNMENT SPONSORSHIP

This invention was made with government support under Grant No. DP2HD091793 awarded by the National Institute of Health and Grant No. 1451512 from the National Science Foundation (DGE-1451512). The government has certain rights in the invention.

SEQUENCE LISTING

The instant application contains a Sequence Listing which has been submitted electronically in ASCII format and is hereby incorporated by reference in its entirety. Said ASCII copy, created on Jun. 20, 2022, is named 61226-714_301_SL.txt and is 47,769 bytes in size.

BACKGROUND OF THE DISCLOSURE

1. Field of the Disclosure

Embodiments of the present disclosure relates generally to methods and compositions for noninvasive detection of transplant rejection, immune conditions related to T cell cytotoxicity (such as for example and not limitation graft versus host disease (GvHD), autoimmune diseases, and immuno-oncology), and sensing T cell cytotoxicity (e.g., to predict treatment efficacy in patients being treated with cancer immune therapies such as checkpoint blockade inhibitors or CAR T cell therapies), and more specifically to compositions comprising scaffolds (such as for example and not limitation, protein scaffolds, polymer scaffolds, and particles (e.g., a microparticle or nanoparticle)) linked to protease-specific detectable peptides that can be administered to transplant recipients and used to detect acute and chronic transplant rejection by cleavage of the composition via the accumulation of the detectable peptides locally at the site of cleavage and/or in a bodily fluid (such as for example and not limitation, urine, lymphatic fluid, blood, plasma, and/or saliva).

2. Background

Organ transplantation remains the single most effective treatment for end-stage organ failure, and early detection of transplant rejection is critical for managing immunosuppression and the long-term survival of recipients (1, 2). During acute cellular rejection (ACR), graft damage is mediated by recipient cytotoxic CD8 T cells that are activated by alloantigens displayed by antigen presenting cells (APC) and target donor cells for killing (3, 4). Although ACR episodes may appear at any time during the life of the graft even years after immunological quiescence (4), ACR can be effectively treated with anti-rejection drugs that target T cells (e.g., thymoglobulin or anti-CD3 antibodies). Therefore, the ability to measure the level of anti-graft T cell responses at an early stage of ACR plays an indispensable role in managing graft health and function (5). Currently, the gold standard for diagnosing ACR is the core tissue biopsy, but this procedure is invasive, subject to sampling error (tissue specimen typically represents ~1/10,000th the volume of the organ), and associated with patient morbidity (6). Noninvasive approaches include measuring biomarkers that indicate organ dysfunction, such as blood urea nitrogen (BUN) and serum creatinine for kidney allografts (7, 8), or biomarkers associated with allograft cell death, such as sequencing cell-free donor-derived DNA from the blood of heart transplant patients (9). These biomarkers indicate graft health at stages that are downstream of cytotoxic T cell activity; noninvasive methods that directly measure anti-graft immune activity as early biomarkers of ACR are needed.

During onset of ACR, recipient cytotoxic T cells kill allograft cells by releasing cytolytic granules containing perforin to permeate target cell membranes and the serine protease granzyme B (GzmB) to induce apoptosis (4, 10). Previous work on histological analysis of allograft tissue sections showed increases in graft-infiltrating CD8 T cells along with elevated expression of GzmA, GzmB and perforin during acute rejection (11, 12). Moreover, in patients with mild ACR and low histological grades, the presence of GzmB-expressing lymphocytes and perforin was predictive of rapid progression to severe ACR (12). Noninvasive approaches to monitor anti-graft lymphocyte activity include work that showed a correlation between RNA transcript levels of GzmB, perforin, and Fas ligand from patient urine to ACR (13, 14). However, the activity of GzmB is highly contextual and dependent on the presence of endogenous inhibitors; for example, previous work showed that higher levels of the serpin protease inhibitor, PI-9, was present in kidney allografts with mild compared to severe ACR (15).

Chronic rejection of transplanted tissue is also an issue in successful organ transplantation. Methods of detecting, diagnosing, and monitoring chronic rejection in transplant recipients are also needed; preferably, such methods are noninvasive. Proteases that are active during chronic rejection include but are not limited to proteases involved in T cell killing (such as for example and not limitation, Granzyme A and Granzyme B), T cell activation (such as for example and not limitation, MALT1, Caspase 8, Calpain 2, and Cathepsin X) (50), apoptosis (such as for example and not limitation, Caspase 3 and Caspase 8), complement activation (such as for example and not limitation, Cls, Clr, MASP2, Factor I, and Factor D) (51), fibrosis (such as for example and not limitation, ADAMTS1, MMP2, and MMP9) (52, 53), and inflammation (such as for example and not limitation, elastase, cathepsin G, PR-3, thrombin, kallikrein 1, kallikrein 6, tryptase, and chymase).

What is needed, therefore, is a composition and method for detecting acute and chronic rejection in transplant recipients, as well as detecting immune conditions related to T cell cytotoxicity (such as for example and not limitation graft versus host disease (GvHD), autoimmune diseases, and immuno-oncology), and sensing T cell cytotoxicity (e.g., to predict treatment efficacy in patients being treated with cancer immune therapies such as checkpoint blockade inhibitors or CAR T cell therapies). The method of detection may take advantage of the nature of the composition, wherein the composition comprises a detectable peptide containing a protease cleavage site linked or coupled to a scaffold, wherein the detectable peptide accumulates locally and/or in a bodily fluid due to the protease being active during acute or chronic rejection. Embodiments of the present disclosure are directed to such compositions and methods.

BRIEF SUMMARY OF THE DISCLOSURE

As specified in the Background Section, there is a great need in the art to identify technologies for detection of transplant rejection, immune conditions related to T cell cytotoxicity (such as for example and not limitation graft versus host disease (GvHD), autoimmune diseases, and immuno-oncology), and sensing T cell cytotoxicity (e.g., to predict treatment efficacy in patients being treated with cancer immune therapies such as checkpoint blockade inhibitors or CAR T cell therapies) and use this understanding to develop novel detection compositions and methods of using such compositions to detect these conditions. Embodiments of the present disclosure relate generally to such methods and compositions and more specifically to compositions that can comprise scaffolds linked to detectable protease-specific peptides that can be administered to transplant recipients and used to detect acute and chronic transplant rejection by cleavage of the composition via the accumulation of the detectable peptide locally at the site of cleavage and/or in a bodily fluid (such as for example and not limitation, urine, lymphatic fluid, blood, plasma, and/or saliva).

In one aspect, the disclosure provides an activity-based nanosensor comprising: a scaffold; a linker coupled to the scaffold; at least one peptide substrate coupled to the linker; and a detectable reporter domain coupled to the at least one peptide substrate.

In some embodiments, the scaffold is selected from the group consisting of a nanoparticle, a nanostructure, a microparticle, a protein, a sugar, a nucleic acid-based scaffold, an imaging contrast agent, and a polymer.

In some embodiments, the scaffold is configured to prevent renal clearance of the substrate.

In other embodiments, the scaffold is a nanoparticle having a diameter from about 3 nm to about 2 microns. In some embodiments, the scaffold is an iron oxide nanoparticle. In some embodiments, the linker comprises a thiol group.

In some embodiments, the linker comprises at least one cysteine residue.

In other embodiments, the at least one peptide substrate comprises a target protease cleavage sequence.

In some embodiments, the at least one peptide substrate comprises at least one amino acid sequence selected from the group consisting of SEQ ID NOs 2-136.

In some embodiments, the target protease is selected from the group consisting of T cell proteases, complement proteases, fibrosis proteases, and inflammation-related proteases.

In some embodiments, the target protease is selected from the group consisting of Granzyme B, Granzyme A, MALT1, Caspase 8, Calpain 2, Cathepsin X, C1s, C1r, MASP2, Factor I, Factor D, ADAMTS1, MMP2, MMP9, elastase, cathepsin G, PR-3, thrombin, kallikrein 1, kallikrein 6, tryptase, and chymase.

In some embodiments, the reporter domain is selected from the group consisting of a fluorophore, a luminescent reporter, a ligand encoded reporter, a mass spectrometry tag, a contrast agent for imaging, a PET-detectable domain, and a nucleic acid tag.

In other embodiments, the reporter domain is a fluorescent reporter.

In some embodiments, the linker is coupled to the scaffold domain via a first spacer.

In other embodiments, the at least one peptide substrate is coupled to the linker via a second spacer.

In still other embodiments, the reporter domain is coupled to the substrate via a third spacer.

In some embodiments, at least one of the first, second, and third spacers comprise a GGS amino acid sequence.

In another aspect, the disclosure provides a method of diagnosing acute organ rejection in a transplant recipient subject comprising:

(a) administering a nanosensor to the subject, the nanosensor comprising: a scaffold; a linker coupled to the scaffold domain; at least one peptide substrate coupled to the linker, the peptide substrate comprising a target protease cleavage sequence; and a detectable reporter coupled to the substrate;

(b) obtaining a sample of a bodily fluid from the subject;

(c) detecting a level of the detectable reporter in the sample of the bodily fluid;

(d) determining an activity of the target protease based on the level of the detectable reporter in the sample of the bodily fluid;

(e) comparing the activity of the target protease in the sample to a reference activity of the target protease;

(f) identifying the subject as:
(i) acutely rejecting the transplant when the activity of the target protease in the sample is greater than the reference activity of the target protease; or
(ii) not acutely rejecting the transplant when the activity of the target protease in the sample is less than the reference activity of the target protease; and (g) optionally treating the acute rejection by administering a therapeutic agent.

In some embodiments, step (a) comprises intravenously administering the nanosensor to the subject.

In other embodiments, the bodily fluid is selected from the group consisting of urine, blood, lymphatic fluid, plasma, and saliva.

In some embodiments, the bodily fluid is urine.

In some embodiments, the reference is selected from the group consisting of a sample taken from the subject before receiving the transplanted tissue and a sample taken from a control subject.

In some embodiments, the therapeutic agent is configured to treat acute organ rejection.

These and other objects, features and advantages of the present disclosure will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below.

(FIG. 2A) Synthetic biomarkers consist of PEG-coated IONPs functionalized with GzmB substrates. In the presence of GzmB, peptide substrates are cleaved and fluorescent reporters are released into solution, increasing sample fluorescence. FIG. 2A discloses SEQ ID NO: 146. (FIG. 2B) Michaelis-Menten analysis of GzmB substrates on nanoparticle surface (n=5, R2=0.79). (FIG. 2C) In vitro protease activity assays showing normalized fluorescence of synthetic biomarker samples after incubation with GzmB or key proteases. (FIG. 2D) Activity assays showing normalized fluorescence of synthetic biomarker samples in mouse plasma upon addition Ca2+to initiate coagulation cascade or addition of GzmB. (FIG. 2E) Activity assays showing normalized fluorescence of synthetic biomarker samples in control serum after addition of heat aggregated gamma globulin (HAGG) to initiate complement cascade or addition of GzmB. (FIG. 2F) ELISA measurements of membrane attack complex (MAC) in activity assay supernatants of synthetic biomarkers with control serum and complement activator (one-way ANOVA with Turkey's post test, n=3).

FIGS. 3A-31. Sensing GzmB during cytotoxic activity of alloreactive T cells. (FIG. 3A) After upregulating expressing, activated CD8 OT1 cells secrete GzmB to mediate apoptosis of EG7-OVA target cells. (FIG. 3B) Flow cytometry plots of GzmB activity within EG7-OVA and EL4 target cells after co-cultured with OT1 T cells. (FIG. 3C) Quantified plot of flow analysis showing percent of EG7-OVA and EL4 cells having intracellular GzmB activity. (FIG. 3D) ELISA assay measuring levels of GzmB in co-culture supernatants of OT1 T cells with EG7-OVA or EL4 target cells at different ratios of T cells to target cells (one-way ANOVA and Turkey's post test, n=3; nd=not detected). (FIG. 31) T cell activity assays showing normalized fluorescence of synthetic biomarkers in co-culture supernatants of T cells isolated from skin graft mice with target cells from BALB/c donor mice.

FIGS. 4A-4G. Granzyme B is upregulated at the onset of acute cellular rejection. (FIG. 4A) Schematic of skin graft mouse model of acute allograft rejection. (FIG. 4B) Pictures of skin grafts showing morphological features of rejection that begin to appear on day 9 post-transplant. (FIG. 4C) Skin graft scores showing graft quality between allo- and iso-grafts (two-way ANOVA and Sidak's post test, n=8) (FIG. 4D) Immunohistochemistry staining of GzmB in graft and healthy skin tissues from mice bearing allo- or iso-grafts. (FIG. 4E) Quantified plot of IHC data showing percent of GzmB staining in graft and skin tissues (two-way ANOVA and Sidak's post test, n=4-6 fields of view). (FIG. 4F) ELISA measurements of GzmB in plasma of skin graft mice during the course of rejection (two-way ANOVA and Sidak's post test, n=4). LOD=limit of detection, defined by $A_{blank}+3$ $SD_{blank}$. (FIG. 4G) Flow analysis of GzmB and CD44 expression in CD8+T cells isolated from the spleens and draining lymph nodes of mice bearing allo- or iso-grafts on days 5, 7, and 9 post-transplant.

FIGS. 5A-51. Urine analysis discriminates acute cellular rejection with high sensitivity and specificity. (FIG. 5A) Mice bearing both allo- and iso-grafts on the same animal are given surface-labelled synthetic biomarkers for biodistribution studies. (FIG. 5B) Top, photograph of mice bearing both skin grafts. Bottom, near infrared fluorescent images showing synthetic biomarkers accumulation in skin grafts. (FIG. 5C) Quantified fluorescent signals of skin allo- and iso-grafts from mice bearing both grafts on the same animal (one way ANOVA and Turkey's post test, n=3). (FIG. 5D) Whole organ fluorescent images and quantified fluorescent signals showing biodistribution of synthetic biomarkers in graft, skin, spleen, and draining lymph nodes of skin graft mice (two way ANOVA and Sidak's post test, n=3). (FIG. 5E) Timeline of urinalysis study. Mice bearing either skin allografts or isografts are administered synthetic biomarkers 4 days before and 7 days after transplant surgeries. (FIG. 5F) Fluorescent signals of homogenized tissue samples from skin graft mice after administration of synthetic biomarkers showing elevated signal in kidneys of allograft mice (Student's t-test, n=4-6). (FIG. 5G) Whole mouse fluorescent image after administration of GSBs showing strong signal from the bladders of mice bearing allografts. (FIG. 51) Receiver-operating-characteristic (ROC) analysis showing that synthetic biomarkers can differentiate between accepting isografts and rejecting allografts in skin graft mice (AUC=0.969, 95% CI=0.892-1.045).

FIG. 6. Optimization of GzmB peptide substrate. Initial cleavage velocities of 13 GzmB-sensing synthetic biomarkers with recombinant GzmB. Lowercase letters are d-form amino acids. Sequence AIEFDSGc (SEQ ID NO: 24) was chosen due to high rate of cleavage and its specificity for GzmB. (n=3-8 independent assays; nd=not detected).

FIGS. 7A-7B. In vitro characterization of synthetic biomarkers. (FIG. 7A) Dynamic light scattering (DLS) analysis showing size distribution of synthetic biomarkers in PBS or mouse plasma. (FIG. 7B) Pharmacokinetic studies showing circulation half-life of synthetic biomarkers in control Swiss Webster mice (n=4, R2=0.86).

(FIG. 8B) Flow cytometry staining of intracellular GzmB and T cell activation marker CD44 in CD8 T cells after coculturing activated OT1 T cells with EG7-OVA target cells or EL4 control cells.

FIG. 9. Morphology of skin allografts and isografts during the course of rejection. Photographs of skin allografts and isografts on days 7, 9, 11, and 13 post-transplant. Signs of rejection began to appear in allografts at around day 9.

FIGS. 10A-10B. Upregulation of CD8-expressing cells in skin allografts. (FIG. 10A) Immunohistochemistry staining of GzmB in graft and healthy skin tissues from mice bearing allo- or iso-grafts. (FIG. 10B) Quantified plot of IHC data showing percent of CD8 staining (two-way ANOVA and Sidak's post test, n=3-6 fields of view).

FIG. 11. Passive accumulation of synthetic biomarkers in skin allografts. Top panel, photograph of excised allografts, isografts, and healthy skin from mice bearing both grafts on the same animal. Bottom panel, near infra-red fluorescent image showing biodistribution of synthetic biomarkers in these tissue samples.

FIG. 12. Biodistribution of synthetic biomarkers in major organs of skin graft mice. Near infra-red fluorescent image and quantified signals showing biodistribution of synthetic biomarkers in brain, heart, kidney, lung, and liver of mice bearing either allo- or iso-graft (two-way ANOVA and Sidak's post test, n=3).

FIGS. 13A-13D. Urine pharmacokinetics of free peptide and bare nanoparticles. (FIG. 13A) Fluorescent image showing clearance of free peptides in bladders of skin graft mice. (FIG. 13B) Quantified bladder fluorescent signals after administration of labelled free peptides (one way ANOVA and Turkey's post test, n=3) (FIG. 13C) Fluorescent image showing clearance of bare nanoparticles in bladders of skin graft mice. (FIG. 13D) Quantified bladder fluorescent signals after administration of surface-labelled nanoparticles (one way ANOVA and Turkey's post test, n=2).

FIGS. 14A-14B. Depletion of CD8 T cells before and after transplant surgeries. (FIG. 14A) Flow cytometry analysis showing that CD8 depletion reduces the population of CD3+CD8+ cells in secondary lymphoid organs right before and after skin graft surgeries. (FIG. 14B) Quantified plot showing significant reduction in percent of CD3+CD8+ T cells in spleens and draining lymph nodes of CD8-depleted mice versus. Control mice (n=2-3).

DETAILED DESCRIPTION OF THE DISCLOSURE

Figure 1:
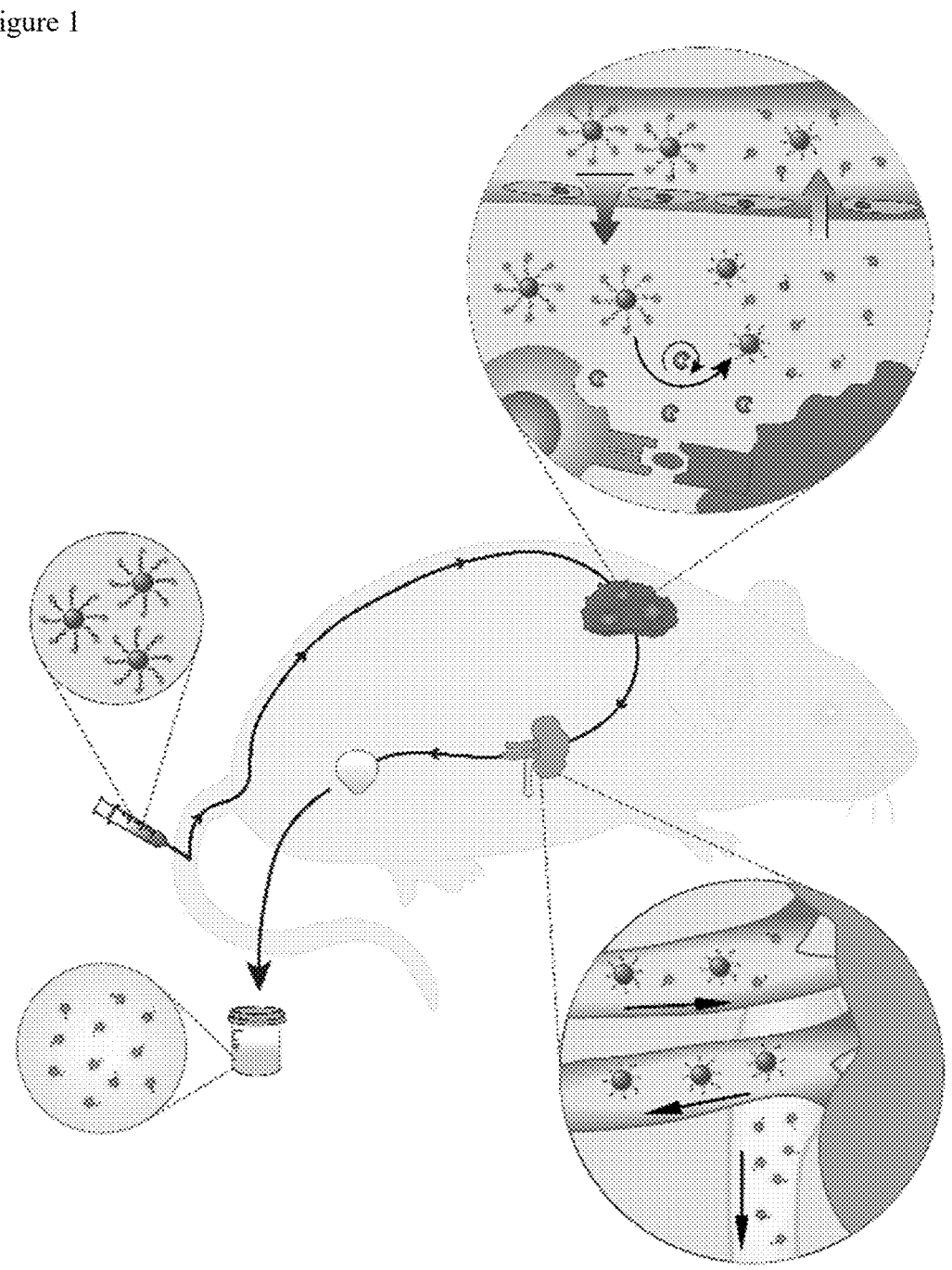
FIG. 1. Granzyme B sensing synthetic biomarkers detect onset of acute allograft rejection by amplifying detection signals into urine. Nanoparticles coated with GzmB substrates are intravenously administered and accumulate in allograft tissues. Within this local microenvironment, GzmB secreted by alloreactive CD8 T cells cleaves the peptide substrates on nanoparticle surface, which triggers the pharmacokinetic switch and release of fluorescent reporters into urine. Urinary signals are quantified as early stage biomarkers of acute cellular rejection.

As specified in the Background Section, there is a great need in the art to identify technologies for detection of transplant rejection, immune conditions related to T cell cytotoxicity (such as for example and not limitation graft versus host disease (GvHD), autoimmune diseases, and immuno-oncology), and sensing T cell cytotoxicity (e.g., to predict treatment efficacy in patients being treated with cancer immune therapies such as checkpoint blockade inhibitors or CAR T cell therapies) and use this understanding to develop novel detection compositions and methods of using such compositions to detect these conditions The present disclosure satisfies this and other needs. Embodiments of the present disclosure relate generally to such methods and compositions and more specifically to compositions comprising scaffolds linked to detectable protease-specific peptides that can be administered to transplant recipients and used to detect acute and chronic transplant rejection by cleavage of the composition via the accumulation of the detectable peptides in a bodily fluid (such as for example and not limitation, urine, lymphatic fluid, blood, plasma, and/or saliva), locally at the site of cleavage, and/or downstream lymph nodes.

Detecting the onset of transplant rejection is critical for the long-term health and survival of the organ recipient, yet the core biopsy remains the diagnostic gold standard despite its invasiveness, risk of morbidity, and limited predictive power. For example, during acute cellular rejection (ACR), host CD8 T cells damage allograft tissue by releasing the protease granzyme B (GzmB) to trigger donor cell death. To develop a noninvasive biomarker of early ACR, the inventors engineered activity-based nanoprobes to sense a target protease activity, e.g., GzmB, inside the body by producing an amplified signal in host bodily fluid, e.g., urine, for detection. These synthetic biomarkers can comprise target protease peptide substrates conjugated to nanoparticles, preferentially accumulate in allografts and secondary lymphoid organs, and are activated during antigen-specific T cell killing. For example, in a skin graft mouse model of transplant rejection, systemic administration of synthetic biomarkers significantly elevate urine signals at the onset of ACR before features of rejection appear in graft tissue. This is a non-limiting example of a noninvasive approach and may allow routine monitoring of allograft immune health without the risk of a biopsy.

Therefore, as a non-limiting example, the inventors sought to develop a noninvasive diagnostic assay to measure the activity of GzmB within allograft tissue as an early biomarker of ACR. This assay can enable detection of ACR before tissue damage begins, and thus can provide a way to detect ACR before a biopsy of the transplanted tissue would indicate ACR. This assay can also enable monitoring of ACR over time, as compositions comprising the activity-based nanosensor may be administered repeatedly over a desired timeframe to a transplant recipient, and the diagnostic assay repeated after each administration.

Herein is described an activity-based nanosensor that can be administered intravenously (i.v.) to the recipient and can be, for example, engineered to detect elevations in GzmB activity by shedding a reporter into host urine as a noninvasive biomarker of early ACR. The present protease-sensing synthetic biomarkers leverage enzyme turnover to locally amplify detection signals, but by contrast, these signals are further enriched from blood into other bodily fluids, for example, urine, by renal filtration. Alternatively, these biomarkers can enable local detection of protease activity (e.g., by imaging), and/or detection in a downstream lymph node. These mechanisms for signal amplification can allow synthetic biomarkers to be ultrasensitive for early stage disease (17-21). In skin graft mouse models of ACR, synthetic biomarkers accumulate in allografts and in secondary lymphoid organs to produce significantly elevated urine signals in mice bearing allografts at the onset of ACR. These protease-sensing synthetic biomarkers are noninvasive, predictive, and interact directly with host immune responses against allografts to produce amplified detection signals in urine.

The compositions of the invention can comprise detectable peptide sequences (also referred to herein as peptide substrates and/or detectable peptide substrates) that can comprise protease recognition/cleavage sites linked/coupled to scaffolds (such as for example and not limitation, protein scaffolds, polymer scaffolds, and particles (e.g., a microparticle or nanoparticle)) (e.g., activity-based nanosensors), wherein the peptide-scaffold conjugate can be capable of detecting protease activity in vivo and allowing noninvasive detection and/or monitoring of physiological processes. The detectable peptide sequences can be released at the site of cleavage, which can produce a localized signal (which can be detected at the cleavage site), and can accumulate in draining lymph nodes, blood, urine, and other bodily fluids where they can be detected (e.g., by methods as described in US20140303014 and US2014/0363833, each of which is incorporated herein by reference).

Definitions

To facilitate an understanding of the principles and features of the various embodiments of the disclosure, various illustrative embodiments are explained below. Although exemplary embodiments of the disclosure are explained in detail, it is to be understood that other embodiments are contemplated. Accordingly, it is not intended that the disclosure is limited in its scope to the details of construction and arrangement of components set forth in the following description or examples. The disclosure is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or." it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to +20%, preferably up to +10%, more preferably up to +5%, and more preferably still up to #1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present disclosure are intended to be illustrative and not restrictive. Many suitable materials that would perform the same or a similar function as the materials described herein are intended to be embraced within the scope of the disclosure. Such other materials not described herein can include, but are not limited to, materials that are developed after the time of the development of the disclosure, for example. Any dimensions listed in the various drawings are for illustrative purposes only and are not intended to be limiting. Other dimensions and proportions are contemplated and intended to be included within the scope of the disclosure.

As used herein, the term "subject" or "patient" refers to mammals and includes, without limitation, human and veterinary animals. In a preferred embodiment, the subject is human.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein the term "therapeutically effective" applied to dose or amount refers to that quantity of a compound or pharmaceutical composition that when administered to a subject for treating (e.g., preventing or ameliorating) a state, disorder or condition, is sufficient to effect such treatment. The "therapeutically effective amount" will vary depending on the compound or bacteria or analogues administered as well as the disease and its severity and the age, weight, physical condition and responsiveness of the mammal to be treated.

As used herein, the term "combination" of a composition according to the present disclosure and at least a second pharmaceutically active ingredient means at least two, but any desired combination of compounds can be delivered simultaneously or sequentially (e.g., within a 24 hour period).

Within the meaning of the present disclosure, the term "conjoint administration" is used to refer to administration of a composition according to the disclosure and another therapeutic agent simultaneously in one composition, or simultaneously in different compositions, or sequentially (preferably, within a 24 hour period).

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S.

Pharmacopeia or other generally recognized pharmacopeia for use in mammals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a Suitable pharmaceutical carriers are described in "*Remington's* flavorant, and a colorant. Pharmaceutical Sciences" by E. W. Martin.

The term "a control level" as used herein encompasses predetermined standards (e.g., a published value in a reference) as well as levels determined experimentally in similarly processed samples from control subjects (e.g., BMI-, age-, and gender-matched subjects without asthma as determined by standard examination and diagnostic methods) and/or from the subject prior to undergoing transplant surger.

In accordance with the present disclosure there may be employed conventional molecular biology, microbiology, and recombinant DNA techniques within the skill of the art. Such techniques are explained fully in the literature. See, e.g., Sambrook, Fritsch & *Maniatis, Molecular Cloning: A*

*Laboratory Manual,* Second Edition (1989) Cold Spring Harbor Laboratory Press, Cold Spring Harbor, New York (herein "Sambrook et al., 1989"); *DNA Cloning: A Practical Approach,* Volumes I and II (D. N. Glover ed. 1985); Oligonucleotide Synthesis (M. J. Gait ed. 1984); Nucleic Acid Hybridization (B. D. Hames & S. J. Higgins eds. (1985); Transcription and Translation (B. *D. Hames & S. J. Higgins, eds.* (1984); *Animal Cell Culture (R. I. Freshney, ed.* (1986); *Immobilized Cells and Enzymes (IRL Press,* (1986); B. Perbal, *A Practical Guide To Molecular Cloning* (1984); F. M. Ausubel et al. (eds.), *Current Protocols in Molecular Biology,* John Wiley & Sons, Inc. (1994); among others.

Compositions and Methods of the Disclosure

The compositions and methods of the disclosure can be used to detect proteolytic activity of proteases associated with immune conditions related to T cell cytotoxicity (e.g., graft versus host disease (GvHD), autoimmune diseases), as well as with both acute and chronic transplant rejection and with T cell cytotoxicity (e.g., to predict treatment efficacy in patients being treated with cancer immune therapies such as checkpoint blockade inhibitors or CAR T cell therapies). These proteases include but are not limited to T cell proteases (such as for example and not limitation, Granzyme B, Granzyme A, MALT1, Caspase 8, Calpain 2, and Cathepsin X), complement proteases (such as for example and not limitation, Cls, Clr, MASP2, Factor I, Factor D), fibrosis proteases (such as for example and not limitation, ADAMTS1, MMP2, MMP9), and inflammatory proteases (such as for example and not limitation, elastase, cathepsin G, PR-3, thrombin, kallikreins 1&6, tryptase, and chymase). These proteases have activities that can allow differentiation between acute (mediated by, e.g., T cell cytotoxicity) from chronic (mediated by, e.g., complement proteases and fibrosis) organ transplant rejection. These proteases are also known to be involved in T cell killing (e.g., Granzyme B, Granzyme A), T cell activation (e.g., MALT1, Caspase 8, Calpain 2, Cathepsin X), apoptosis (e.g., Caspase 3, Caspase 8), complement activation (e.g., Cls, Clr, MASP2, Factor I, Factor D), fibrosis (e.g., ADAMTS1, MMP2, MMP9), and inflammation (e.g., elastase, cathepsin G, PR-3, thrombin, kallikreins 1&6, tryptase, and chymase).

In order to detect proteolytic activity, the compositions of the present disclosure can be designed to contain one or more detectable peptide sequences (also referred to herein as peptide substrates and/or detectable peptide substrates) that are capable of being recognized by the proteases and are also linked or coupled to scaffolds (such as for example and not limitation, protein scaffolds, polymer scaffolds, and particles (e.g., microparticles or nanoparticles)), and the detectable peptide sequences can accumulate in a bodily fluid (such as for example and not limitation, urine, plasma, draining lymph, blood, saliva, etc.) after being cleaved from the peptide-scaffold complex by the protease of interest. The composition can further comprise an optional spacer region located between the one or more detectable peptide sequences and the scaffold and adjacent either side of the linker region.

Also disclosed herein is a conjugate that can comprise one or more peptide sequences operably linked to at least one scaffold, wherein the conjugate can be recognized by a protease as described herein. In some embodiments, the one or more peptide sequences and/or the scaffold of the conjugate can be capable of generating a detectable signal such that the conjugate can be visualized and tracked in real time.

In some embodiments, the one or more detectable peptide sequences can comprise a reporter (also referred to herein as a reporter domain) and a protease cleavage/recognition site.

When the composition or conjugate is exposed to enzymes, for instance, proteases, the at least one detectable peptide sequence can be cleaved, such that the reporter of the detectable peptide sequence is released. The reporter can be detected locally at the site of cleavage (i.e., at the site of the protease activity) or in the subject's blood or plasma (e.g., by ELISA), or can travel to one or more nearby draining lymph nodes and be detected there, or can travel to the kidney and be renally-cleared and detectable in urine. The reporter thus functions as a "messenger" of enzyme activity. In the absence of enzyme activity, the composition or conjugate can remain uncleaved, indicating that the proteases are not active. The reporter includes for example and not limitation, a fluorophore (e.g., for fluorescent detection), a luminescent reporter (e.g., for bioluminescent assays), a ligand encoded reporter (e.g., for detection by ELISA or other antibody detection systems), a mass tag (e.g., for detection by mass spectrometry), and a nucleic acid tag (e.g., for detection by PCR), etc. In some embodiments, the detectable peptide sequence can be detected by a method such as, for example and not limitation, Sanger sequencing, pyrosequencing, SOLID sequencing, massively parallel sequencing, barcoded DNA sequencing, PCR, real-time PCR, quantitative PCR, microarray analysis of the isolated nucleic acid with a gene chip, restriction fragment length polymorphism analysis, allele specific ligation, comparative genomic hybridization, microarray/microchip analysis of the isolated nucleic acid, DNA/RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, bead-based flow-cytometry, immuno-histochemistry, ELISA, RIA, Western blot, immunoaffinity chromatography, HPLC, mass spectrometry, mass spectroscopy, protein microarray/microchip analysis, PAGE analysis, isoelectric focusing, immunoturbidimetry, rapid immunodiffusion, laser nephelometry, visual agglutination, quantitative Western blot analysis, multiple reaction monitoring-mass spectrometry (MRM Proteomics), Lowry assay, Bradford assay, BCA assay, UV spectroscopic assays, fluorescent assays, luminescent assays, and 2-D gel electrophoresis. In some embodiments, the peptide sequences are detected by methods described in any of WO2007/106415, US2010/0240050, US2014/0303014 and US2014/0363833, each of which is incorporated herein by reference.

The scaffold can comprise a protein scaffold (e.g., albumin, IgG, IgG Fc, antibody-based, antibody fragment-based, etc.), a polymer scaffold (e.g., PEG, PLGA), a DNA scaffold (e.g., (DNA origamis), a sugar scaffold (e.g., dextran), imaging (e.g., magnetic resonance imaging) contrast agents (e.g., gadolinium, iron oxide) and a particle (e.g., a microparticle or nanoparticle, such as for example and not limitation, nanostructures including nanofibers, nanorods, nanotubes). In some embodiments, the scaffold is detectable, e.g., by fluorescence, mass spectrometry, magnetic imaging, ELISA, luminescence, etc. The scaffold can have a size ranging from 3 nanometers to 2 micrometers, including from 10 nanometers to 1.5 micrometers, 20 nanometers to 1 micrometer, 50 nanometers to 0.1 micrometer, and 50 nanometers to 150 nanometers. The scaffold can provide the composition with a longer circulation half-life, such as for example and not limitation, by preventing the composition from being trafficked to the lymph and/or being cleared from circulation due to its small size. The circulation half-life of the compositions of the disclosure can be at least 1 hour to 52 weeks, from 2 hours to 36 hours, from 3 hours to 24 hours, and/or 5 hours to 12 hours. The scaffold can be monovalent or polyvalent, meaning that it can be coupled to at least one detectable peptide sequence to 5,000 detectable peptide sequences, including from 50-100 detectable peptide sequences.

As used herein, the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments, the diameter is about 5 nm to about 500 nm. In other embodiments, the diameter is about 100 nm to about 200 nm. In other embodiments, the diameter is about 10 nm to about 100 nm. The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof. The polymers may be biodegradable (such as for example and not limitation, synthetic polymers such as polymers of lactic acid and glycolic acid, polyanhydrides, poly (ortho) esters, polyurethanes, poly (butic acid), poly(valeric acid), poly (caprolactone), poly (hydroxybutyrate), poly (lactide-co-glycolide) and poly (lactide-co-caprolactone), and natural polymers such as alginnate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof), or non-biodegradable (such as for example and not limitation, ethylene vinyl acetate, poly (meth) acrylic acid, polyamides, copolymers and mixtures thereof). The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxy-apatite, tricalcium phosphate, dicalcium phosphate, tricalcium phosphate, tetracalcium phosphate, amorphous calcium phosphate, octacalcium phosphate, and silicates. In certain embodiments, the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

The detectable peptide sequences may be coupled to one or more linkers to aid in joining the one or more peptide sequences to the scaffold. The linker may be any suitable linker for joining peptide sequences to scaffolds. In one embodiment, the linker comprises a small molecule linker SIA to join primary amines on nanoparticle surface to thiols on cysteine-terminated peptides. In another embodiment, the linker comprises small molecule linkers such as for example and not limitation, amine to sulfhydryl linkers (e.g., BMPS, MBS, SMCC, SMPH, SPDP, SBAP), carboxyl to amine linkers (e.g., DCC, EDC, EDAC), and/or sulfhydryl-to-carbohydrate linkers (e.g., BMPH, EMCH, MPBH). In one embodiment, the linker may contain a thiol group, such as for example and not limitation, in a cysteine residue (which may be in D or L form). Suitable linkers are well known to those of skill in the art and include, but are not limited to, straight or branched-chain carbon linkers, heterocyclic carbon linkers, peptide linkers, nucleic acid molecules, polypeptides, lipids, fatty acids, peptide nucleic acids, aptamers, DNA, RNA, leucine zippers, oligonucleotides, oligopeptides, biotin, avidin, streptavidin, haptene antibody bonds or biotin avidin bonds. Linkers can also be derivatives of PEG or other biocompatible polymers of different sizes. The linkers can be capable of forming covalent bonds to amino groups, carboxyl groups, or sulfhydryl groups or hydroxyl groups. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Sulfhydryl-binding linkers include reactive groups such as sulfhydryl groups, acrylates, isothiocyanates, isocyanates and the like. Hydroxyl binding groups include reactive groups such as carboxyl groups, isocyanates, isothiocyanates, esters, haloalkyls, and the like. In certain embodiments, an end of the linker is capable of binding to a crystalline composition formed from a Group IV metal element. The linker may be of any suitable length and can be varied to bring the detectable peptide sequence and the scaffold closer together or farther apart as desired. Exemplary short linkers may be strands of RNA, DNA, short amino acid sequences, polypeptides, fatty acids, proteins, antibodies, or other small molecules. In some embodiments, the detectable peptide sequences are linked/coupled to the at least one scaffold by a thiol group, such as that of a cysteine residue (e.g., a N-terminal and/or C-terminal and/or internal cysteine residue). In other embodiments, the detectable peptide sequences are linked/coupled to the scaffold by a lysine linker or residue (e.g., a N-terminal and/or C-terminal and/or internal lysine linker or residue). In some embodiments, the one or more detectable peptide sequences are operably linked to the at least one scaffold through a linker or chemical linkage comprising at least one bond selected from the group consisting of: a covalent bond, an electrostatic bond and a chelation bond. In some embodiments, the bond is a covalent bond, which can be a bond through a functional group selected from the group consisting of: a hydroxyl, a carboxyl, a carbonyl, a sulfhydryl, an amine, an amide, a nitrile, a nitrogen with a free lone pair of electrons, an amino acid, a thiol, a polyethylene glycol, a sulfonic acid, a sulfonyl halide, and an acyl halide. In some embodiments, the bond is an amide bond formed through reaction of a carboxyl group of the at least one scaffold and an amine group of the one or more detectable peptide sequences. In some embodiments, the bond is a thioether bond formed through a reaction involving the thiol group of a natural or engineered cysteine residue of the one or more detectable peptide sequences. In some embodiments, the one or more peptide sequences are operably linked to at least one scaffold through a linker or chemical linkage comprising at least one chelation bond. The chelation bond can be formed between a metal of the scaffold and a metal-chelating ligand attached to or otherwise associated with the one or more peptide sequences. The metal-chelating ligand can comprise one or more naturally occurring or engineered histidine residues of the one or more detectable peptide sequences. In some embodiments, the metal-chelating ligand comprises a histidine tag fused to the N-terminus or the C-terminus of the one or more peptide sequences. In some embodiments, the one or more detectable peptide sequences are linked to the at least one scaffold by enzymatic linkages, such as for example and not limitation, by a bond formed by a ligase, sortase mediated linkages, HaloTag linkages, SNAP-tag linkages, CLIP-tag linkages, full-length or split intein-mediated linkages, BirA-mediated linkages, Sfp-mediated linkages, and other bioconjugation methods. In some embodiments, the linker is a protein of 10-100 amino acids in length. Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

The compositions of the invention may also comprise at least one optional spacer region located between the one or more detectable peptide sequences and the scaffold. The optional spacer region(s) may be located on either side of the linker, e.g., between the linker and the scaffold and/or between the linker and the one or more detectable peptide sequences. In some embodiments, the spacer region can comprise a GGS amino acid sequence. In other embodiments, the spacer can be a small peptide, such as for example and not limitation, GGS, GGGS (SEQ ID NO: 137), (GGGS)$^2$ (SEQ ID NO: 138), (GGGS)$^3$ (SEQ ID NO: 139), (Gly)$^6$ (SEQ ID NO: 140), (Gly)$^8$ (SEQ ID NO: 141), (EAAK)$^3$ (SEQ ID NO: 142), PAPAP (SEQ ID NO: 143), A (EAAAK)$^3$ (SEQ ID NO: 144). In some embodiments, the linker can comprise primarily D-form amino acids to resist proteolytic cleavage. Spacers can also be derivatives of PEG or other biocompatible polymers of different sizes.

The peptide sequences of the disclosure can include those that can be recognized by proteases associated with immune conditions (e.g., graft versus host disease (GvHD), autoimmune diseases), as well as with both acute and chronic transplant rejection and with T cell cytotoxicity (e.g., to predict treatment efficacy in patients being treated with cancer immune therapies such as checkpoint blockade inhibitors or CAR T cell therapies). In one embodiment, the peptide sequences are recognized by Granzyme B (GzmB), such as a recombinant GzmB (SEQ ID NO: 1). In another embodiment, the peptide sequences are recognized by T cell-associated proteases (such as for example and not limitation, Granzyme B, Granzyme A, MALT1, Caspase 8, Calpain 2, and Cathepsin X). In yet another embodiment, the peptide sequences are recognized by complement-associated proteases (such as for example and not limitation, C1s, C1r, MASP2, Factor I, Factor D). In one embodiment, the peptide sequences are recognized by fibrosis-associated proteases (such as for example and not limitation, ADAMTS1, MMP2, MMP9). In another embodiment, the peptide sequences are recognized by inflammation-associated proteases (such as for example and not limitation, elastase, cathepsin G, PR-3, thrombin, kallikreins 1&6, tryptase, and chymase). The peptide sequences may contain amino acids in all L form, all D form, or a mix of L and D forms (ranging from 50% D and 50% L forms to 99% D or L form and 1% L or D form).

In some embodiments, the one or more detectable peptide sequences linked to the scaffold comprises a reporter, a GzmB recognition/cleavage sequence comprising any of SEQ ID NOs 2 to 81, and combinations thereof, and another peptide, protein, nucleic acid, lipid, fatty acid, oligonucle-otide, oligopeptide, oligolipid, antibody, antibody fragment, aptamer and/or binding protein (including binding protein fragments), which can aid in coupling the detectable peptide to the scaffold. The peptide sequences comprising any of SEQ ID NOs 2 to 81 can contain amino acids in all L form, all D form, or a mix of L and D forms (ranging from 50% D and 50% L forms to 99% D or L form and 1% L or D form). In one specific embodiment, the one or more peptide sequences comprises a GzmB recognition/cleavage sequence comprising any of SEQ ID NOs 2 to 81 and combinations thereof, and polyethylene glycol (e.g., one or more polyethylene glycol molecules). The polyethylene glycol may be of any suitable molecular weight, such as for example and not limitation, 100 to 200,000, 1000 to 100, 000, 2,500 to 75,000, 4,000 to 50,000, and 5,000 to 20,000.

In other embodiments, the one or more detectable peptide sequences linked to the scaffold comprises a reporter, a protease recognition/cleavage sequence comprising any of SEQ ID NOs 82 to 136, and combinations thereof, and another peptide, protein, nucleic acid, lipid, fatty acid, oligonucleotide, oligopeptide, oligolipid, antibody, antibody fragment, aptamer and/or binding protein (including binding protein fragments), which can aid in coupling the detectable peptide to the scaffold. The peptide sequences comprising any of SEQ ID NOs 82 to 136 can contain amino acids in all L form, all D form, or a mix of L and D forms (ranging from 50% D and 50% L forms to 99% D or L form and 1% L or D form). In one specific embodiment, the one or more peptide sequences comprises a reporter, a protease recognition/cleavage sequence comprising any of SEQ ID NOs 82 to 136 and combinations thereof, and polyethylene glycol (e.g., one or more polyethylene glycol molecules). The polyethylene glycol may be of any suitable molecular weight, such as for example and not limitation, 100 to 200,000, 1000 to 100,000, 2,500 to 75,000, 4,000 to 50,000, and 5,000 to 20,000.

In specific embodiments, the one or more detectable peptide sequences linked to the scaffold may comprise a recognition/cleavage site for GzmB. In some embodiments, the peptide may comprise an amino acid sequence comprising at least one of AIEPDGSC (SEQ ID NO: 2), ASGIEPDSGGSC (SEQ ID NO: 3), AKSKIEFDFGVKKC (SEQ ID NO: 4), AIEPDSGC (SEQ ID NO: 5), AIEPDGSSKC (SEQ ID NO: 6), AIEPDSGSKC (SEQ ID NO: 7), AKSIEPDGSSKC (SEQ ID NO: 8), AKSIEPDSG-SKC (SEQ ID NO: 9), AIEFDGSC (SEQ ID NO: 10), AIEFDSGC (SEQ ID NO: 11), AIEFDSGSKC (SEQ ID NO: 12), AKSIEFDSGSKC (SEQ ID NO: 13), AIEFDSGVSKC (SEQ ID NO: 14), and combinations thereof, including combinations with any peptide disclosed herein. Suitable linkers may be added to the N-terminus and/or C-terminus of the peptide, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 2-14, and modifications thereof (e.g., linkers) as well as vectors comprising such nucleic acids, and host cells comprising such vectors. The peptides comprising any of the amino acid sequences comprising SEQ ID NOs 2-14 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-ter-minus and/or C-terminus. The disclosure further contem-plates methods of making said vectors and host cells accord-ing to cloning methods well known in the art.

In some embodiments, the one or more detectable peptide sequences linked to the scaffold may comprise an amino acid sequence comprising one or more D-form amino acids, such as for example and not limitation, at least one of AIEPDGSc (SEQ ID NO: 15), AsGIEPDSGGsc (SEQ ID NO: 16), AksKIEFDFGVKkc (SEQ ID NO: 17), AIEPDSGc (SEQ ID NO: 18), AIEPDGSskc (SEQ ID NO: 19), AIEPDSGskc (SEQ ID NO: 20), AksIEPDGSskc (SEQ ID NO: 21), AksIEPDSGskc (SEQ ID NO: 22), AIEFDGSc (SEQ ID NO: 23), AIEFDSGc (SEQ ID NO: 24), AIEFDSGskc (SEQ ID NO: 25), AksIEFDSGskc (SEQ ID NO: 26), AIEFDSGVskc (SEQ ID NO: 27), and combinations thereof, including combinations with any peptide disclosed herein. Suitable linkers may be added to the N-terminus and/or C-terminus of the peptide, and/or to residues within the one or more peptide sequences. The disclosure also contemplates nucleic acids (e.g., DNA and RNA) encoding each of SEQ ID NOs 15-27, and modifications thereof (e.g., linkers) as well as vectors comprising such nucleic acids, and host cells comprising such vectors. The peptides com-prising any of the amino acid sequences comprising SEQ ID NOs 15-27 may further comprise one or more of polyeth-ylene glycol (of any suitable molecular weight, such as for example and not limitation, 100 to 200,000, 1000 to 100, 000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In other embodiments, the one or more detectable peptide sequences linked to the scaffold comprises a GzmB recog-nition/cleavage sequence and a Glu-1-Fibrinopeptide B pep-tide EGVNDNEEGFFSAR (Glufib peptide; SEQ ID NO: 28). In one embodiment, the Glufib peptide comprises one or more D-form amino acids, such as for example and not limitation, eGvndneeGffsar (lowercase letters denote D-form amino acids; SEQ ID NO: 29). In some embodi-ments, the peptide comprises an amino acid sequence com-prising at least one of AIEPDGSC (SEQ ID NO: 30), ASGIEPDSGGSC (SEQ ID NO: 31), AKSKIEFDFGVKKC (SEQ ID NO: 32), AIEPDSGC (SEQ ID NO: 33), AIEPDGSSKC (SEQ ID NO: 34), AIEPDSG-SKC (SEQ ID NO: 35), AKSIEPDGSSKC (SEQ ID NO: 36), AKSIEPDSGSKC (SEQ ID NO: 37), AIEFDGSC (SEQ ID NO: 38), AIEFDSGC (SEQ ID NO: 39), AIEFDSGSKC (SEQ ID NO: 40), AKSIEFDSGSKC (SEQ ID NO: 41), AIEFDSGVSKC (SEQ ID NO: 42), aIEPDGSc (SEQ ID NO: 43), asGIEPDSGGsc (SEQ ID NO: 44), aksKIEFDFGVKkc (SEQ ID NO: 45), aIEPDSGc (SEQ ID NO: 46), aIEPDGSskc (SEQ ID NO: 47), aIEPDSGskc (SEQ ID NO: 48), aksIEPDGSskc (SEQ ID NO: 49), aksIEPDSGskc (SEQ ID NO: 50), aIEFDGSc (SEQ ID NO: 51), aIEFDSGc (SEQ ID NO: 52), aIEFDSGskc (SEQ ID NO: 53), aksIEFDSGskc (SEQ ID NO: 54), aIEFDSGVskc (SEQ ID NO: 55), and combinations thereof, which are operatively (e.g., transcriptionally and/or translationally) linked/coupled to EGVNDNEEGFFSAR (SEQ ID NO: 28) and/or eGvndneeGffsar (SEQ ID NO: 29). In specific embodiments, the peptide comprises an amino acid sequence comprising one or more of EGVNDNEEGFF-SARKAIEPDGSC (SEQ ID NO: 56), EGVNDNEEGFF-SARKASGIEPDSGGSC (SEQ ID NO: 57), EGVND-NEEGFFSARKAKSKIEFDFGVKKC (SEQ ID NO: 58), EGVNDNEEGFFSARKAIEPDSGC (SEQ ID NO: 59), EGVNDNEEGFFSARKAIEPDGSSKC (SEQ ID NO: 60), EGVNDNEEGFFSARKAIEPDSGSKC (SEQ ID NO: 61), EGVNDNEEGFFSARKAKSIEPDGSSKC (SEQ ID NO: 62), EGVNDNEEGFFSARKAKSIEPDSGSKC (SEQ ID NO: 63), EGVNDNEEGFFSARKAIEFDGSC (SEQ ID NO: 64), EGVNDNEEGFFSARKAIEFDSGC (SEQ ID NO: 65), EGVNDNEEGFFSARKAIEFDSGSKC (SEQ ID NO: 66), EGVNDNEEGFFSARKAKSIEFDSGSKC (SEQ ID NO: 67), EGVNDNEEGFFSARKAIEFDSGVSKC (SEQ ID NO: 68), eGvndneeGffsarKaIEPDGSc (SEQ ID NO: 69), eGvndneeGffsarKasGIEPDSGGsc (SEQ ID NO: 70), eGvndneeGffsarKaksKIEFDFGVKkc (SEQ ID NO: 71), eGvndneeGffsarKaIEPDSGc (SEQ ID NO: 72), eGvndneeGffsarKaIEPDGSskc (SEQ ID NO: 73), eGvnd-neeGffsarKaIEPDSGskc (SEQ ID NO: 74), eGvndnee GffsarKaksIEPDGSskc (SEQ ID NO: 75), eGvndneeGff-sarKaksIEPDSGskc (SEQ ID NO: 76), eGvndneeGffsarKaIEFDGSc (SEQ ID NO: 77), eGvnd-neeGffsarKaIEFDSGc (SEQ ID NO: 78), eGvndneeGff-sarKaIEFDSGskc (SEQ ID NO: 79), eGvndneeGffsarKaks-IEFDSGskc (SEQ ID NO: 80), eGvndneeGffsarKaIEFDSGVskc (SEQ ID NO: 81), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 28-81, and modifications thereof (e.g., linkers) as well as vectors comprising such nucleic acids, and host cells comprising such vectors. The peptides comprising any of the amino acid sequences comprising SEQ ID NOs 30-81 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In other embodiments, the one or more detectable peptide sequences linked to the scaffold comprises a recognition/cleavage site that can be recognized by another T cell-related protease, e.g., a protease involved in T cell killing and/or a protease involved in T cell activation. Non-limiting examples of proteases involved in T cell killing include Granzyme B and Granzyme A. Non-limiting examples of proteases involved in T cell activation include MALT1, Caspase 8, Calpain 2, and Cathepsin X.

In an embodiment, the one or more detectable peptide sequences linked to the scaffold comprises a Granzyme A recognition/cleavage site, such as for example and not limitation, an amino acid sequence comprising at least one of AAPVRSL (SEQ ID NO: 82), ALDPRSF (SEQ ID NO: 83), ATQNKAS (SEQ ID NO: 84) and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 82-84, and modifications thereof (e.g., linkers) as well as vectors comprising such nucleic acids, and host cells comprising such vectors. The peptides comprising any of the amino acid sequences comprising SEQ ID NOs 82-84 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a MALT1 recognition/cleavage site, such as for example and not limitation, an amino acid sequence comprising ACYLD (SEQ ID NO: 85) and combinations including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NO: 85, and modifications thereof (e.g., linkers) as well as vectors comprising such nucleic acids, and host cells comprising such vectors. The peptides comprising any of the amino acid sequences comprising SEQ ID NO: 85 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a Caspase 8 recognition/cleavage site, such as for example and not limitation, an amino acid sequence comprising at least one of AIETDGS (SEQ ID NO: 86) and ALEVDCY (SEQ ID NO: 87) and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 86-87, and modifications thereof (e.g., linkers) as well as vectors comprising such nucleic acids, and host cells comprising such vectors. The peptides comprising any of the amino acid sequences comprising SEQ ID NOs 86-87 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a Caspase 3 recognition/cleavage site, such as for example and not limitation, an amino acid sequence comprising at least one of ADEVDNK (SEQ ID NO: 116), ADEVDGV (SEQ ID NO: 117), ADEVDRD (SEQ ID NO: 118), ADEVDGV (SEQ ID NO: 119) and ALEVDCY (SEQ ID NO: 120) and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 86-87, and modifications thereof (e.g., linkers) as well as vectors comprising such nucleic acids, and host cells comprising such vectors. The peptides comprising any of the amino acid sequences comprising SEQ ID NOs 86-87 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a Calpain2 recognition/cleavage site, such as for example and not limitation, an amino acid sequence comprising AEPLFAERK (SEQ ID NO: 88) and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NO: 88, and modifications thereof (e.g., linkers) as well as vectors comprising such nucleic acids, and host cells comprising such vectors. The peptides comprising any of the amino acid sequences comprising SEQ ID NO: 88 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a Cathepsin X recognition/cleavage site, such as for example and not limitation, an amino acid sequence comprising AMNPKFA (SEQ ID NO: 89) and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NO: 89, and modifications thereof (e.g., linkers) as well as vectors comprising such nucleic acids, and host cells comprising such vectors. The peptides comprising any of the amino acid sequences comprising SEQ ID NO: 89 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a Cls, Clr, MASP2, Factor I, and/or Factor D recognition/cleavage site, such as for example and not limitation, an amino acid sequence comprising at least one of ALQRIYKC (SEQ ID NO: 90), AKSVARTLLVKC (SEQ ID NO: 91), AEEKQRIIGC (SEQ ID NO: 92), AQRQRIIGGC (SEQ ID NO: 93), ALGRGGSC (SEQ ID NO: 94), AKYLGRSYKVC (SEQ ID NO: 95), ARALERGLQDC (SEQ ID NO: 96), ASLGRKIQIC (SEQ ID NO: 97), AGLQRALEIC (SEQ ID NO: 98), AKVFMGRVYDPC (SEQ ID NO: 99), ASSTGRNGFKC (SEQ ID NO: 100), AKTTGGRIYGGC (SEQ ID NO: 101), ADPRGGSC (SEQ ID NO: 102), AVPRGGSC (SEQ ID NO: 103), ALPSRSSKIC (SEQ ID NO: 104), AHRGRTLEIC (SEQ ID NO: 105), ASTGRNGFKC (SEQ ID NO: 106), AQQKRKIVLC (SEQ ID NO: 107), AQARKIVLC (SEQ ID NO: 108), AQARGGSC (SEQ ID NO: 109), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 90-109, and modifications thereof (e.g., linkers) as well as vectors comprising such nucleic acids, and host cells comprising such vectors. The peptides comprising any of the amino acid sequences comprising SEQ ID NOs 90-109 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises an ADAMTS1 recognition/cleavage site, such as for example and not limitation, an amino acid sequence comprising at least one of AIPENFF (SEQ ID NO: 110), AKEEEGL (SEQ ID NO: 111), ANLVYMV (SEQ ID NO: 112), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 110-112, and modifications thereof (e.g., linkers) as well as vectors comprising such nucleic acids, and host cells comprising such vectors. The peptides comprising any of the amino acid sequences comprising SEQ ID NOs 110-112 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a MMP2 recognition/cleavage site, such as for example and not limitation, an amino acid sequence comprising at least one of ARLAAIT (SEQ ID NO: 113), ASLSRLT (SEQ ID NO: 114), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding each of SEQ ID NOs 113-114, and modifications thereof (e.g., linkers) as well as vectors comprising such nucleic acids, and host cells comprising such vectors. The peptides comprising any of the amino acid sequences comprising SEQ ID NOs 113-114 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a MMP9 recognition/cleavage site, such as for example and not limitation, an amino acid sequence comprising APLGVRGK (SEQ ID NO: 115), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NO: 115, and modifications thereof (e.g., linkers) as well as vectors comprising such nucleic acids, and host cells comprising such vectors. The peptides comprising any of the amino acid sequences comprising SEQ ID NO: 115 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises an elastane, cathepsin G, and/or PR-3 recognition/cleavage site, such as for example and not limitation, an amino acid sequence comprising at least one of AAAPVc (SEQ ID NO: 121), AAAPAc (SEQ ID NO: 122), AAAPLc (SEQ ID NO: 123), AAAPMc (SEQ ID NO: 124), AAAPFc (SEQ ID NO: 125), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NOs 121-125, and modifications thereof (e.g., linkers) as well as vectors comprising such nucleic acids, and host cells comprising such vectors. The peptides comprising any of the amino acid sequences comprising SEQ ID NOs 121-125 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a thrombin recognition/cleavage site, such as for example and not limitation, an amino acid sequence comprising at least one of GGFPRSGGGc (SEQ ID NO: 126), AGFPRSGGGc, (SEQ ID NO: 127), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NOs 126-127, and modifications thereof (e.g., linkers) as well as vectors comprising such nucleic acids, and host cells comprising such vectors. The peptides comprising any of the amino acid sequences comprising SEQ ID NOs 126-127 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a kallikrein 1 recognition/cleavage site, such as for example and not limitation, an amino acid sequence comprising AIKFFSAc (SEQ ID NO: 128), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NO: 128, and modifications thereof (e.g., linkers) as well as vectors comprising such nucleic acids, and host cells comprising such vectors. The peptides comprising any of the amino acid sequences comprising SEQ ID NO: 128 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a kallikrein 6 recognition/cleavage site, such as for example and not limitation, an amino acid sequence comprising at least one of ALRQRESc (SEQ ID NO: 129), AAEFRHDc (SEQ ID NO: 130), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NOs 129-130, and modifications thereof (e.g., linkers) as well as vectors comprising such nucleic acids, and host cells comprising such vectors. The peptides comprising any of the amino acid sequences comprising SEQ ID NOs 129-130 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a chymase recognition/cleavage site, such as for example and not limitation, an amino acid sequence comprising at least one of AAAPFc (SEQ ID NO: 131), AQFVLTEc (SEQ ID NO: 132), ARETYGEc (SEQ ID NO: 133), AATVYVDc (SEQ ID NO: 134), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NOs 131-134, and modifications thereof (e.g., linkers) as well as vectors comprising such nucleic acids, and host cells comprising such vectors. The peptides comprising any of the amino acid sequences comprising SEQ ID NOs 131-134 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

In another embodiment, the one or more detectable peptide sequences linked to the scaffold comprises a tryptase recognition/cleavage site, such as for example and not limitation, an amino acid sequence comprising at least one of APLDKKRc (SEQ ID NO: 135), ADKVKAQc (SEQ ID NO: 136), and combinations thereof, including combinations with any peptide disclosed herein. Suitable linkers may be added to the N-terminus and/or C-terminus of the one or more peptide sequences, and/or to residues within the one or more peptide sequences. The amino acids can be present in all L form, all D form, or a mix of L and D forms (ranging from 50% D and 50% L forms to 99% D or L form and 1% L or D form). The disclosure also contemplates nucleic acids (e.g., DNA and RNA) encoding SEQ ID NOs 135-136, and modifications thereof (e.g., linkers) as well as vectors comprising such nucleic acids, and host cells comprising such vectors. The peptides comprising any of the amino acid sequences comprising SEQ ID NOs 135-136 may further comprise one or more of polyethylene glycol (of any suitable molecular weight, such as for example and not limitation, 100 to 200,000, 1000 to 100,000, 2,500 to 75,000, 4,000 to 50,000, and 5,000 to 20,000), Glufib, an internal lysine residue for linking, and/or a cysteine residue at the N-terminus and/or C-terminus. The disclosure further contemplates methods of making said vectors and host cells according to cloning methods well known in the art.

The disclosure in some aspects involves administering to a subject, such as for example and not limitation a transplant recipient, a composition comprising at least one detectable peptide sequence coupled/linked to a scaffold as described herein, identifying a biological sample from the subject in which to detect the detectable peptide sequence and optionally collecting the sample; and, subjecting the biological sample to an analysis method in order to detect the presence of the peptide sequence. The presence of the detectable marker in the biological sample is indicative of an active enzyme or a substrate within the subject, and allows further diagnosis of a condition, detection of a condition, prediction of a condition, classification of the patient, and/or selection of the patient, discussed in further detail hereinbelow. Optionally, the patient is treated with an appropriate therapeutic composition and/or method based on the results of the analysis method.

The disclosure also provides methods of ex vivo analysis of protease activity. In such embodiments, a biological sample (such as for example and not limitation, a bodily fluid containing T cells, urine, blood, lymphatic fluid, plasma, saliva, etc.) is collected from a subject and contacted with a composition comprising at least one detectable peptide sequence linked/coupled to a scaffold as described herein. The sample is subjected to similar analyses as discussed herein in order to detect the presence of the peptide sequence. The presence of the detectable marker in the biological sample is indicative of an active enzyme or a substrate within the subject, and allows further diagnosis of a condition, detection of a condition, prediction of a condition, classification of the patient, and/or selection of the patient, discussed in further detail hereinbelow.

The present disclosure also provides methods of diagnosing acute rejection in a patient who is a transplant recipient by using the compositions described herein, as well as methods of detecting acute rejection in such a patient, predicting acute rejection in such a patient, classifying a transplant recipient as having acute rejection of the transplanted tissue, monitoring acute rejection in a transplant recipient, selecting a transplant recipient for a clinical trial for acute rejection-related therapeutic compositions and/or methods, and methods of treating acute rejection in a transplant recipient. The detectable peptide sequences, as discussed herein, are released at the site of protease cleavage, producing a localized detectable signal (that can be detected at the site of cleavage or downstream of the site of cleavage), and can accumulate in draining lymph nodes, blood, urine, and other bodily fluids where they can be detected (e.g., by methods as described in US2014/0303014 and US2014/0363833, each of which is incorporated herein by reference).

In one embodiment, the disclosure provides a method of diagnosing acute organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) acutely rejecting the transplant when the activity of the target protease in the sample is greater than the reference activity of the target protease; or (ii) not acutely rejecting the transplant when the activity of the target protease in the sample is less than the reference activity of the target protease; and (g) optionally treating the acute rejection via a therapeutic composition and/or method and/or preventing the acute rejection via a prophylactic composition and/or method.

In another embodiment, the disclosure provides a method of detecting acute organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) acutely rejecting the transplant when the activity of the target protease in the sample is greater than the reference activity of the target protease; or (ii) not acutely rejecting the transplant when the activity of the target protease in the sample is less than the reference activity of the target protease; and (g) optionally treating the acute rejection via a therapeutic composition and/or method and/or preventing the acute rejection via a prophylactic composition and/or method.

In another embodiment, the disclosure provides a method of predicting acute organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) at risk of or likely to acutely reject the transplant when the activity of the target protease in the sample is greater than the reference activity of the target protease; or (ii) not at risk of or not likely to acutely reject the transplant when the activity of the target protease in the sample is less than the reference activity of the target protease; and (g) optionally treating the acute rejection via a therapeutic composition and/or method and/or preventing the acute rejection via a prophylactic composition and/or method.

In another embodiment, the disclosure provides a method of classifying a transplant recipient subject as having or likely to have acute organ rejection comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to acutely reject the transplant when the activity of the target protease in the sample is greater than the reference activity of the target protease; or (ii) not having, not at risk of, or not likely to acutely reject the transplant when the activity of the target protease in the sample is less than the reference activity of the target protease; and (g) optionally treating the acute rejection via a therapeutic composition and/or method and/or preventing the acute rejection via a prophylactic composition and/or method.

In another embodiment, the disclosure provides a method of monitoring acute organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to acutely reject the transplant when the activity of the target protease in the sample is greater than the reference activity of the target protease; or (ii) not having, not at risk of, or not likely to acutely reject the transplant when the activity of the target protease in the sample is less than the reference activity of the target protease; and (g) optionally treating the acute rejection via a therapeutic composition and/or method and/or preventing the acute rejection via a prophylactic composition and/or method. In some embodiments, steps (a)-(g) can be repeated over a period of hours to weeks after the subject has received the transplanted tissue, for example, 3 hours to three weeks after receiving the transplanted tissue. In other embodiments, steps (a)-(g) can be repeated over a period of hours to weeks after the subject has clinical signs of graft functional decline, for example, 3 hours to three weeks after the first sign of graft functional decline.

In another embodiment, the disclosure provides a method of selecting a transplant recipient subject for a clinical trial for an acute organ rejection therapeutic and/or prophylactic compositions and/or methods comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) suitable for the trial when the activity of the target protease in the sample is greater than the reference activity of the target protease; or (ii) not suitable for the trial when the activity of the target protease in the sample is less than the reference activity of the target protease.

In another embodiment, the disclosure provides a method of treating a transplant recipient subject for acute organ rejection comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to acutely reject the transplant when the activity of the target protease in the sample is greater than the reference activity of the target protease; or (ii) not having, not at risk of, or not likely to acutely reject the transplant when the activity of the target protease in the sample is less than the reference activity of the target protease; and (g) utilizing appropriate therapeutic and/or prophylactic compositions and/or methods if the subject has acute organ rejection as identified in step f).

In a related aspect, the disclosure provides methods of diagnosing chronic rejection in a patient who is a transplant recipient by using the compositions described herein, as well as methods of detecting chronic rejection in such a patient, predicting chronic rejection in such a patient, classifying a transplant recipient as having chronic rejection of the transplanted tissue, monitoring chronic rejection in a transplant recipient, selecting a transplant recipient for a clinical trial for chronic rejection-related therapeutic compositions and/ or methods, and methods of treating chronic rejection in a transplant recipient. The detectable peptide sequences, as discussed herein, are released at the site of protease cleavage, producing a localized detectable signal (that can be detected at the site of cleavage or downstream of the site of cleavage), and can accumulate in draining lymph nodes, blood, urine, and other bodily fluids where they can be detected (e.g., by methods as described in US2014/0303014 and US2014/0363833, each of which is incorporated herein by reference).

In one embodiment, the disclosure provides a method of diagnosing chronic organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) chronically rejecting the transplant when the activity of the target protease in the sample is greater than the reference activity of the target protease; or (ii) not chronically rejecting the transplant when the activity of the target protease in the sample is less than the reference activity of the target protease; and (g) optionally treating the chronic rejection via a therapeutic composition and/or method and/or preventing the chronic rejection via a prophylactic composition and/or method.

In another embodiment, the disclosure provides a method of detecting chronic organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) chronically rejecting the transplant when the activity of the target protease in the sample is greater than the reference activity of the target protease; or (ii) not chronically rejecting the transplant when the activity of the target protease in the sample is less than the reference activity of the target protease; and (g) optionally treating the chronic rejection via a therapeutic composition and/or method and/or preventing the chronic rejection via a prophylactic composition and/or method.

In another embodiment, the disclosure provides a method of predicting chronic organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) at risk of or likely to chronically reject the transplant when the activity of the target protease in the sample is greater than the reference activity of the target protease; or (ii) not at risk of or not likely to chronically reject the transplant when the activity of the target protease in the sample is less than the reference activity of the target protease; and (g) optionally treating the chronic rejection via a therapeutic composition and/or method and/or preventing the chronic rejection via a prophylactic composition and/or method.

In another embodiment, the disclosure provides a method of classifying a transplant recipient subject as having or likely to have chronic organ rejection comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to chronically reject the transplant when the activity of the target protease in the sample is greater than the reference activity of the target protease; or (ii) not having, not at risk of, or not likely to chronically reject the transplant when the activity of the target protease in the sample is less than the reference activity of the target protease; and (g) optionally treating the chronic rejection via a therapeutic composition and/or method and/or preventing the chronic rejection via a prophylactic composition and/or method.

In another embodiment, the disclosure provides a method of monitoring chronic organ rejection in a transplant recipient subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to chronically reject the transplant when the activity of the target protease in the sample is greater than the reference activity of the target protease; or (ii) not having, not at risk of, or not likely to chronically reject the transplant when the activity of the target protease in the sample is less than the reference activity of the target protease; and (g) optionally treating the chronic rejection via a therapeutic composition and/or method and/or preventing the chronic rejection via a prophylactic composition and/or method. Steps (a)-(g) can be repeated over a period of hours to months to years after the subject has received the transplanted tissue, for example, 3 hours to three weeks after receiving the transplanted tissue. In some embodiments, steps (a)-(g) are repeated every few months beginning one to thirty years after the subject has received the transplanted tissue. In other embodiments, steps (a)-(g) are repeated over a period of hours to weeks after the subject has clinical signs of graft functional decline, for example, 3 hours to three weeks after the first sign of graft functional decline.

In another embodiment, the disclosure provides a method of selecting a transplant recipient subject for a clinical trial for a chronic organ rejection therapeutic and/or prophylactic compositions and/or methods comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) suitable for the trial when the activity of the target protease in the sample is greater than the reference activity of the target protease; or (ii) not suitable for the trial when the activity of the target protease in the sample is less than the reference activity of the target protease.

In another embodiment, the disclosure provides a method of treating a transplant recipient subject for chronic organ rejection comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of or likely to chronically reject the transplant when the activity of the target protease in the sample is greater than the reference activity of the target protease; or (ii) not having, not at risk of, or not likely to chronically reject the transplant when the activity of the target protease in the sample is less than the reference activity of the target protease; and (g) utilizing appropriate therapeutic and/or prophylactic compositions and/or methods if the subject has chronic organ rejection as identified in step f).

In another related aspect, the disclosure provides methods of diagnosing immune conditions related to T cell cytotoxicity (e.g., graft versus host disease (GvHD) and autoimmune diseases). The disclosure also provides methods of detecting such immune conditions in a patient, predicting such immune conditions in a patient, classifying a patient as having such immune conditions, monitoring such immune conditions in a patient, selecting a patient for a clinical trial for such immune condition-related therapeutic compositions and/or methods, and methods of treating such immune conditions in a patient. The detectable peptide sequences, as discussed herein, are released at the site of protease cleavage, producing a localized detectable signal (that can be detected at the site of cleavage or downstream of the site of cleavage), and can accumulate in draining lymph nodes, blood, urine, and other bodily fluids where they can be detected (e.g., by methods as described in US2014/0303014 and US2014/0363833, each of which is incorporated herein by reference).

In one embodiment, the disclosure provides a method of diagnosing immune conditions related to T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having the immune condition when the transplant when the activity of the target protease in the sample is greater than the reference activity of the target protease; or (ii) not having the immune condition when the activity of the target protease in the sample is less than the reference activity of the target protease; and (g) optionally treating the immune condition via a therapeutic composition and/or method and/or preventing the immune condition via a prophylactic composition and/or method.

In another embodiment, the disclosure provides a method of detecting immune conditions related to T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having the immune condition when the activity of the target protease in the sample is greater than the reference activity of the target protease; or (ii) not having the immune condition when the activity of the target protease in the sample is less than the reference activity of the target protease; and (g) optionally treating the immune condition via a therapeutic composition and/or method and/or preventing the immune condition via a prophylactic composition and/or method.

In another embodiment, the disclosure provides a method of predicting immune conditions related to T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) at risk of developing or likely to develop the immune condition when the activity of the target protease in the sample is greater than the reference activity of the target protease; or (ii) not at risk of developing or not likely to develop the immune condition when the activity of the target protease in the sample is less than the reference activity of the target protease; and (g) optionally treating the immune condition via a therapeutic composition and/or method and/or preventing the immune condition via a prophylactic composition and/or method.

In another embodiment, the disclosure provides a method of classifying a subject as having or likely to have immune conditions related to T cell cytotoxicity comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop the immune condition when the activity of the target protease in the sample is greater than the reference activity of the target protease; or (ii) not having, not at risk of developing, or not likely to develop the immune condition when the activity of the target protease in the sample is less than the reference activity of the target protease; and (g) optionally treating the immune condition via a therapeutic composition and/or method and/or preventing the immune condition via a prophylactic composition and/or method.

In another embodiment, the disclosure provides a method of monitoring immune conditions related to T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop the immune condition when the activity of the target protease in the sample is greater than the reference activity of the target protease; or (ii) not having, not at risk of developing, or not likely to develop the immune condition when the activity of the target protease in the sample is less than the reference activity of the target protease; and (g) optionally treating the immune condition via a therapeutic composition and/or method and/or preventing the immune condition via a prophylactic composition and/or method. Steps (a)-(g) can be repeated over a period of hours to months to years to decades, for example for a period of 3 hours to 3 months, and the monitoring period can vary depending on the immune condition.

In another embodiment, the disclosure provides a method of selecting a transplant recipient subject for a clinical trial for a therapeutic and/or prophylactic compositions and/or methods for a T-cell toxicity-related immune disorder comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) suitable for the trial when the activity of the target protease in the sample is greater than the reference activity of the target protease; or (ii) not suitable for the trial when the activity of the target protease in the sample is less than the reference activity of the target protease.

In another embodiment, the disclosure provides a method of treating a subject for a T-cell toxicity-related immune disorder comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop the immune condition when the activity of the target protease in the sample is greater than the reference activity of the target protease; or (ii) not having, not at risk of developing, or not likely to develop the immune condition when the activity of the target protease in the sample is less than the reference activity of the target protease; and (g) utilizing appropriate therapeutic and/or prophylactic compositions and/or methods if the subject has an immune disorder as identified in step f).

In another related aspect, the disclosure provides methods of diagnosing T cell cytotoxicity (e.g., to predict treatment efficacy in patients being treated with cancer immune therapies such as checkpoint blockade inhibitors or CAR T cell therapies). The disclosure also provides methods of detecting T cell cytotoxicity in a patient, predicting T cell cytotoxicity in a patient, classifying a patient as having T cell cytotoxicity, monitoring T cell cytotoxicity in a patient, selecting a patient for a clinical trial for T cell cytotoxicity-related therapeutic compositions and/or methods, and methods of treating T cell cytotoxicity in a patient. The detectable peptide sequences, as discussed herein, are released at the site of protease cleavage, producing a localized detectable signal (that can be detected at the site of cleavage or downstream of the site of cleavage), and can accumulate in draining lymph nodes, blood, urine, and other bodily fluids where they can be detected (e.g., by methods as described in US2014/0303014 and US2014/0363833, each of which is incorporated herein by reference).

In one embodiment, the disclosure provides a method of diagnosing T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d)

determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) optionally treating the T cell cytotoxicity via a therapeutic composition and/or method and/or preventing the T cell cytotoxicity via a prophylactic composition and/or method.

In another embodiment, the disclosure provides a method of detecting T cell cytotoxicity in a subject comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) optionally treating the T cell cytotoxicity via a therapeutic composition and/or method and/or preventing the T cell cytotoxicity via a prophylactic composition and/or method.

In another embodiment, the disclosure provides a method of predicting T cell cytotoxicity in a subject comprising: (a) administering a composition comprising a nanosensor to the subject, substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) optionally treating the T cell cytotoxicity via a therapeutic composition and/or method and/or preventing the T cell cytotoxicity via a prophylactic composition and/or method.

In another embodiment, the disclosure provides a method of classifying a subject as having or likely to have T cell cytotoxicity comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) optionally treating the T cell cytotoxicity via a therapeutic composition and/or method and/or preventing the T cell cytotoxicity via a prophylactic composition and/or method.

In another embodiment, the disclosure provides a method of monitoring T cell cytotoxicity in a subject comprising: (a) administering a composition comprising a nanosensor to the subject, substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i)) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) optionally treating the T cell cytotoxicity via a therapeutic composition and/or method and/or preventing the T cell cytotoxicity via a prophylactic composition and/or method. Steps (a)-(g) can be repeated over a period of hours to months to years to decades, and the monitoring period can vary depending on the immune condition, for example 3 hours to 3 months.

In another embodiment, the disclosure provides a method of selecting a subject for a clinical trial for T cell cytotoxicity-related therapeutic and/or prophylactic compositions and/or methods comprising: (a) administering a composition comprising a nanosensor to the subject, the nanosensor comprising a scaffold; a linker coupled to the scaffold domain; at least one peptide substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) suitable for the trial when the activity of the target protease in the sample is greater than the reference activity of the target protease; or (ii) not suitable for the trial when the activity of the target protease in the sample is less than the reference activity of the target protease.

In another embodiment, the disclosure provides a method of treating a subject for T cell cytotoxicity comprising: (a) administering a composition comprising a nanosensor to the subject, substrate coupled to the linker, the peptide substrate comprising a target protease cleavage sequence; and a detectable reporter coupled to the peptide substrate; (b) obtaining a sample of a bodily fluid from the subject; (c) detecting a level of the detectable reporter in the sample of the bodily fluid; (d) determining an activity of the target protease based on the level of the detectable reporter in the sample of the bodily fluid; (e) comparing the activity of the target protease in the sample to a reference activity of the target protease; (f) identifying the subject as: (i) having, at risk of developing, or likely to develop T cell cytotoxicity when the activity of the target protease in the sample is greater than the reference activity of the target protease; or (ii) not having, not at risk of developing, or not likely to develop T cell cytotoxicity when the activity of the target protease in the sample is less than the reference activity of the target protease; and (g) utilizing appropriate therapeutic and/or prophylactic compositions and/or methods if the subject has T cell cytotoxicity as identified in step f).

In any of the foregoing embodiments of any of the disclosed methods, the composition comprising the nanosensor is administered intravenously. In any of the foregoing embodiments, the composition comprising the nanosensor further comprises a pharmaceutically acceptable carrier and/or adjuvant. In any of the foregoing embodiments, the peptide substrate comprises a detectable peptide sequence as discussed herein, e.g., a detectable peptide sequence comprising an amino acid sequence comprising one or more of SEQ ID NOs 2-136. In any of the foregoing embodiments, the detectable reporter can be, for example and not limitation, a fluorophore, a mass spectrometry bar code, and/or an imaging agent (e.g., a contrast imaging agent or a PET imaging agent). In any of the foregoing embodiments, the bodily fluid can be, for example and not limitation, urine, blood, lymphatic fluid, plasma, and/or saliva. In any of the foregoing embodiments, a sample of a bodily fluid is obtained 30 minutes to 48 hours, including but not limited to 30 minutes to 6 hours, after administration of the composition comprising the nanosensor. In any of the foregoing embodiments, the target protease is selected from the group consisting of Granzyme B, Granzyme A, MALT1, Caspase 8, Calpain 2, Cathepsin X, Cls, Clr, MASP2, Factor I, Factor D, ADAMTS1, MMP2, and MMP9. In any of the foregoing embodiments, the reporter domain enables detection by light spectroscopy, near-infrared imaging, fluorescent imaging, bioluminescent imaging, ELISA, PCR (for DNA barcodes), spectrophotometry, mass spectrometry (e.g., bar code mass spectrometry), and/or imaging (e.g., CAT, MRI, PET), and/or by methods described in any of WO2007/106415, US2010/0240050, US2014/0303014 and US2014/0363833, each of which is incorporated herein by reference.

In any of the foregoing embodiments, a single sample of bodily fluid is taken from the subject for analysis. In any of the foregoing embodiments, multiple samples of bodily fluid are taken in order to monitor the protease activity, and thus acute and/or chronic rejection, over time. Such samples can be taken over a period of 30 minutes to 4 weeks after the transplant occurs in order to monitor development of acute and/or chronic rejection. In such an embodiment, the composition comprising the nanosensor can be administered multiple times to the subject before each bodily fluid sample is taken for analysis. In other embodiments, acute and/or chronic rejection can be monitored over the patient's lifetime after receiving the transplanted tissue, and thus may occur months to years to decades after receiving the transplanted tissue. In some embodiments, the monitoring may be triggered by a clinical change or symptom development, such as clinical signs of graft function decline. In such embodiments, the monitoring may occur for hours to weeks to months after onset of the clinical change or symptom development.

In any of the foregoing embodiments, the reference sample is a sample taken from the same subject prior to the transplant, while in other embodiments the reference sample is a sample taken from a person of similar physical characteristics as the subject (e.g., BMI-, age-, and gender-matched person who is not undergoing a transplant, does not require transplant surgery, and/or does not have an immune disorder as determined by standard examination and diagnostic methods). In some embodiments, the reference sample provides a control level of the target protease activity. If the subject is determined to be acutely and/or chronically rejecting the transplanted tissue, therapeutic and/or prophylactic compositions and/or methods can be employed to treat or prevent the acute and/or chronic rejection. Such therapeutic compositions and/or methods include, for example and not limitation, salvage therapy with thymoglobulin and steroids, immunosuppression therapies (such as for example and not limitation, anti-inflammatory drugs (cortisol, prednisone, fludrocortisone dexamethasone, acetate), anti-proliferatives (cyclophosphamide, methotrexate, azathioprine, mytomycin C)), and T cell targeted therapies (cyclosporine, tacrolimus, sirolimus, thymoglobulin, OKT3, antithymocyte globulin, Basiliximab, Belatacept, Abatacept). If the subject is determined to have or be likely to have an immune condition related to T cell cytotoxicity, therapeutic and/or prophylactic compositions and/or methods can be employed to treat or prevent the immune condition, such as for example and not limitation, immunosuppression therapies (such as for example and not limitation, anti-inflammatory drugs (cortisol, prednisone, dexamethasone, fludrocortisone acetate), anti-proliferatives (cyclophosphamide, methotrexate, azathioprine, mytomycin C)), and T cell targeted therapies (cyclosporine, tacrolimus, sirolimus, thymoglobulin, OKT3, antithymocyte globulin, Basiliximab, Belatacept, Abatacept).

In any of the foregoing embodiments, steps (d) and/or (e) and/or (f) (and repetitions of such steps) are performed by a computer, as described further herein. In certain embodiments, it may be convenient to prepare a report of results of the patient's identification. Thus, certain embodiments of the methods of the disclosure comprise a further step of preparing a report containing results from the identification, wherein said report is written in a computer readable medium, printed on paper, or displayed on a visual display. In certain embodiments, it may be convenient to report results of the determination to at least one entity selected from the group consisting of the subject, a guardian of the subject, a physician, a medical organization, and a medical insurer. In other embodiments, it may be convenient to report prognosis, results of monitoring, and/or efficacy of treatment and/or prophylactic methods to such entity.

In any of the foregoing methods, the method may further comprise treatment and/or prophylaxis of patients determined to have, or be at risk for having, acute or chronic rejection or immune conditions related to T cell cytotoxicity (e.g., autoimmune diseases, GVHD, etc).

Alternatively, the method of treatment and/or prophylaxis may comprise detection of the biomarkers and their use in the described algorithm to identify patients having or being at risk of having severe or lethal GVHD, and initiating treatment and/or prophylaxis based on the identification, or being suitable for undergoing such therapies.

In some embodiments, the treatment and/or prophylaxis comprises administration of appropriate therapeutically effective pharmaceutical compositions and/or use of appropriate therapeutically effective methods.

Non-limiting examples of the inflammatory and autoimmune diseases treatable by the methods of the present disclosure include, e.g., inflammatory bowel disease (IBD), graft versus host disease (GVHD), ulcerative colitis (UC), Crohn's disease, diabetes (e.g., diabetes mellitus type 1), multiple sclerosis, arthritis (e.g., rheumatoid arthritis), Graves' disease, lupus erythematosus, systemic lupus erythematosus (SLE), rheumatoid arthritis (RA), autoimmune myopathies, Sjogren's syndrome (SS), vasculitis, scleroderma, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions, autoimmune neuropathies, etc.

It is contemplated that when used to treat various diseases, the compositions and methods of the present disclosure can be combined with other therapeutic agents suitable for the same or similar diseases. Also, two or more embodiments of the disclosure may be also co-administered to generate additive or synergistic effects. When co-administered with a second therapeutic agent, the embodiment of the disclosure and the second therapeutic agent may be simultaneously or sequentially (in any order). Suitable therapeutically effective dosages for each agent may be lowered due to the additive action or synergy.

As a non-limiting example, the disclosure can be combined with other therapies that block inflammation (e.g., via blockage of IL1, INFa/B, IL6, TNF, IL13, IL23, etc.).

The compositions and methods of the disclosure can be also administered in combination with an anti-tumor antibody or an antibody directed at a pathogenic antigen or allergen.

The compositions and methods of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The inhibitory treatments of the disclosure can be also combined with other treatments that possess the ability to modulate NKT function or stability, including but not limited to CDId, CD1d-fusion proteins, CDld dimers or larger polymers of CDId either unloaded or loaded with antigens, CD1d-chimeric antigen receptors (CDId-CAR), or any other of the five known CD1 isomers existing in humans (CDla, CD1b, CDlc, CDle), in any of the aforementioned forms or formulations, alone or in combination with each other or other agents.

Therapeutic methods of the disclosure can be combined with additional immunotherapies and therapies. For example, when used to aid in treating cancer, the methods and compositions of the disclosure can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the disclosure include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the methods and compositions of the disclosure can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

The compositions of the disclosure can comprise a carrier and/or excipient. While it is possible to use a compound of the present disclosure for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in *Remington: The Science and Practice of Pharmacy*. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, sterilized human milk, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Those of relevant skill in the art are well able to prepare suitable solutions.

In one embodiment of any of the compositions of the disclosure, the composition is formulated for delivery by a route such as, e.g., oral, topical, rectal, mucosal, sublingual, nasal, naso/oro-gastric gavage, parenteral, intraperitoneal, intravenous, intradermal, transdermal, intrathecal, nasal, and intracheal administration. In one embodiment of any of the compositions of the disclosure, the composition is in a form of a liquid, foam, cream, spray, powder, or gel. In one embodiment of any of the compositions of the disclosure, the composition comprises a buffering agent (e.g., sodium bicarbonate, infant formula or sterilized human milk). In one embodiment of any of the compositions of the disclosure, the composition is formulated for intravenous administration.

Administration of the compounds and compositions in the methods of the disclosure can be accomplished by any method known in the art. Non-limiting examples of useful routes of delivery include oral, rectal, fecal (by enema), and via naso/oro-gastric gavage, as well as parenteral, intraperitoneal, intravenous, intradermal, transdermal, intrathecal, nasal, and intracheal administration. The active agent may be systemic after administration or may be localized by the use of regional administration, intramural administration, or use of an implant that acts to retain the active dose at the site of implantation. The formulation can include added ingredients to improve palatability, improve shelf-life, improve absorption, impart nutritional benefits, and the like.

The useful dosages of the compounds and formulations of the disclosure can vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses can be effective to achieve a therapeutic effect. While it is possible to use a compound of the present disclosure for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in *Remington: The Science and Practice of Pharmacy*. Lippincott Williams & Wilkins (A. R. Gennaro edit. 2005). The choice of pharmaceutical excipient, diluent, and carrier can be selected with regard to the intended route of administration and standard pharmaceutical practice. Although there are no physical limitations to delivery of the formulations of the present disclosure, oral delivery is preferred for delivery to the digestive tract because of its ease and convenience, and because oral formulations readily accommodate additional mixtures, such as milk, yogurt, and infant formula.

Oral delivery may also include the use of nanoparticles that can be targeted, e.g., to the GI tract of the subject, such as those described in Yun et al., *Adv Drug Deliv Rev*. 2013, 65 (6): 822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon). Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance. In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent. If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Formulations suitable for parenteral administration include aqueous and nonaqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity, such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN®80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., *Remington's Pharmaceutical Sciences*, Mack Publishing Company, Easton, Pa., 15th Edition, 1975). The composition or formulation to be administered may, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances, such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an inhibitor of Nt5e or AIR is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution can be apportioned into vials for lyophilization.

Each vial can contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

The inventive composition or pharmaceutically acceptable derivatives thereof may be formulated as aerosols for application, e.g., by inhalation or intranasally (e.g., as described in U.S. Pat. Nos. 4,044,126, 4,414,209, and 4,364,923). These formulations can be in the form of an aerosol or solution for a nebulizer, or as a microfine powder for insufflation, alone or in combination with an inert carrier such as lactose. In such a case, the particles of the formulation can, by way of example and without limitation, have diameters of less than about 50 microns, such as less than about 10 microns.

The agents may be also formulated for local or topical application, such as for application to the skin and mucous membranes (e.g., intranasally), in the form of nasal solutions, gels, creams, and lotions.

Other routes of administration, such as transdermal patches are also contemplated herein. Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

Kits of the Invention

The present invention also provides kits useful in the practice of the methods of the invention. In some embodiments, these kits comprise detection reagents that specifically bind the nanosensors of the present invention, such as for example and not limitation, at least one of the detectable peptide sequences. The kits typically include a probe that comprises an antibody or nucleic acid sequence that specifically binds to polypeptides or polynucleotides of the invention, such as for example and not limitation, at least one of the detectable peptide sequences comprising the amino acid sequence of SEQ ID NOs 2-136, as well as genes encoding these sequences, and a label for detecting the presence of the probe. The kits may include several antibodies specific for, or polynucleotide sequences encoding, the polypeptides of the invention. The kits may further comprise control probes for detection of a control nucleic acid or a control protein in order to provide a control level of the nucleic acid or protein, and/or other standards or controls. The probe is optionally detectably labeled.

The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions for carrying out the assay may also be included in the kit. The assay may, for example and not limitation, be in the form of a Northern hybridization, sandwich ELISA or protein antibody array.

Reagents for detecting biomarkers of the present invention can be immobilized on a solid matrix such as a porous strip to form at least one detectable peptide sequence detection site. The measurement or detection region of the porous strip may include a plurality of sites containing an antibody or nucleic acid. A test strip may also contain sites for negative and/or positive controls. Alternatively, control sites can be located on a separate strip from the test strip. Optionally, the different detection sites may contain different amounts of immobilized antibodies or nucleic acids, e.g., a higher amount in the first detection site and lesser amounts in subsequent sites. Upon the addition of test sample, the number of sites displaying a detectable signal provides a quantitative indication of the amount of detectable peptide sequence present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences adapted to bind a nucleic acid sequence encoding a detectable peptide sequence comprising at least one of SEQ ID NOs 2-136. The substrate array can be on, e.g., a solid substrate or "chip". Alternatively, the substrate array can be a solution array.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs).

Alternatively (or in addition), a kit can include reagents for performing a hybridization assay for nucleic acid(s) and/or proteins. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include DNA or RNA isolation or purification means as well as positive and negative controls. Alternatively, the kit may include at least one container containing reagents for detection of electrophoresed proteins. Such reagents include those which directly detect proteins, such as Coomassie blue or other staining reagents including fluorescent staining agents, or those reagents directed at detecting labeled proteins. A kit can further include protein isolation or purification means as well as positive and negative controls. A kit can also include a notice associated therewith in a form prescribed by a governmental agency regulating the manufacture, use or sale of diagnostic kits. Detailed instructions for use, storage and trouble-shooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Such kits may also include components that preserve or maintain proteins, such as reagents that protect against protein degradation. Any of the compositions or reagents described herein may be components in a kit.

In some embodiments, the kit further comprises an apparatus for collecting a bodily fluid sample, e.g., a urine, blood, lymphatic fluid, saliva and/or plasma sample, from a subject. In other embodiments, the kit further comprises instructions for using the collection apparatus and/or the reagents comprising the kit.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more Controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, and the like.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

Thus, another aspect of the disclosure is a system that is capable of carrying out a part or all of a method of the disclosure, or carrying out a variation of a method of the disclosure as described herein in greater detail. Exemplary systems include, as one or more components, computing systems, environments, and/or configurations that may be suitable for use with the methods and include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. In some variations, a system of the disclosure includes one or more machines used for analysis of biological material (e.g., genetic material), as described herein. In some variations, this analysis of the biological material involves a chemical analysis and/or a nucleic acid amplification.

The computer may operate in a networked environment using logical connections to one or more remote computers, such as a remote computer via a network interface controller (NIC). The remote computer may be a personal computer, a server, a router, a network PC, a peer device or other common network node, and typically includes many or all of the elements described above relative to the computer. The logical connection between the NIC and the remote computer may include a local area network (LAN), a wide area network (WAN), or both, but may also include other networks. Such networking environments are commonplace in offices, enterprise-wide computer networks, intranets, and the Internet. The remote computer may also represent a web server supporting interactive sessions with the computer; or in the specific case of location-based applications may be a location server or an application server.

In some embodiments, the network interface may use a modem when a broadband connection is not available or is not used. It will be appreciated that the network connection shown is exemplary and other means of establishing a communications link between the computers may be used.

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

EXAMPLE 1. Development of the Disclosed Compositions and Methods of Use

Engineering synthetic biomarkers to sense GzmB activity

Figures 2A, 2B:
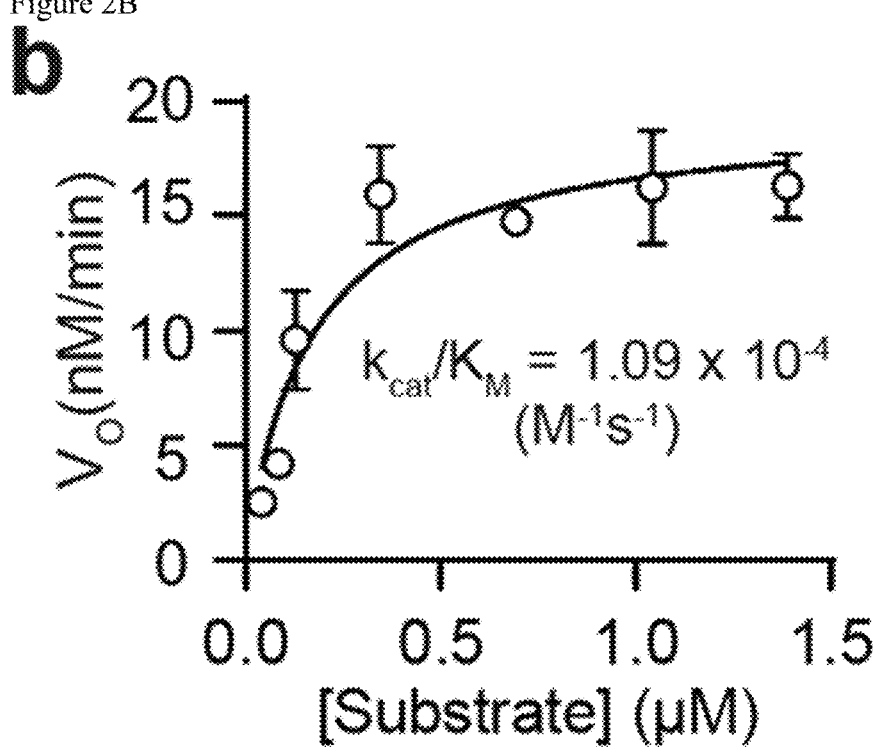
FIGS. 2A-2F. Synthetic biomarkers are sensitive and specific to proteolytic cleavage by GzmB.
Figures 6, 7A:
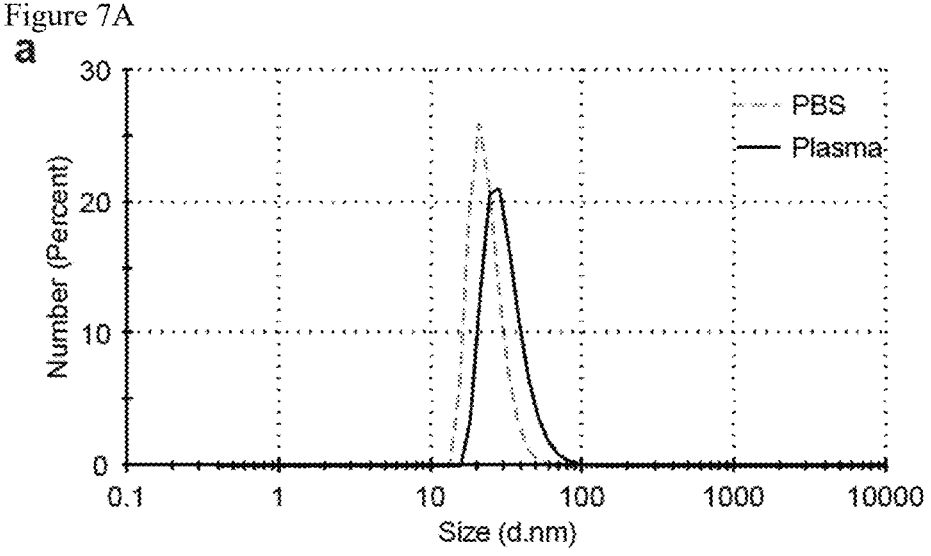
Figure 7B:
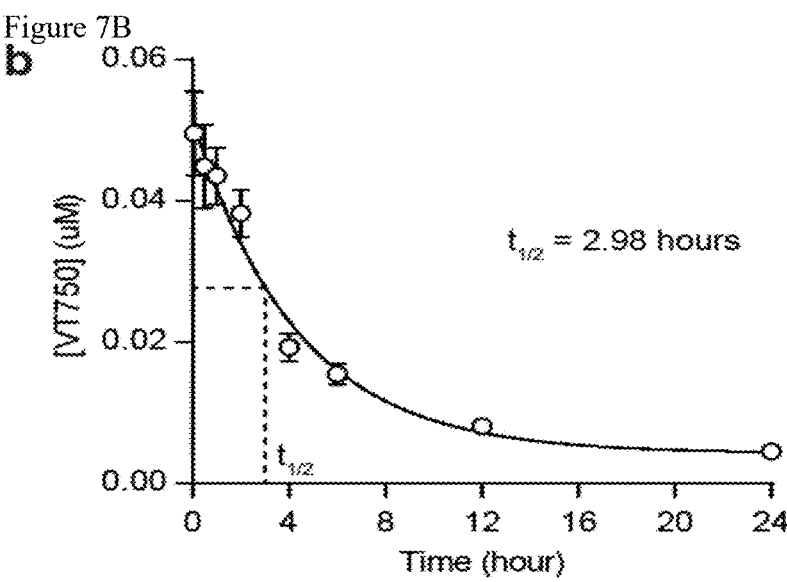

To sense cytotoxic activity of CD8 T cells, the synthetic biomarkers consisted of a nanoparticle core conjugated with peptide substrates specific for Granzyme B (GzmB) (FIG. 2A). The use of a nanoparticle chaperone achieved two goals: it extended the half-life of surface-conjugated peptides by preventing renal clearance, and through passive targeting, accumulated in tissues with fenestrated endothelium including secondary lymphoid organs (e.g., spleen, lymph nodes) as well as sites of inflammation as occurs during graft rejection (22, 23). The inventors chose iron oxide nanoparticles (IONP) because they are FDA-approved for clinical use including as anemia therapies, contrast agents for imaging, and thermal ablation (24). The second component of the synthetic biomarkers was a peptide substrate designed to sense a target protease of interest, which in this case is GzmB, the key cytotoxic effector protease secreted by CD8 T cells (25). These substrates were further modified with a reporter which allows detection of cleaved peptide fragments in urine. While the present compositions used a fluorescent reporter to analyze urine samples with a simple fluorescent assay, peptide substrates can be labelled with different barcoded technologies such as isobaric mass tags for multiplexing analysis, ligand encoded reporters for point of care paper-based tests (17-20). To ensure biocompatibility and improved circulation half-life of synthetic biomarkers, the inventors decorated nanoparticle surface with polyethylene glycol (PEG), which reduces nanoparticle uptake by the reticuloendothelial system (RES) (26). Hydrodynamic size profiling by dynamic light scattering (DLS) showed that PEGylated nanoparticles were stable in both PBS and mouse plasma, with the Z-average in plasma was 47 nm (FIG. 7A). The circulation half-life of synthetic biomarkers was ~3 hours in mice, which was consistent with previously reported values for clinically approved IONPs (FIG. 7B) (27).

Figure 2C:
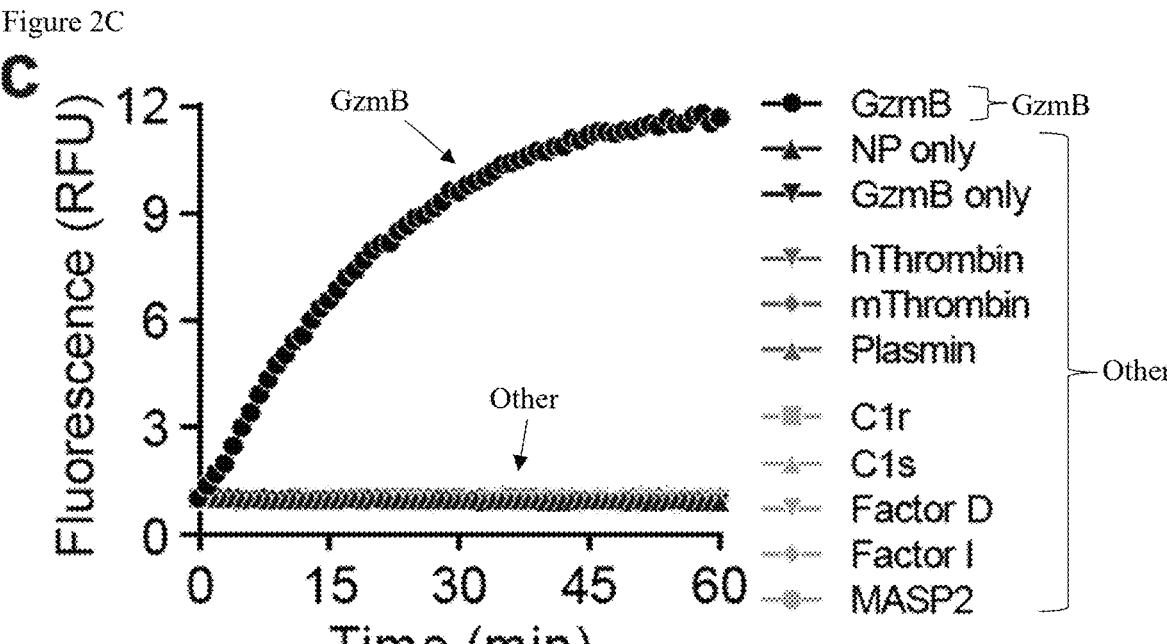
Figure 2D:
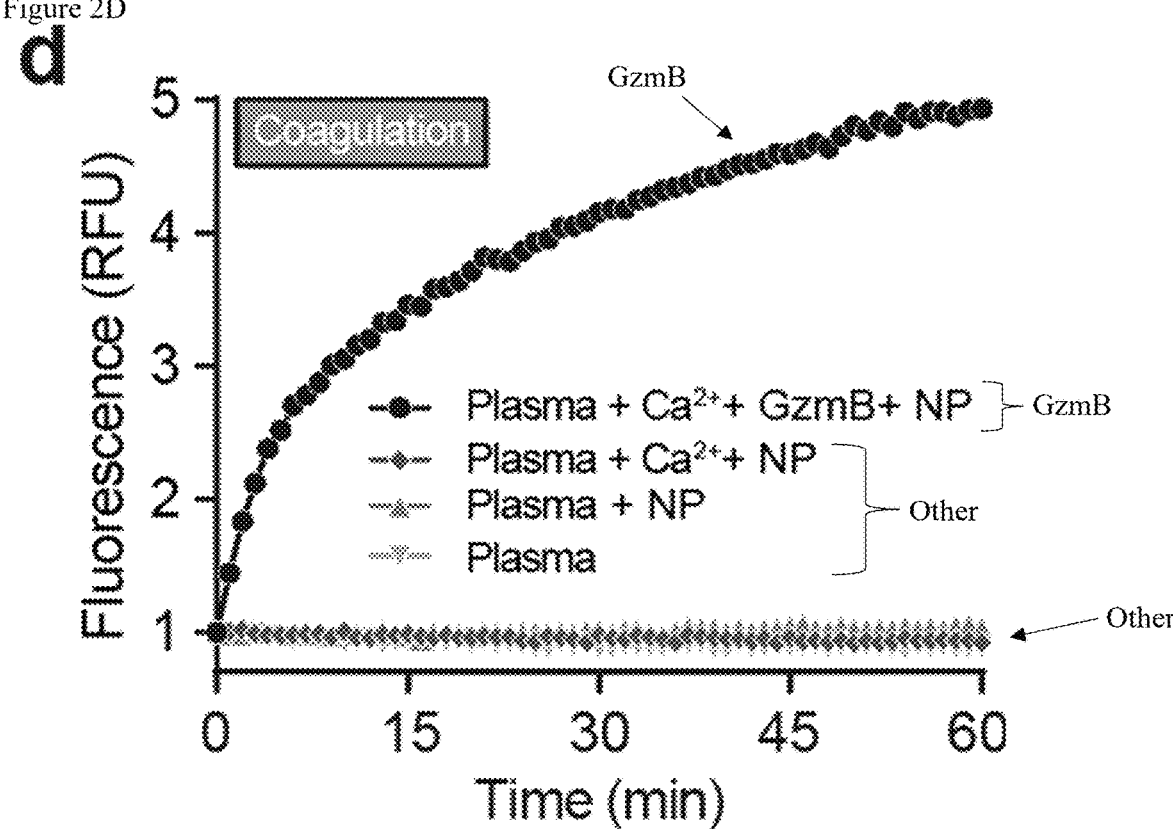
Figure 2E:
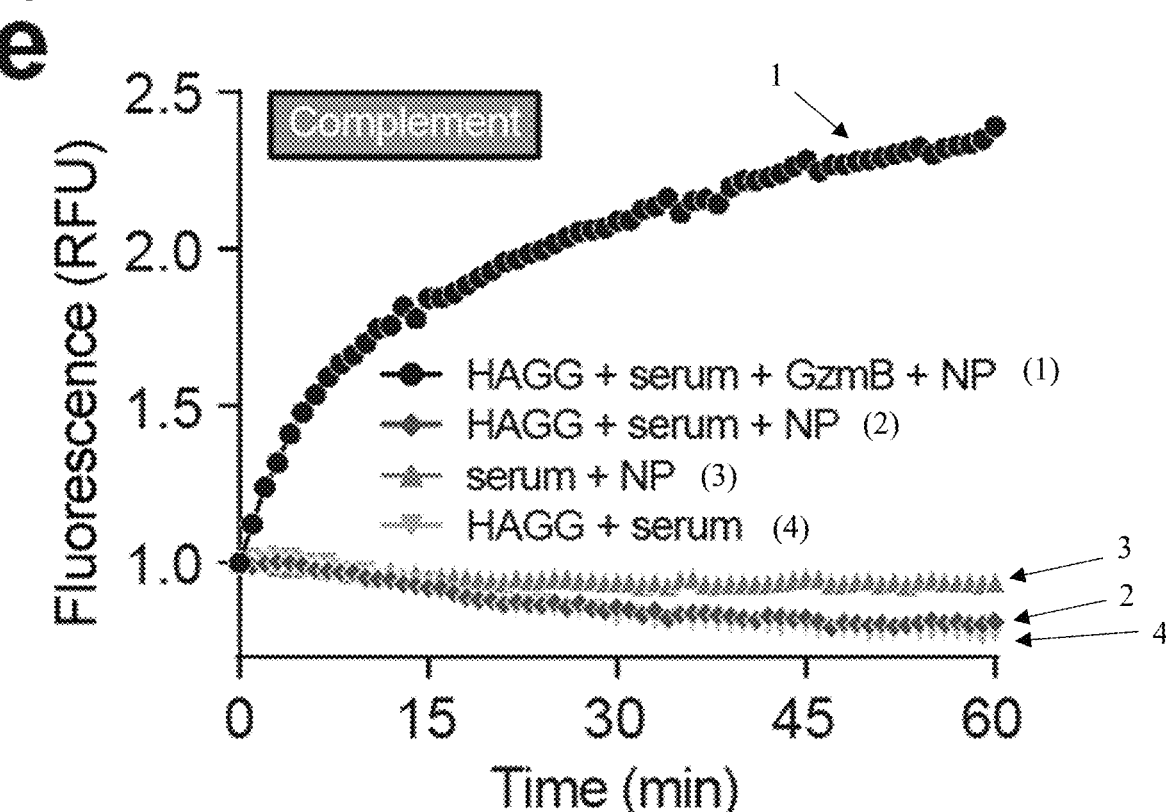
Figure 2F:
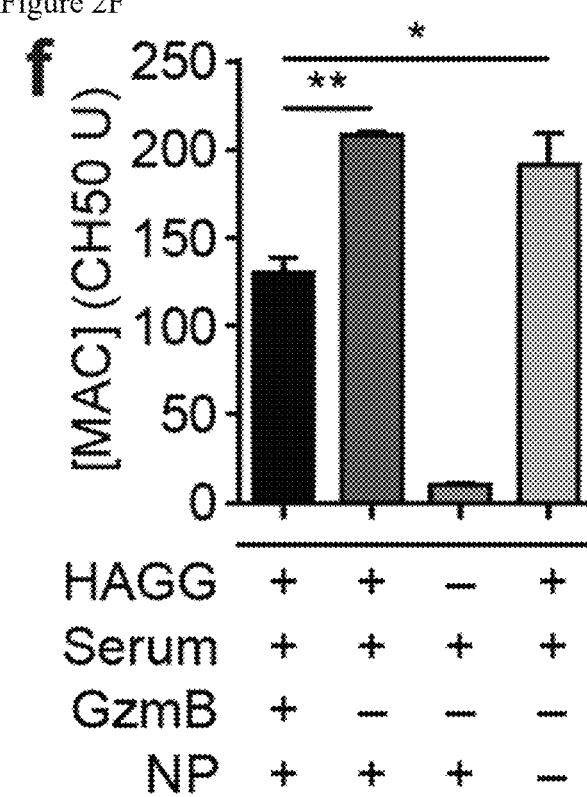

The inventors first set out to identify peptide substrates that are sensitive to cleavage by recombinant GzmB. From published literature (28-31), 13 candidate substrates (FIG. 6) were pooled, each spanning 6-8 amino acids in length and containing conserved residues isoleucine at position P4 and aspartic acid at P1—the position immediately N-terminal of the cleavage site. The inventors varied the amino acids at other locations, length of the substrate, and flexible spacers on both sides of the designed substrate. From a library, the inventors identified the sequence AIEFDlSGc (SEQ ID NO: 24) (small case letters are amino acids synthesized as d-stereoisomers) as the substrate that produced the highest rate of cleavage by recombinant GzmB (FIG. 2A, FIG. 6). Michaelis-Menten kinetics analyses were performed to assess the efficiency of GzmB cleavage of substrate on nanoparticle surface. Fitted $k_{cat}$/KM was $1.09 \times 10^4 M^{-1}s^{-1}$, similar to reported values of GzmB cleaving free substrates of similar sequences (FIG. 2B) (28, 31), which shows that presentation of substrates on nanoparticle surface does not affect GzmB cleavage. In vivo, the coagulation and complement cascades contain ubiquitous circulating proteases that can degrade the synthetic biomarkers. Therefore, to test specificity of the substrate for GzmB, the inventors studied synthetic biomarker cleavage by key recombinant proteases as well as activated coagulation and complement cascades in blood samples. Increases in fluorescent intensity were observed only in samples containing recombinant GzmB (FIGS. 2C, 2D, and 2E). Furthermore, the formation of membrane attack complex (MAC) was not detected when synthetic biomarkers were incubated with serum samples, indicating that the synthetic biomarkers did not activate the complement cascade via interaction with foreign surface (32) (FIG. 2F). Overall, these data showed that synthetic biomarkers are specific for GzmB and are not activated by proteases in the coagulation and complement cascades.

Synthetic Biomarkers Amplify Cytotoxic Signals from Alloreactive T Cells

Next, the inventors sought to investigate the use of synthetic biomarkers to sense GzmB during cytotoxic activity by recipient T cells against donor target cells expressing alloantigens. GzmB is the central effector protease that CD8 T cells utilize to kill target cells. In activated T cells, GzmB is upregulated and contained in cytolytic granules, and upon TCR-pMHC engagement, these granules are lysed to release GzmB that enters target cells through perforin-mediated pore formation (25). Inside target cells, GzmB serves as potent initiator of the apoptosis cascade by either direct cleavage to activate proapoptotic protease Caspase 3 or induction of mitochondrial disruption (25, 33). Previously, elevated levels of GzmB in blood has been used to monitor the efficacy of CAR T cell therapy against B cell leukemia (34). In solid tumors, GzmB expression in longitudinal tumor biopsies could be used to differentiate non-responders from responders to immune blockade therapies (35). In transplant rejection, presence of GzmB mRNA transcript in patient urine samples has been shown to correlate to episodes of acute rejection (13, 14).

Figures 3E, 3F:
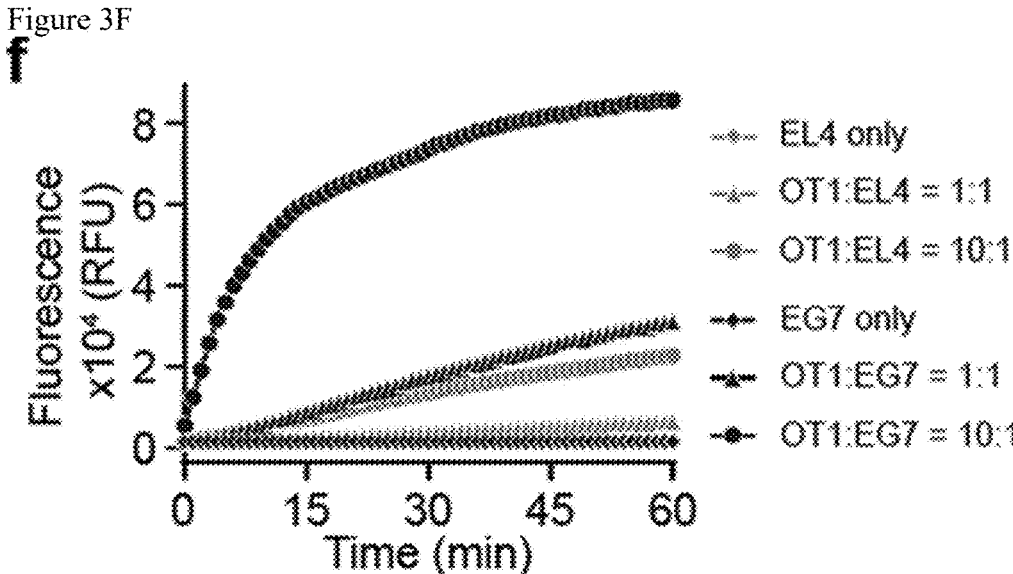
(FIG. 3E) Synthetic biomarkers sense GzmB secreted in cocultures of OT1 T cells and EG7-OVA target cells.
(FIG. 3F) T cell activity assays showing fluorescence of synthetic biomarkers in co-culture supernatants of OT1 T cells with EG7-OVA or EL4 target cells.
Figures 3G, 3H:
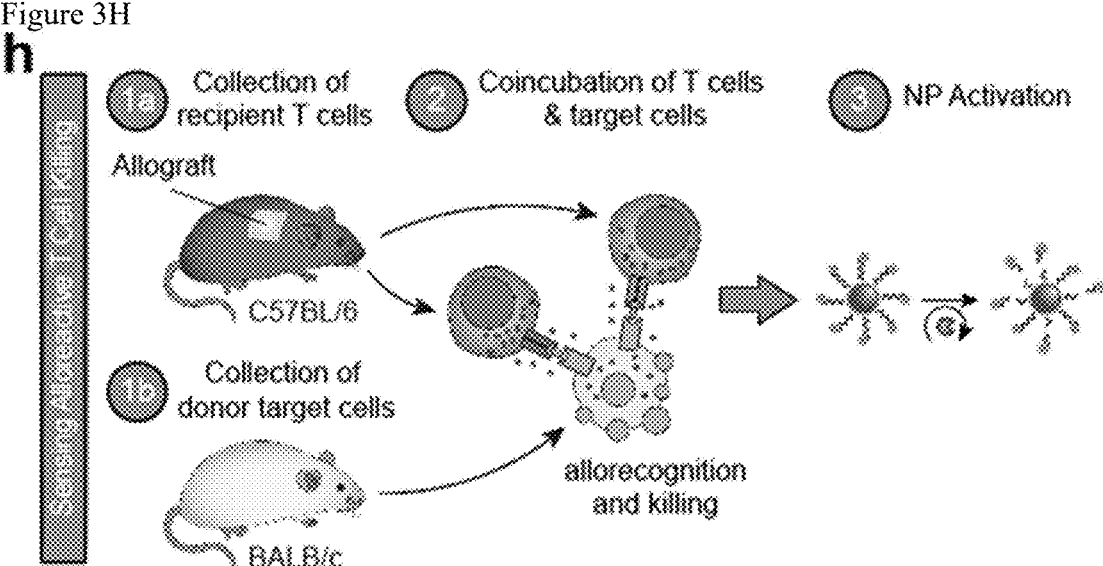
(FIG. 3G) Quantified plot of T cell activity assays showing fitted value of initial cleavage velocities.
(FIG. 3H) Synthetic biomarkers sense GzmB secreted in during alloreactive T cell killing.
Figure 8A:
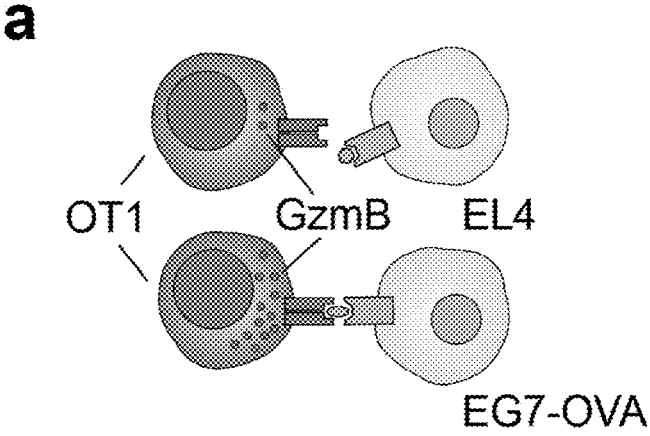
FIGS. 8A-8B. Upregulation of intracellular GzmB expression in transgenic T cells (FIG. 8A) Activated OT1 CD8 T cells upregulated GzmB expression after coincubation with EG7-OVA target cells but not with EL4 target cells.
Figure 8B:
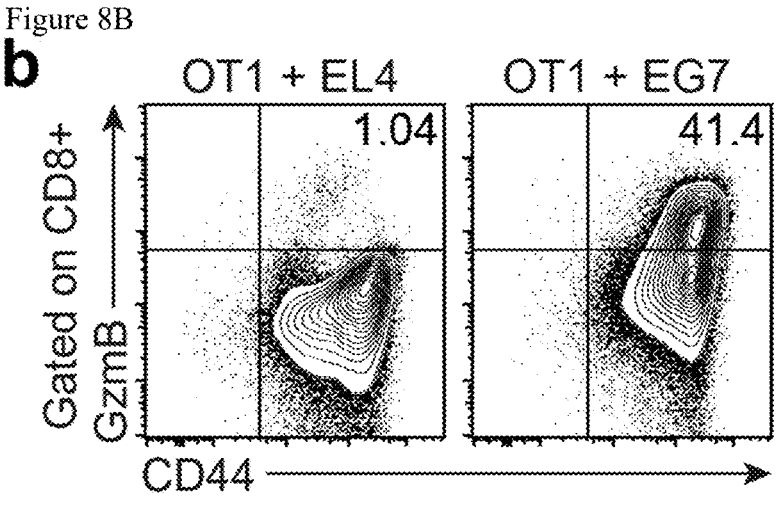

To test synthetic biomarkers in the context of T cell mediated cytotoxicity, the inventors used transgenic OT-1 T cells, which recognize the peptide epitope SIINFEKL (SEQ ID NO: 145) from chicken ovalbumin (OVA), in a T cell killing assay (36). To verify intracellular expression of GzmB in plate-activated OT-1 T cells, the inventors performed flow analysis and confirmed that GzmB levels were elevated in OT-1 T cells after engagement with EG7-OVA target cells compared to EL4 controls (FIGS. 8A-8B). To quantify the cleavage activity of GzmB, a fluorogenic assay in which a substrate can fluoresce upon cleavage by active GzmB was used to measure GzmB activity inside target cells (FIG. 3A). It was observed that GzmB activity inside EG7-OVA cells was 5 to 7-fold higher than EL-4 cells when coincubated with OT1 T cells at T cell to target cell ratios from 1:1 to 10:1 (* P, n=3, FIGS. 3B, 3C). Because synthetic biomarkers are designed to monitor extracellular protease activity, the amount of secretory GzmB was measured and significantly elevated level of GzmB in coculture supernatant of OT1 T cells and EG7-OVA cells versus EL4 controls was detected, with a 10-fold improvement observed at T cell to target cell ratio of 10:1 (** P, n=3, FIG. 3D). The synthetic biomarkers amplified cytotoxic signal from transgenic OT1 T cells killing EG7-OVA target cells (FIGS. 3E, 3F). Furthermore, the initial velocity of probe activation was strongly correlated to the amount of secretory GzmB in coculture supernatant (FIG. 3D, 3G). After showing that the synthetic biomarkers could sense transgenic T cell killing with only one unique TCR-pMHC interaction, the inventors investigated their ability to sense alloreactive T cell killing, which is a polyclonal T cell response against alloantigens. For this experiment, splenocytes from donor BALB/c mice were co-incubated with splenocytes and lymphocytes from recipient C57BL/6 mice bearing skin grafts before adding synthetic biomarkers to monitor cytotoxic activity (FIG. 3H). Increased activation kinetics of synthetic biomarkers in cocultures containing T cells from mice bearing allografts was detected (FIG. 3I). Thus, the engineered GzmB-sensing synthetic biomarkers are useful for detection of alloreactive T cell killing.

GzmB is Upregulated at the Onset of Acute Cellular Rejection

During ACR episodes, host CD8 T cells activate through direct or indirect pathways by interaction with donor- or host-derived antigen presenting cells (APC) respectively, expand rapidly in secondary lymphoid organs (e.g., spleen and lymph nodes), and secrete cytotoxic granules containing GzmB to mediate allograft rejection (3, 4). Currently, the core biopsy is used to examine for histological hallmarks of ACR-which directly result from T cell activity-including T cell infiltration, inflammatory cytokines, morphological changes, tissue remodeling (6). In contrast to these morphological biomarkers, which are downstream and lack predictive value, the ability to detect proteases that drive disease pathology can allow anticipation of patient trajectory, such as monitoring MMP activity in liver fibrosis progression and regression (17-21).

Figures 4C, 4D, 4E, 4F:
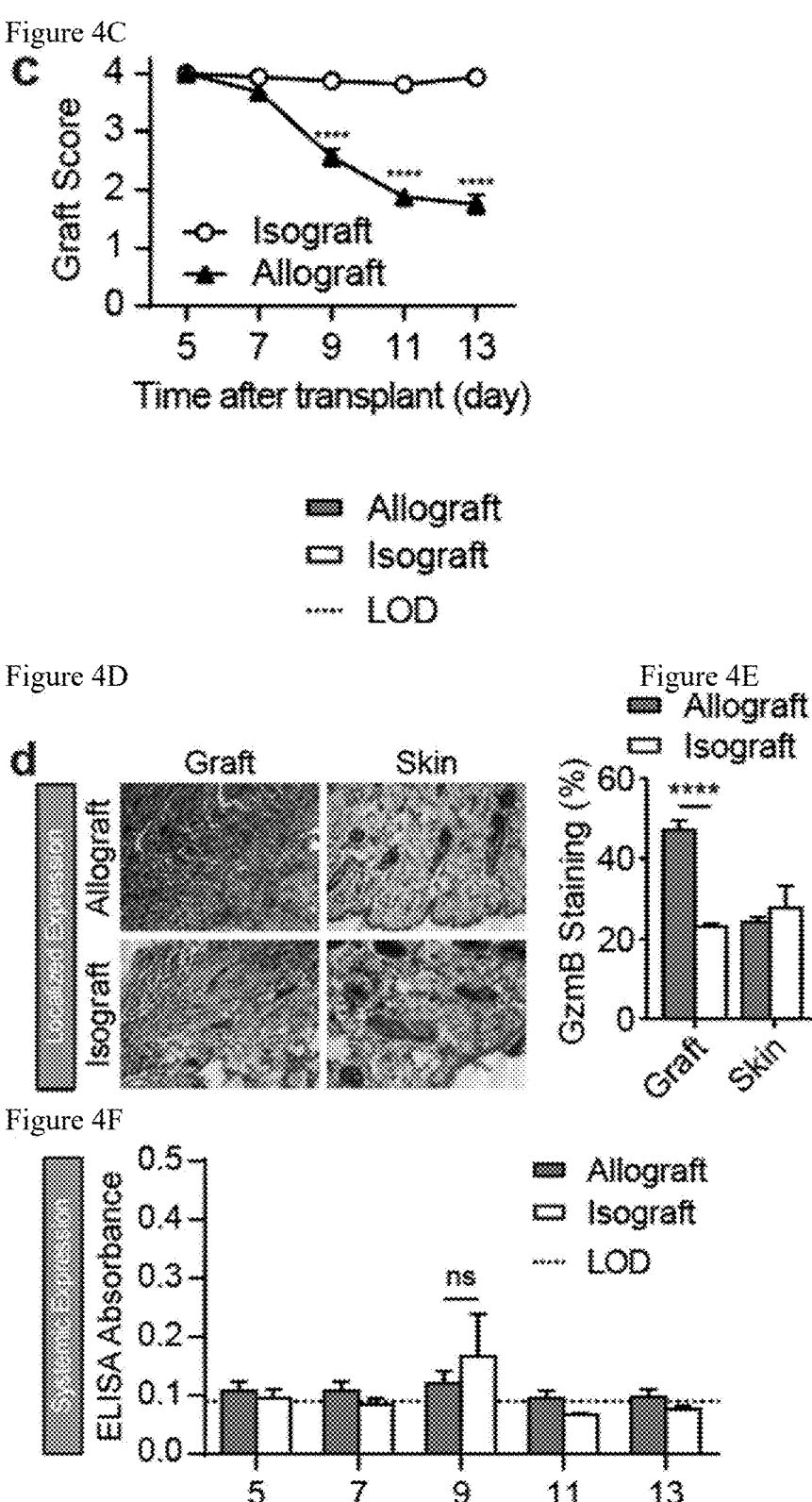
Figure 9:
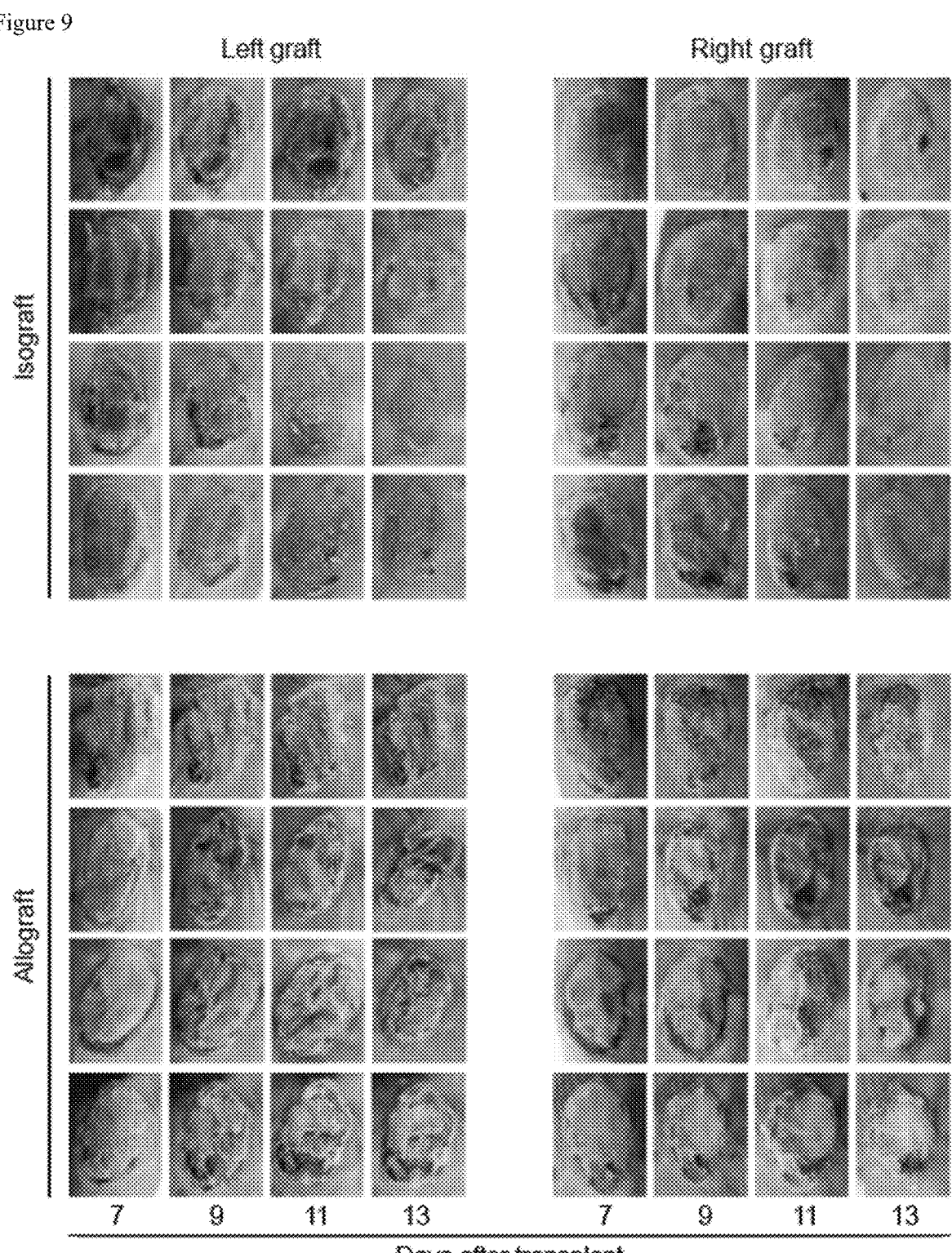
Figures 10A, 10B, 11:
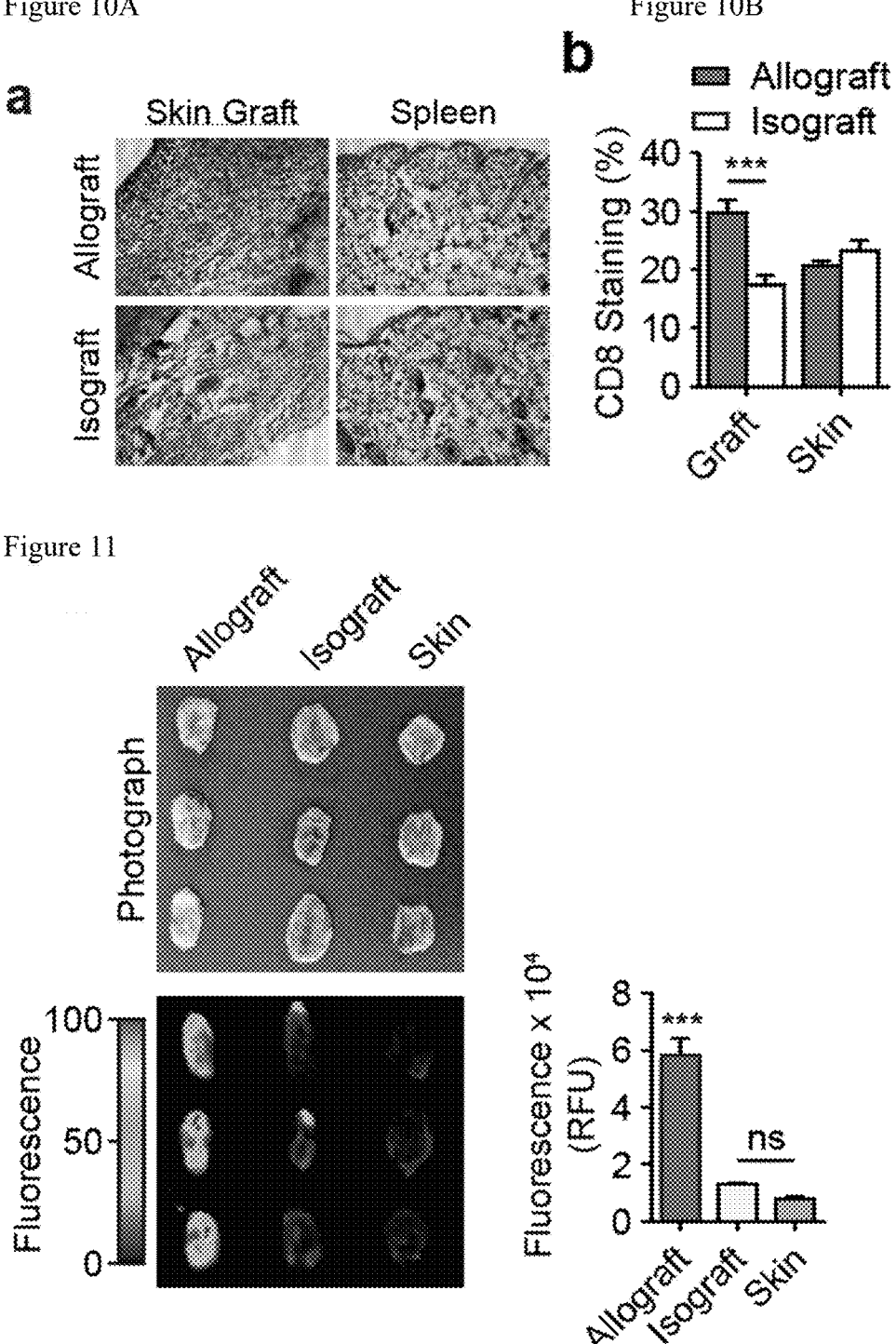
Figure 14B:
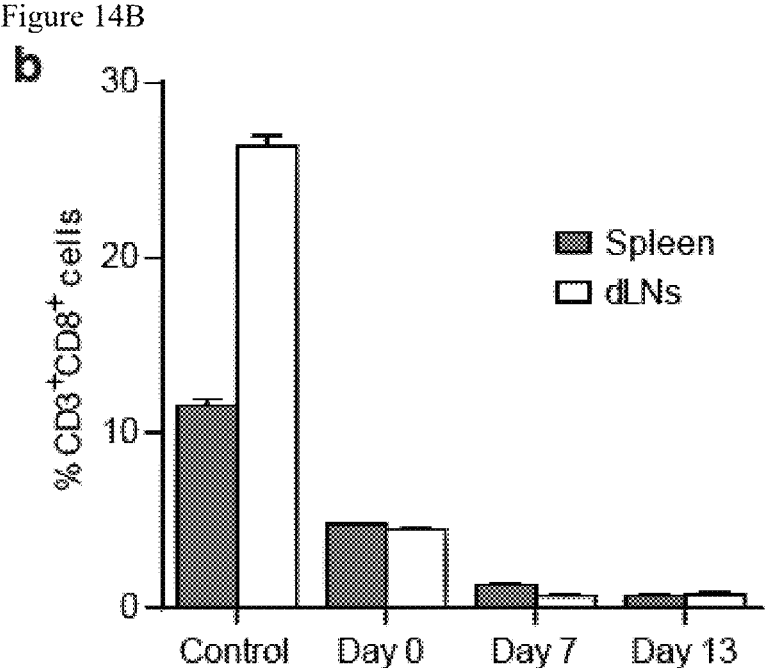

First, the inventors sought to validate the expression of GzmB at the onset of acute rejection using the well-established BALB/c to B6 mouse model of skin transplantation (FIG. 4A). To quantify skin graft health, the inventors assigned a score of 4 for healthy grafts, a score of 0 for rejected grafts, and intermediate scores based on features such as the ratio of viable to necrotic skin and the presence of ulcerations or scabs. Nine days after transplant, allograft scores began to decrease significantly compared to isograft controls (2.6 vs. 3.9, P<0.0001; FIGS. 4B, 4C and FIG. 9) and reached an endpoint when grafts were completely rejected two weeks post-transplant. To investigate localized expression of GzmB during rejection, the inventors stained skin grafts and tissue sections and found significant upregulation of CD8 and GzmB in skin allografts (FIG. 4D, FIGS. 10A, 10B). By contrast, GzmB was not detected in plasma samples throughout the course of rejection (FIG. 4E). To investigate the kinetics of GzmB expression relative to the rate of graft rejection, the inventors analyzed CD8 T cells in splenocytes and lymphocytes from mice bearing skin grafts before and during the peak of rejection (day 5 to day 9). It was found that GzmB levels in CD8 T cells expressing the activation marker CD44 were first elevated on day 7 when allograft and isograft scores were indistinguishable (FIG. 4C), and continued increasing throughout the course of allograft rejection (FIG. 4F). Taken together, these data have shown that GzmB expression is localized to skin allografts and secondary lymphoid organs and upregulated before the onset of acute rejection.

Urine Analyses Predict Early Acute Rejection of Skin Allografts

During the onset of acute rejection, damaged associated molecular patterns (DAMPs) trigger the release of proinflammatory cytokines (e.g., TNF-alpha, IL-6) by innate immune cells that increase vessel permeability to enhance local blood flow and immune cell infiltration (4, 22, 23). Previously, this localized vasodilation was exploited to deliver nanomedicines to inflammatory tissues including atherosclerotic plaques and tumors (37-39). Thus, the inventors sought to quantify the extent by which synthetic biomarkers accumulate in allografts during inflammation and rejection relative to healthy tissues. The inventors intravenously administered surface-labelled nanoparticles to C57BL/6 mice transplanted with both skin allografts and isografts on the same recipient at the onset of rejection (day 7) to allow quantification by full-body fluorescent imaging (FIG. 5A). Whereas both skin graft scores were statistically identical (FIG. 4C), the inventors found a 6-fold higher accumulation of nanoparticles in allografts compared to isografts or healthy skin (*** P, n=3) (FIGS. 5B, 5C, and FIG. 11). This result was further supported by biodistribution studies, where in addition to nanoparticle localization in skin allografts, the inventors also observed passive targeting to organs with fenestrated endothelium such as liver and secondary lymphoid organs (spleen, draining lymph nodes) over other major organs (brain, heart, kidney, lung) (FIG. 5D and FIG. 12). This transport of nanoparticles across porous vasculature is consistent with well-established studies in nanomedicine (37, 39). To confirm size dependent filtration into urine, either labelled free peptides or labelled nanoparticles were administered to skin graft mice. It was observed that only free peptides cleared into urine (FIGS. 13A-13D).

Figure 5H:
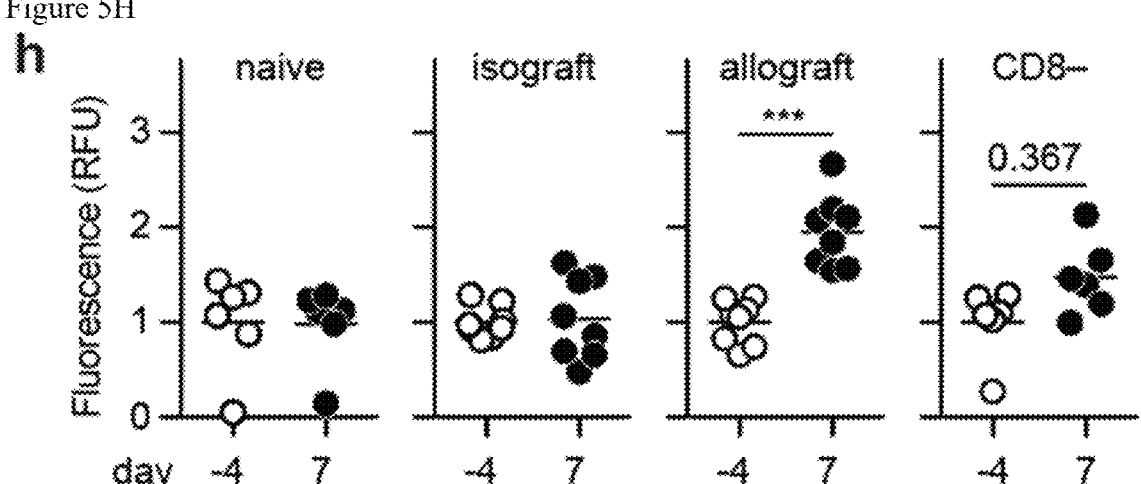
(FIG. 5H) Normalized urine fluorescent signals after administration of synthetic biomarkers to naïve mice, isograft mice, allograft mice, and mice bearing allografts after depletion of CD8 T cells (one way ANOVA and Tukey's post test, n=6-8).
Figure 5I:
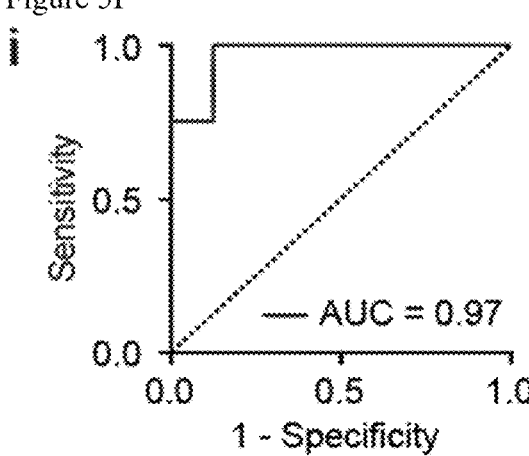

Last, the inventors investigated the ability of synthetic biomarkers to predict the onset of ACR by shedding a fluorescent reporter into urine (FIG. 5E). To track in vivo GzmB cleavage activity, on day 7 synthetic biomarkers were administered to mice bearing skin grafts and several organs of interest were collected for near infra-red (NIR) imaging. GzmB activity in allograft mice, with respect to isograft mice, was 3-fold higher in the kidney due to rapid clearance of the small fluorophores after cleavage (*P, n=3-4, FIG. 5F). Using the same probe, the inventors performed full body imaging and only detected fluorescent signals from the bladders of allograft mice (FIG. 5G). Next, synthetic biomarkers were administered to mice bearing skin grafts before (day-4) and after (day 7) transplant surgeries were performed to establish a diagnostic metric via urine fluorescence. Pre-graft urine signals served as an internal baseline for each mouse to control for urine clearance rate and confounding variables associated with transplant surgery. The inventors did not detect significant elevation in post-graft urine signals, with respect to pre-graft signals, from naïve mice, isograft mice, and allograft mice depleted of CD8 T cells. In contrast, post-graft urine signals from allograft mice significantly elevated by more than 2-fold when compared to pre-graft signals (*** P, n=7, FIG. 5H). Meanwhile, graft scores of allografts and isografts were still undifferentiated (FIG. 4C). Receiver-operating-characteristic (ROC) analysis showed that the synthetic biomarkers could distinguish between accepting isografts and rejecting allografts with an area under the curve (AUC) of 0.969 (95% CI was 0.892 to 1.045) (FIG. 5I). This AUC value demonstrated greatly improved diagnostic power over other promising noninvasive diagnostic platforms, where AUC values fall between 0.7 and 0.9. Overall, noninvasive administration of GzmB sensing synthetic biomarkers allowed for prediction of ACR in a skin graft mouse model of transplant rejection and provided a promising diagnostic platform to replace tissue biopsy.

DISCUSSION

In transplantation medicine, the core biopsy is considered the "gold" standard for diagnosing anti-graft activity. However, the biopsy is associated with significant patient morbidity and sampling error. Thus, there is a clinical need to develop noninvasive, sensitive, and specific diagnostics that accurately predict acute rejection episodes. Herein are described activity-based nanosensors consisting of a nanoparticle core decorated with peptide substrates to sense the proteolytic activity of GzmB during antigen-specific CD8 T cell killing. In skin graft mouse models, synthetic biomarkers passively accumulate in allograft tissue during T-cell mediated rejection where they are cleaved by GzmB secreted by alloreactive T cells. These cleavage events trigger a pharmacokinetic switch where the cleaved peptide fragments, due to their small size, are filtered into urine to produce a noninvasive signal that predicts the onset of ACR.

The use of a nanoparticle chaperon increases circulating half-life of substrate peptides which otherwise are cleared from the body by renal filtration within minutes after IV administration. This enhanced pharmacokinetics enables passive delivery of peptides to inflamed allograft tissues, which are active areas of T-cell mediated acute rejection. Though passive accumulation of synthetic biomarkers is significant in skin allograft, which is a thin and small piece of tissue, significantly higher accumulation would occur in allografts of larger and more solid organs. Furthermore, it is possible to functionalize the nanoparticle scaffolds with organ-specific ligands to further enhance delivery and detection signals. The inventors used IONPs as the carrier of substrate peptides because they are FDA-approved and have great translation potential. These synthetic biomarkers are well tolerated upon repeated administration and have relatively short circulation half-life (3 hours), which allows multiple time point sampling to more accurately monitor progression of graft heath. Besides using IONPs, substrate peptides can be coated on other nanoscale scaffolds (e.g., PEG, protein-based carriers, PLGA) to tune their pharmacokinetics and presentation to optimize urine signals. While upregulation of GzmB has been detected in patients with acute rejection episodes, this expression is mostly localized to disease tissues, making in vitro diagnosis with a simple blood draw especially challenging. The invented synthetic biomarkers monitor in vivo GzmB activity at sites of active rejection and offer two potential methods of amplifying detection signals: (1) enzymatic turnovers allows one endogenous copy of GzmB to cleave thousands of synthetic substrate peptides while (2) renal clearance allows concentration of this disease signal in a small urine volume.

The inventors have developed a sensitive probe to detect the activity of GzmB, which is the key effector protease during T cell cytotoxicity. Previous studies have found a correlation between elevations of GzmB RNA transcripts in patient urine samples to acute allograft rejection episodes (13, 14). Instead of looking at GzmB abundance that does not differentiate between Serpin-bound (inactive) from active form of GzmB (15, 40), these synthetic biomarkers sense proteolytic activity of GzmB as a predictor for acute cellular rejection. A single biomarker reflective of a fundamental cellular process or mechanism can be broadly applied to detect or monitor a range of disease conditions. For example, fluorodeoxyglucose positron-emission tomography (FDG-PET) imaging, which only monitors glucose metabolism, are valuable in diagnosis, staging, and monitoring treatments of cancers and neurodegenerative disorders (41-43), Likewise, synthetic biomarkers that monitor GzmB activity can be used in the diagnosis of immune conditions related to T cell cytotoxicity which include graft versus host disease (GvHD), autoimmune diseases, and immuno-oncology. Moreover, the sensitivity of a single biomarker is dependent on the setting in which it is recommended for clinical use. For example, monitoring the levels of a single biomarker over time in high-risk patients can significantly increase detection sensitivity. For example, prostate-specific antigen (PSA) lacks specificity and sensitivity for general population screening; however, it is an excellent biomarker when used in high-risk patients such as monitoring recurrent after radiation therapies (44).

Moving forward, this platform can be readily expanded into a multiplex probe set using mass barcodes (17) to obtain a protease signature that reflects a more complete picture of patient pathology. Multiplexing analysis improves diagnostic specificity by simultaneous monitoring the activities of disease-associated proteases on the background of T cell mediated cytotoxicity. This capability can be valuable in differentiating acute organ rejection from conditions such bacterial infections, viral infections, and cancers, which all involve T cell cytotoxicity but are also driven by unique protease subsets (bacterial proteases, viral proteases, and tumor-derived proteases) (45-47). Furthermore, it is possible to distinguish acute rejection, which is mediated by T cell effector proteases (GzmB), from chronic rejection, which is driven by complement (Cls, Clr) and fibrotic (ADAMTS1) proteases (5, 10, 48, 49). The ability to profile protease signatures at various stages of rejection might allow researchers to learn more about unique disease mechanisms to develop better therapies that prolong graft survival and improve patient outcomes.

MATERIALS AND METHODS

NP synthesis and characterization

Aminated IONPs were synthesized in house per published protocol. GzmB-sensing peptides were synthesized by Tufts University Core Facility peptide synthesis service. Aminated IONPs were first reacted to the biofunctional crosslinker Succinimidyl Iodoacetate (SIA; Thermo) for 2 hours at room temperature (RT) and excess SIA were removed by buffer exchange using Amicon spin filter (30 kDa, Millipore). Sulfhydryl-terminated peptides and Polyethylene Glycol (PEG; LaysanBio, M-SH-20K) were mixed with NP-SIA (90:20:1 molar ratio) and reacted overnight at RT in the dark to obtain fully conjugated synthetic biomarkers. Synthetic biomarkers were purified on a Superdex 200 Increase 10-300 GL column using AKTA Pure FPLC System (GE Health Care). Ratios of FITC per IONP were determined using absorbance of FITC (488 nm, $\varepsilon$=78,000 cm-1M-1) and IONP (400 nm, $\varepsilon$=2.07×10^6 cm$^{-1}$M$^{-1}$) measured with Cytation 5 Plate Reader (Biotek). DLS measurements of synthetic biomarkers were done in PBS or mouse plasma at RT using Zetasizer Nano ZS (Malvern). For half-life characterization, the inventors administered via IV 20 µg of labelled IONPs to CFW Mice (Charles River). At several time points following NP administration, blood was collected into heparin-coated Capillary Tubes (VWR) via retro-orbital collection and imaged using Odyssey CLx Imaging System (LI-COR).

In vitro protease cleavage assays

Synthetic biomarkers (6 nM by NP, 300 nM by peptide) were incubated in PBS+1% bovine serum albumin (BSA; Sigma) at 37° C. with murine Granzyme B (0.2 µM, Peprotech), human thrombin (HaemTech), mouse thrombin (HaemTech), mouse plasmin (HaemTech), Clr (Sigma), Cls (Sigma), Factor D (Sigma), Factor I (Sigma), MASP2 (Biomatik). Sample fluorescence were measured for 60 minutes using Cytation 5 plate reader (Biotek). To optimize GzmB substrate, a library of potential substrates was synthesized by Tufts University Core Facility peptide synthesis service and conjugated to IONPs. Cleavage assays of nanoparticles decorated with these substrates with recombinant GzmB were performed, and data was fitted to compare initial cleavage velocities. To determine Michaelis-Menten constants, cleavage assays with GzmB were performed at different substrate concentrations. To initiate coagulation cascade, citrated plasma was mixed with synthetic biomarkers before addition of calcium chloride (15 mM, Sigma). To initiate complement activation, Control Human Serum (Sigma) was mixed with synthetic biomarkers before addition of Heat Aggregated Gamma Globulin (HAGG; Quidel) per the manufacturer's protocol. After measuring fluorescence for 1 hour, supernatants were collected and measured for formation of MAC complex using Micro Vue CH50 Eq EIA Kit (Quidel).

GizmB characterization in transgenic T cell cocultures

EL4 and EG7-OVA cells (ATCC) were grown in RPMI 1640 supplemented with 10% FBS and 25 mM HEPES (Gibco). EG7-OVA cultures were supplemented with G418 (0.4 mg/ml, InvitroGen). CD8 T cells were isolated from OT1 (Jackson Labs) splenocytes by MACS using CD8a Microbeads (Miltenyi). Cells were activated by seeding in 96-well plates coated with anti-mouse CD3e (Clone: 145-2C11, BD) and anti-mouse CD28 (Clone: 37.51, BD) at 2×10^6 cells/ml in RPMI 1640 supplemented with 10% FBS, 100U/ml penicillin-streptomycin, 1X non-essential amino acids (Gibco), 1 mM sodium pyruvate, 0.05 mM 2-mercaptoethanol, and 30U/ml hIL-2 (Roche). After 2 days, cells were transferred to uncoated plates. On day 5, 1×10^6 activated OT1 T cells were coincubated with 1x106 EL4 or EG7-OVA cells for 2 hours at 37° C. and stained for GzmB using anti-mouse GzmB (Clone: NGZB, eBioScience) and Intracellular Fixation & Permeabilization Buffer Set (eBioScience, 88-8824-00). To measure GzmB activity inside target cells, the inventors coincubated activated OT1 CD8 T cells with EL4 and EG7-OVA target cells at various T cell to target cell ratios and stained using GranToxiLux Kit (OncoImmunin, GTL702-8). To measure secretory GzmB, the inventors collected coculture supernatant of OT1 with target cells and performed ELISA with Granzyme B Mouse ELISA Kit (eBioScience, BMS6029).

NP assays sensing T cell killing

To sense transgenic T cell killing, CD8+OT1 T cells were isolated and activated per above protocol. On day 5 post activation, 1x106 OT1 T cells were coincubated with 1x106 EL4 or EG7-OVA target cells for 2 hours at 37° C. Coculture supernatants were mixed with synthetic biomarkers (2 nM by NP, 100 nM by peptides) and fluorescence were monitored for 1 hour at 37° C. To sense alloreactive T cell killing, on day 7 post-transplant, CD8 T cells were isolated from splenocytes and lymphocytes of skin graft mice. 5×10^5 CD8 T cells from skin graft mice were restimulated with 5×105 splenocytes from BALB/c Mice (Charles River) for 6 hours at 37° C. Coculture supernatants were mixed with synthetic biomarkers (2 nM by NP, 100 nM by peptides) and fluorescence were monitored for 2 hours at 37° C.

Skin graft scoring

Skin grafts were qualitatively scored on a scale ranging from 0-4 per established protocol by the Emory Transplant Center. Scoring involved direct observation and palpation of the graft and surrounding tissue. A score of 0 was characterized by complete tissue necrosis, stiffness, and severe discoloration. A score of 4 was characterized by incorporation with surrounding tissue, pliability, and healthy pigmentation.

GzmB characterization in skin graft mouse model

For histological analysis, tissues were collected from skin graft mice at day 7 post-transplant. All tissues were fixed in 4% paraformaldehyde (EMS) overnight at 4° C., washed with PBS and stored in 70% ethanol (VWR) until paraffin-embedding, sectioning, and staining for GzmB and CD8 (Winship Pathology Core). To analyze blood level of GzmB, citrated plasma samples were collected from skin graft mice during rejection and diluted to 10% before performing ELISA with Granzyme B Mouse ELISA Kit (eBioScience, BMS6029). For flow cytometry analysis, 1×106 splenocytes or lymphocytes from skin graft mice were restimulated with 1×106 BALB/c splenocytes for 6 hours at 37° C. before staining for GzmB using anti-mouse GzmB (Clone: NGZB, eBioScience) and Intracellular Fixation & Permeabilization Buffer Set (eBioScience).

NP pharmacokinetics

On day 7 post-transplant, skin graft mice were administered with either NPs (20 ug) or peptides (10 nmol) labelled with VivoTag S-750 (VT750; PerkinElmer). For organ biodistribution, whole mice were imaged with IVIS Spectrum CT Imaging System (PerkinElmer) while excised organs were imaged with Odyssey CLx Imaging System (LI-COR) after 24 hours. For urine pharmacokinetics, whole mice were imaged with IVIS Spectrum CT Imaging System (PerkinElmer) after 30-90 minutes.

Urinary prediction of acute cellular rejection

To track cleaved fragments after in vivo GzmB cleavage, on day 7 post-transplant, VT750-labelled synthetic biomarkers (10 nmol by peptides) were administered to skin graft mice. Major organs were excised and imaged with Odyssey CLx Imaging System (LI-COR) while mouse bladders were imaged with IVIS Spectrum CT Imaging System (PerkinElmer) after 90 minutes. All urinalysis experiments were done in paired setup. 4 days before and 7 days after surgeries, skin graft mice were administered with FITC-labelled Synthetic biomarkers (10 nmol by peptides). Urine were collected after 90 minutes by placing mice over 96-well plates. FITC in urine was purified by a magnetic separation assay using Dynabeads (Thermo, 65501) coated with anti-FITC (Gene-Tex, GTX10257). Fluorescent signals were measured with Cytation 5 Plate Reader (Biotek). Concentrations of FITC were calculated using a free FITC ladder and normalized with urine volume. For CD8 depletion study, mice were given anti-mouse CD8 (clone: 53-6.7, BioXCell) for 3 consecutive days following with booster shots every 3 days after. Flow cytometry analysis of splenocytes and lymphocytes were performed with anti-mouse CD3 (clone: 17A2, Biolegend), anti-mouse CD4 (clone: RM4-5, Biolegend), anti-mouse CD8 (clone: KT15, Serotec) to confirm success of depletion.

Software and Statistical Analysis

Graphs were plotted and appropriate statistical analyses were conducted using GraphPad Prism (*$P<0.05$,  $P<0.01$, * $P<0.001$, **** $P<0.0001$; all error bars depict s.e.m.). Quantification of histological images was performed on ImageJ (NIH). Whole-mouse fluorescent data were analyzed using Living Image (PerkinElmer). Whole-organ fluorescent data were analyzed using Image Studio (LI-COR). Flow cytometry data were analyzed using FlowJo X (FlowJo, LLC).

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims. The scope of the disclosure is therefore indicated by the following claims, rather than the foregoing description and above-discussed embodiments, and all changes that come within the meaning and range of equivalents thereof are intended to be embraced therein.

All patents, applications, publications, test methods, literature, and other materials cited herein are hereby incorporated by reference in their entirety as if physically present in this specification.

TABLE OF SEQUENCES

| SEQ ID NO. | Type | Source | Sequence* |
|---|---|---|---|
| 1 | Protein | Synthetic | IIGGHEVKPHSRPYMALLSIKDQQPEAICGFLIREDFVLTAAHCEGS IINVTLGAHNIKEQEKTQQVIPMVKCIPHPDYNPKTFSNDIMLLKLK SKAKRTRAVRPLNLPRRNVNVKPGDVCYVAGWGRMAPMGKYSNTLQE VELTVQKDRECESYFKNRYNKTNQICAGDPKTKRASFRGDSGGPLVC KKVAAGIVSYGYKDGSPPRAFTKVSSFLSWIKKTMKSS |
| 2 | Protein | Synthetic | AIEPDGSC |
| 3 | Protein | Synthetic | ASGIEPDSGGSC |
| 4 | Protein | Synthetic | AKSKIEFDFGVKKC |
| 5 | Protein | Synthetic | AIEPDSGC |
| 6 | Protein | Synthetic | AIEPDGSSKC |
| 7 | Protein | Synthetic | AIEPDSGSKC |
| 8 | Protein | Synthetic | AKSIEPDGSSKC |
| 9 | Protein | Synthetic | AKSIEPDSGSKC |
| 10 | Protein | Synthetic | AIEFDGSC |
| 11 | Protein | Synthetic | AIEFDSGC |
| 12 | Protein | Synthetic | AIEFDSGSKC |
| 13 | Protein | Synthetic | AKSIEFDSGSKC |
| 14 | Protein | Synthetic | AIEFDSGVSKC |

-continued

| | | | TABLE OF SEQUENCES | |
|---|---|---|---|
| SEQ ID NO. | Type | Source | Sequence* |
| 15 | Protein | Synthetic | AIEPDGSc |
| 16 | Protein | Synthetic | AsGIEPDSGGsc |
| 17 | Protein | Synthetic | AksKIEFDEGVKkc |
| 18 | Protein | Synthetic | AIEPDSGc |
| 19 | Protein | Synthetic | AIEPDGSskc |
| 20 | Protein | Synthetic | AIEPDSGskc |
| 21 | Protein | Synthetic | AksIEPDGSskc |
| 22 | Protein | Synthetic | AksIEPDSGskc |
| 23 | Protein | Synthetic | AIEFDGSc |
| 24 | Protein | Synthetic | AIEFDSGc |
| 25 | Protein | Synthetic | AIEFDSGskc |
| 26 | Protein | Synthetic | AksIEFDSGskc |
| 27 | Protein | Synthetic | AIEFDSGVskc |
| 28 | Protein | Synthetic | EGVNDNEEGFFSAR |
| 29 | Protein | Synthetic | eGvndneeGffsar |
| 30 | Protein | Synthetic | AIEPDGSC |
| 31 | Protein | Synthetic | ASGIEPDSGGSC |
| 32 | Protein | Synthetic | AKSKIEFDFGVKKC |
| 33 | Protein | Synthetic | AIEPDSGC |
| 34 | Protein | Synthetic | AIEPDGSSKC |
| 35 | Protein | Synthetic | AIEPDSGSKC |
| 36 | Protein | Synthetic | AKSIEPDGSSKC |
| 37 | Protein | Synthetic | AKSIEPDSGSKC |
| 38 | Protein | Synthetic | AIEFDGSC |
| 39 | Protein | Synthetic | AIEFDSGC |
| 40 | Protein | Synthetic | AIEFDSGSKC |
| 41 | Protein | Synthetic | AKSIEFDSGSKC |
| 42 | Protein | Synthetic | AIEFDSGVSKC |
| 43 | Protein | Synthetic | aIEPDGSc |
| 44 | Protein | Synthetic | asGIEPDSGGsc |
| 45 | Protein | Synthetic | aksKIEFDFGVKkc |
| 46 | Protein | Synthetic | aIEPDSGc |
| 47 | Protein | Synthetic | aIEPDGSskc |
| 48 | Protein | Synthetic | aIEPDSGskc |
| 49 | Protein | Synthetic | aksIEPDGSskc |
| 50 | Protein | Synthetic | aksIEPDSGskc |
| 51 | Protein | Synthetic | aIEFDGSc |
| 52 | Protein | Synthetic | aIEFDSGc |

-continued

| TABLE OF SEQUENCES | | | |
| --- | --- | --- | --- |
| SEQ ID NO. | Type | Source | Sequence* |
| 53 | Protein | Synthetic | aIEFDSGskc |
| 54 | Protein | Synthetic | aksIEFDSGskc |
| 55 | Protein | Synthetic | aIEFDSGVskc |
| 56 | Protein | Synthetic | EGVNDNEEGFFSARKAIEPDGSC |
| 57 | Protein | Synthetic | EGVNDNEEGFFSARKASGIEPDSGGSC |
| 58 | Protein | Synthetic | EGVNDNEEGFFSARKAKSKIEFDFGVKKC |
| 59 | Protein | Synthetic | EGVNDNEEGFFSARKAIEPDSGC |
| 60 | Protein | Synthetic | EGVNDNEEGFFSARKAIEPDGSSKC |
| 61 | Protein | Synthetic | EGVNDNEEGFFSARKAIEPDSGSKC |
| 62 | Protein | Synthetic | EGVNDNEEGFFSARKAKSIEPDGSSKC |
| 63 | Protein | Synthetic | EGVNDNEEGFFSARKAKSIEPDSGSKC |
| 64 | Protein | Synthetic | EGVNDNEEGFFSARKAIEFDGSC |
| 65 | Protein | Synthetic | EGVNDNEEGFFSARKAIEFDSGC |
| 66 | Protein | Synthetic | EGVNDNEEGFFSARKAIEFDSGSKC |
| 67 | Protein | Synthetic | EGVNDNEEGFFSARKAKSIEFDSGSKC |
| 68 | Protein | Synthetic | EGVNDNEEGFFSARKAIEFDSGVSKC |
| 69 | Protein | Synthetic | eGvndneeGffsarKaIEPDGSc |
| 70 | Protein | Synthetic | eGvndneeGffsarKasGIEPDSGGsc |
| 71 | Protein | Synthetic | eGvndneeGffsarKaksKIEFDFGVKkc |
| 72 | Protein | Synthetic | eGvndneeGffsarKaIEPDSGc |
| 73 | Protein | Synthetic | eGvndneeGffsarKaIEPDGSskc |
| 74 | Protein | Synthetic | eGvndneeGffsarKaIEPDSGskc |
| 75 | Protein | Synthetic | eGvndneeGffsarKaksIEPDGSskc |
| 76 | Protein | Synthetic | eGvndneeGffsarKaksIEPDSGskc |
| 77 | Protein | Synthetic | eGvndneeGffsarKaIEFDGSc |
| 78 | Protein | Synthetic | eGvndneeGffsarKaIEFDSGc |
| 79 | Protein | Synthetic | eGvndneeGffsarKaIEFDSGskc |
| 80 | Protein | Synthetic | eGvndneeGffsarKaksIEFDSGskc |
| 81 | Protein | Synthetic | eGvndneeGffsarKaIEFDSGVskc |
| 82 | Protein | Synthetic | AAPVRSL |
| 83 | Protein | Synthetic | ALDPRSF |
| 84 | Protein | Synthetic | ATQNKAS |
| 85 | Protein | Synthetic | ACYLD |
| 86 | Protein | Synthetic | AIETDGS |
| 87 | Protein | Synthetic | ALEVDCY |
| 88 | Protein | Synthetic | AEPLFAERK |
| 89 | Protein | Synthetic | AMNPKFA |

-continued

| SEQ ID NO. | Type | Source | Sequence* |
|---|---|---|---|
| 90 | Protein | Synthetic | ALQRIYKC |
| 91 | Protein | Synthetic | AKSVARTLLVKC |
| 92 | Protein | Synthetic | AEEKQRIIGC |
| 93 | Protein | Synthetic | AQRQRIIGGC |
| 94 | Protein | Synthetic | ALGRGGSC |
| 95 | Protein | Synthetic | AKYLGRSYKVC |
| 96 | Protein | Synthetic | ARALERGLQDC |
| 97 | Protein | Synthetic | ASLGRKIQIC |
| 98 | Protein | Synthetic | AGLQRALEIC |
| 99 | Protein | Synthetic | AKVFMGRVYDPC |
| 100 | Protein | Synthetic | ASSTGRNGFKC |
| 101 | Protein | Synthetic | AKTTGGRIYGGC |
| 102 | Protein | Synthetic | ADPRGGSC |
| 103 | Protein | Synthetic | AVPRGGSC |
| 104 | Protein | Synthetic | ALPSRSSKIC |
| 105 | Protein | Synthetic | AHRGRTLEIC |
| 106 | Protein | Synthetic | ASTGRNGFKC |
| 107 | Protein | Synthetic | AQQKRKIVLC |
| 108 | Protein | Synthetic | AQARKIVLC |
| 109 | Protein | Synthetic | AQARGGSC |
| 110 | Protein | Synthetic | AIPENFF |
| 111 | Protein | Synthetic | AKEEEGL |
| 112 | Protein | Synthetic | ANLVYMV |
| 113 | Protein | Synthetic | ARLAAIT |
| 114 | Protein | Synthetic | ASLSRLT |
| 115 | Protein | Synthetic | APLGVRGK |
| 116 | Protein | Synthetic | ADEVDNK |
| 117 | Protein | Synthetic | ADEVDGV |
| 118 | Protein | Synthetic | ADEVDRD |
| 119 | Protein | Synthetic | ADEVDGV |
| 120 | Protein | Synthetic | ALE VDCY |
| 121 | Protein | Synthetic | AAAPVc |
| 122 | Protein | Synthetic | AAAPAc |
| 123 | Protein | Synthetic | AAAPLc |
| 124 | Protein | Synthetic | AAAPMc |
| 125 | Protein | Synthetic | AAAPFc |
| 126 | Protein | Synthetic | GGFPRSGGGc |
| 127 | Protein | Synthetic | AGFPRSGGGc |

-continued

| TABLE OF SEQUENCES | | | |
|---|---|---|---|
| SEQ ID NO. | Type | Source | Sequence* |
| 128 | Protein | Synthetic | AIKFFSAc |
| 129 | Protein | Synthetic | ALRQRESc |
| 130 | Protein | Synthetic | AAEFRHDc |
| 131 | Protein | Synthetic | AAAPFc |
| 132 | Protein | Synthetic | AQFVLTEc |
| 133 | Protein | Synthetic | ARETYGEc |
| 134 | Protein | Synthetic | AATVYVDc |
| 135 | Protein | Synthetic | APLDKKRc |
| 136 | Protein | Synthetic | ADKVKAQc |

*Lowercase letters indicate the D form of the amino acid.

REFERENCES

1. V. R. Mas, T. F. Mueller, K. J. Archer, D. G. Maluf, Identifying biomarkers as diagnostic tools in kidney transplantation, *Expert Rev. Mol. Diagn.* 11, 183-196 (2011).
2. W. Gwinner, Renal transplant rejection markers, *World J. Urol.* 25, 445 (2007).
3. L. D. Cornell, R. N. Smith, R. B. Colvin, Kidney Transplantation: Mechanisms of Rejection and Acceptance, *Annu. Rev. Pathol. Mech. Dis.* 3, 189-220 (2008).
4. B. J. Nankivell, S. I. Alexander, Rejection of the Kidney Allograft, *N. Engl. J. Med.* 363, 1451-1462 (2010).
5. A. Moreau, E. Varey, I. Anegon, M.-C. Cuturi, Effector Mechanisms of Rejection, *Cold Spring Harb. Perspect. Med.* 3 (2013), doi: 10.1101/cshperspect.a015461.
6. P. N. Furness, N. Taub, Convergence of European Renal Transplant Pathology Assessment Procedures (CERTPAP) Project, International variation in the interpretation of renal transplant biopsies: report of the CERTPAP Project, *Kidney Int.* 60, 1998-2012 (2001).
7. M. A. Jaffa, R. F. Woolson, S. R. Lipsitz, P. K. Baliga, M. Lopes-*Virella*, D. T. Lackland, Analyses of renal outcome following transplantation adjusting for informative right censoring and demographic factors: A longitudinal study, *Ren. Fail.* 32, 691-698 (2010).
8. M. A. Josephson, Monitoring and Managing Graft Health in the Kidney Transplant Recipient, *Clin. J. Am. Soc. Nephrol.* 6, 1774-1780 (2011).
9. I. D. Vlaminck, H. A. Valantine, T. M. Snyder, C. Strehl, G. Cohen, H. Luikart, N. F. Neff, J. Okamoto, D. Bernstein, D. Weisshaar, S. R. Quake, K. K. Khush, Circulating Cell-Free DNA Enables Noninvasive Diagnosis of Heart Transplant Rejection, *Sci. Transl. Med.* 6, 241ra77-241ra77 (2014).
10. J. C. Choy, Granzymes and perforin in solid organ transplant rejection, *Cell Death Differ.* 17, 567-576 (2010).
11. J. A. Kummer, P. C. Wever, A. M. Kamp, I. J. M. ten Berge, C. E. Hack, J. J. Weening, Expression of granzyme A and B proteins by cytotoxic lymphocytes involved in acute renal allograft rejection, *Kidney Int.* 47, 70-77 (1995).
12. M. Wagrowska-Danilewicz, M. Danilewicz, Immunoexpression of perforin and granzyme B on infiltrating lymphocytes in human renal acute allograft rejection, Nefrol. Publicacion Of. Soc. Espanola Nefrol. 23, 538-544 (2003).
13. B. Li, C. Hartono, R. Ding, V. K. Sharma, R. Ramaswamy, B. Qian, D. Serur, J. Mouradian, J. E. Schwartz, M. Suthanthiran, Noninvasive diagnosis of renal-allograft rejection by measurement of messenger RNA for perforin and granzyme B in urine, *N. Engl. J. Med.* 344, 947-954 (2001).
14. B. Heng, Y. Li, L. Shi, X. Du, C. Lai, L. Cheng, Z. Su, A Meta-analysis of the Significance of Granzyme B and Perforin in Noninvasive Diagnosis of Acute Rejection After Kidney Transplantation, Transplantation 99, 1477-1486 (2015).
15. A. T. Rowshani, S. Florquin, F. Bemelman, J. A. Kummer, C. E. Hack, I. J. M. Ten Berge, Hyperexpression of the granzyme B inhibitor PI-9 in human renal allografts: A potential mechanism for stable renal function in patients with subclinical rejection, *Kidney Int.* 66, 1417-1422 (2004).
16. L. E. Edgington, M. Verdoes, M. Bogyo, Functional imaging of proteases: recent advances in the design and application of substrate-based and activity-based probes, *Curr. Opin. Chem. Biol.* 15, 798-805 (2011).
17. G. A. Kwong, G. von Maltzahn, G. Murugappan, O. Abudayyeh, S. Mo, I. A. Papayannopoulos, D. Y. Sverdlov, S. B. Liu, A. D. Warren, Y. Popov, D. Schuppan, S. N. Bhatia, Mass-encoded synthetic biomarkers for multiplexed urinary monitoring of disease, *Nat. Biotechnol.* 31, 63-70 (2013).
18. A. D. Warren, G. A. Kwong, D. K. Wood, K. Y. Lin, S. N. Bhatia, Point-of-care diagnostics for noncommunicable diseases using synthetic urinary biomarkers and paper microfluidics, *Proc. Natl. Acad. Sci.* 111, 3671-3676 (2014).
19. A. D. Warren, S. T. Gaylord, K. C. Ngan, M. Dumont Milutinovic, G. A. Kwong, S. N. Bhatia, D. R. Walt, Disease Detection by Ultrasensitive Quantification of Microdosed Synthetic Urinary Biomarkers, *J. Am. Chem. Soc.* 136, 13709-13714 (2014).
20. K. Y. Lin, G. A. Kwong, A. D. Warren, D. K. Wood, S. N. Bhatia, Nanoparticles That Sense Thrombin Activity As Synthetic Urinary Biomarkers of Thrombosis, *ACS Nano* 7, 9001-9009 (2013).

21. J. S. Dudani, C. G. Buss, R. T. K. Akana, G. A. Kwong, S. N. Bhatia, Sustained-Release Synthetic Biomarkers for Monitoring Thrombosis and Inflammation Using Point-of-Care Compatible Readouts, *Adv. Funct. Mater.* 26, 2919-2928 (2016).

22. D. F. LaRosa, A. H. Rahman, L. A. Turka, The Innate Immune System in Allograft Rejection and Tolerance, *J. Immunol.* Baltim. Md 1950 178, 7503-7509 (2007).

23. D. N. Mori, D. Kreisel, J. N. Fullerton, D. W. Gilroy, D. R. Goldstein, Inflammatory triggers of acute rejection of organ allografts, *Immunol. Rev.* 258, 132-144 (2014).

24. A. C. Anselmo, S. Mitragotri, Nanoparticles in the clinic, Bioeng. Transl. Med. 1, 10-29 (2016).

25. S. J. Lord, R. V. Rajotte, G. S. Korbutt, R. C. Bleackley, Granzyme B: a natural born killer, *Immunol. Rev.* 193, 31-38 (2003).

26. J. V. Jokerst, T. Lobovkina, R. N. Zare, S. S. Gambhir, Nanoparticle PEGylation for imaging and therapy, *Nanomed.* 6, 715-728 (2011).

27. H. Arami, A. Khandhar, D. Liggitt, K. M. Krishnan, In vivo delivery, pharmacokinetics, biodistribution and toxicity of iron oxide nanoparticles, *Chem Soc Rev* 44, 8576-8607 (2015).

28. J. L. Harris, E. P. Peterson, D. Hudig, N. A. Thornberry, C. S. Craik, Definition and Redesign of the Extended Substrate Specificity of Granzyme B, *J. Biol. Chem.* 273, 27364-27373 (1998).

29. S. M. Waugh, J. L. Harris, R. Fletterick, C. S. Craik, The structure of the pro-apoptotic protease granzyme B reveals the molecular determinants of its specificity, *Nat. Struct. Mol. Biol.* 7, 762-765 (2000).

30. S. W. Ruggles, R. J. Fletterick, C. S. Craik, Characterization of Structural Determinants of Granzyme B Reveals Potent Mediators of Extended Substrate Specificity, *J. Biol. Chem.* 279, 30751-30759 (2004).

31. L. Casciola-Rosen, M. Garcia-Calvo, H. G. Bull, J. W. Becker, T. Hines, N. A. Thornberry, A. Rosen, Mouse and Human Granzyme B Have Distinct Tetrapeptide Specificities and Abilities to Recruit the Bid Pathway, *J. Biol. Chem.* 282, 4545-4552 (2007).

32. J. V. Sarma, P. A. Ward, The Complement System, Cell Tissue Res. 343, 227-235 (2011).

33. S. P. Cullen, M. Brunet, S. J. Martin, Granzymes in cancer and immunity, Cell Death Differ. 17, 616-623 (2010).

34. F. L. Locke, S. S. Neelapu, N. L. Bartlett, T. Siddiqi, J. C. Chavez, C. M. Hosing, A. Ghobadi, L. E. Budde, A. Bot, J. M. Rossi, Y. Jiang, A. X. Xue, M. Elias, J. Aycock, J. Wiezorek, W. Y. Go, Phase 1 Results of ZUMA-1: A Multicenter Study of KTE-C19 Anti-CD19 CAR T Cell Therapy in Refractory Aggressive Lymphoma, *Mol. Ther.* 25, 285-295 (2017).

35. P.-L. Chen, W. Roh, A. Reuben, Z. A. Cooper, C. N. Spencer, P. A. Prieto, J. P. Miller, R. L. Bassett, V. Gopalakrishnan, K. Wani, M. P. D. Macedo, J. L. Austin-Breneman, H. Jiang, Q. Chang, S. M. Reddy, W.-S. Chen, M. T. Tetzlaff, R. J. Broaddus, M. A. Davies, J. E. Gershenwald, L. Haydu, A. J. Lazar, S. P. Patel, P. Hwu, W.-J. Hwu, A. Diab, I. C. Glitza, S. E. Woodman, L. M. Vence, I. I. Wistuba, R. N. Amaria, L. N. Kwong, V. Prieto, R. E. Davis, W. Ma, W. W. Overwijk, A. H. Sharpe, J. Hu, P. A. Futreal, J. Blando, P. Sharma, J. P. Allison, L. Chin, J. A. Wargo, Analysis of Immune Signatures in Longitudinal Tumor Samples Yields Insight into Biomarkers of Response and Mechanisms of Resistance to Immune Checkpoint Blockade, Cancer Discov. 6, 827-837 (2016).

36. S. Rm. Clarke, M. Barnden, C. Kurts, F. R. Carbone, J. F. Miller, W. R. Heath, Characterization of the ovalbumin-specific TCR transgenic line OT-I: MHC elements for positive and negative selection, *Immunol. Cell Biol.* 78, 110-117 (2000).

37. H. Maeda, J. Wu, T. Sawa, Y. Matsumura, K. Hori, Tumor vascular permeability and the EPR effect in macromolecular therapeutics: a review, *J. Control. Release* Off. *J. Control. Release* Soc. 65, 271-284 (2000).

38. G. Fredman, N. Kamaly, S. Spolitu, J. Milton, D. Ghorpade, R. Chiasson, G. Kuriakose, M. Perretti, O. Farokhzad, I. Tabas, Targeted nanoparticles containing the proresolving peptide Ac2-26 protect against advanced atherosclerosis in hypercholesterolemic mice, *Sci. Transl. Med.* 7, 275ra20 (2015).

39. S. Wilhelm, A. J. Tavares, Q. Dai, S. Ohta, J. Audet, H. F. Dvorak, W. C. W. Chan, Analysis of nanoparticle delivery to tumours, *Nat. Rev.* Mater. 1, 16014 (2016).

40. D. Kaiserman, P. I. Bird, Control of granzymes by serpins, Cell Death Differ. 17, 586-595 (2010).

41. S. S. Gambhir, Molecular imaging of cancer with positron emission tomography, *Nat. Rev. Cancer* 2, 683-693 (2002).

42. K. R. Byrnes, C. M. Wilson, F. Brabazon, R. von Leden, J. S. Jurgens, T. R. Oakes, R. G. Selwyn, FDG-PET imaging in mild traumatic brain injury: a critical review, Front. Neuroenergetics 5 (2014), doi: 10.3389/fnene.2013.00013.

43. J. M. Tarkin, F. R. Joshi, J. H. F. Rudd, PET imaging of inflammation in atherosclerosis, *Nat. Rev.* Cardiol. 11, 443-457 (2014).

44. S. Saini, PSA and beyond: alternative prostate cancer biomarkers, Cell. Oncol. Dordr. 39, 97-106 (2016).

45. D. Frees, L. Brøndsted, H. Ingmer, in Regulated Proteolysis in Microorganisms, Subcellular Biochemistry. (Springer, Dordrecht, 2013), pp. 161-192.

46. A. K. Patick, K. E. Potts, Protease Inhibitors as Antiviral Agents, *Clin. Microbiol. Rev.* 11, 614-627 (1998).

47. A. Eatemadi, H. T. Aiyelabegan, B. Negahdari, M. A. Mazlomi, H. Daraee, N. Daraee, R. Eatemadi, E. Sadroddiny, Role of protease and protease inhibitors in cancer pathogenesis and treatment, *Biomed. Pharmacother.* 86, 221-231 (2017).

48. W. Wong, J. DeVito, H. Nguyen, D. Sarracino, F. Porcheray, I. Dargon, P. D. Pelle, A. B. Collins, N. Tolkoff-Rubin, R. N. Smith, R. Colvin, E. Zorn, Chronic Humoral Rejection of Human Kidney Allografts Is Associated with MMP-2 Accumulation in Podocytes and its Release in the Urine, *Am. J. Transplant.* Off. *J. Am.* Soc. Transplant. Am. Soc. Transpl. Surg. 10, 2463-2471 (2010).

49. S. Mauiyyedi, P. D. Pelle, S. Saidman, A. B. Collins, M. Pascual, N. E. Tolkoff-Rubin, W. W. Williams, A. A. Cosimi, E. E. Schneeberger, R. B. Colvin, Chronic humoral rejection: identification of antibody-mediated chronic renal allograft rejection by C4d deposits in peritubular capillaries, *J. Am. Soc. Nephrol.* JASN 12, 574-582 (2001).

50. S. Hailfinger, F. Rebeaud, M. Thome, Adapter and enzymatic functions of proteases in T-cell activation, Immunological Reviews 232, 334-347 (2009).

51. M. D. Stegall, M. F. Chedid, L. D. Cornell, The role of complement in antibody-mediated rejection in kidney transplantation, *Nat Rev* Nephrol 8, 670-678 (2012).

52. J. Zegarska, L. Paczek, M. Pawlowska, I. Bartlomiejczyk, W. Rowinski, M. Kosieradzki, P. Malanowski, A. Kwiatkowski, T. Grochowiecki, J. Szmidt, Extracellular matrix proteins, proteolytic enzymes, and TGF-betal in the renal arterial wall of chronically rejected renal allografts, *Transplant. Proc.* 35, 2193-2195 (2003).

53. W. Wong, J. DeVito, H. Nguyen, D. Sarracino, F. Porcheray, I. Dargon, P. D. Pelle, A. B. Collins, N. Tolkoff-Rubin, R. N. Smith, R. Colvin, E. Zorn, Chronic humoral rejection of human kidney allografts is associated with MMP-2 accumulation in podocytes and its release in the urine, *Am. J. Transplant.* 10, 2463-2471 (2010).

What is claimed is:

1. A method of detecting a T cell cytotoxicity driven immune condition and/or the likelihood thereof in a subject, the method comprising:

i) administering a nanosensor to the subject, said nanosensor comprising:
      a) a scaffold;
      b) a peptide substrate coupled to the scaffold, wherein the peptide substrate is capable of being cleaved by Granzyme B; and
      c) a detectable reporter coupled to the scaffold by the peptide substrate, wherein in vivo cleavage of said peptide substrate releases said detectable reporter from the scaffold;

ii) detecting a level of said detectable reporter in a blood or urine sample collected from the subject; wherein the presence of detectable reporter indicates the subject has or is likely to have a T cell cytotoxicity driven immune condition; and iii) treating the subject for a T cell cytotoxicity driven immune condition when the detectable reporter is detected.

2. The method of claim 1, wherein said nanosensor comprises said detectable reporter selected from a group consisting of a fluorophore, a luminescent reporter, a ligand encoded reporter, a mass spectrometry tag, a contrast agent for imaging, a PET-detectable domain, and a nucleic acid tag.

3. The method of claim 2, wherein said detectable reporter further comprises a quencher.

4. The method of claim 1, wherein said peptide substrate comprises an amino acid sequence selected from the group consisting of SEQ ID Nos: 2-136.

5. The method of claim 1, wherein ii) further comprises comparing said level of said detectable reporter to a reference level of detectable reporter in a subject without a T cell cytotoxicity driven immune condition.

6. The method of claim 1, wherein i) comprises intravenously administering the nanosensor to the subject.

7. The method of claim 1, wherein the scaffold comprises a protein scaffold, a polymer scaffold, a DNA scaffold, a sugar scaffold, or a nanoparticle.

* * * * *